United States Patent
Liu et al.

(10) Patent No.: US 11,746,160 B2
(45) Date of Patent: Sep. 5, 2023

(54) ANTIBODIES AGAINST BACE1 AND USE THEREOF FOR NEURAL DISEASE IMMUNOTHERAPY

(71) Applicants: Genentech, Inc., South San Francisco, CA (US); Adimab LLC, Lebanon, NH (US)

(72) Inventors: Yichin Liu, South San Francisco, CA (US); Jasvinder Atwal, South San Francisco, CA (US); Cecilia Pui Chi Chiu, Redwood City, CA (US); Ryan J. Watts, South San Francisco, CA (US); Yan Wu, Foster City, CA (US); Eric Krauland, Lebanon, NH (US); Michael Feldhaus, Lebanon, NH (US)

(73) Assignees: Genentech, Inc., South San Francisco, CA (US); Adimab LLC, Lebanon, NH (US)

( * ) Notice: Subject to any disclaimer, the term of this patent is extended or adjusted under 35 U.S.C. 154(b) by 267 days.

(21) Appl. No.: 17/113,711

(22) Filed: Dec. 7, 2020

(65) Prior Publication Data
US 2021/0206877 A1 Jul. 8, 2021

Related U.S. Application Data

(62) Division of application No. 15/525,791, filed as application No. PCT/US2015/061401 on Nov. 18, 2015, now Pat. No. 10,882,920.

(60) Provisional application No. 62/081,966, filed on Nov. 19, 2014.

(51) Int. Cl.
| | | |
|---|---|---|
| C12N 15/52 | (2006.01) | |
| C07K 16/40 | (2006.01) | |
| A61K 47/68 | (2017.01) | |
| G01N 33/573 | (2006.01) | |
| A61K 39/00 | (2006.01) | |

(52) U.S. Cl.
CPC .......... *C07K 16/40* (2013.01); *A61K 47/6871* (2017.08); *C12N 15/52* (2013.01); *C12Y 304/23046* (2013.01); *G01N 33/573* (2013.01); *A61K 2039/505* (2013.01); *A61K 2039/54* (2013.01); *A61K 2039/545* (2013.01); *C07K 2317/21* (2013.01); *C07K 2317/56* (2013.01); *C07K 2317/565* (2013.01); *C07K 2317/76* (2013.01); *C07K 2317/90* (2013.01); *C07K 2317/92* (2013.01); *G01N 2333/96472* (2013.01); *G01N 2800/28* (2013.01); *G01N 2800/52* (2013.01)

(58) Field of Classification Search
CPC ................ C07K 16/40; C07K 2317/21; C07K 2317/56; C07K 2317/565; C07K 2317/76; C07K 2317/90; C07K 2317/92; A61K 47/6871; A61K 2039/505; A61K 2039/54; A61K 2039/545; C12Y 304/23046; G01N 33/573; G01N 2333/96472; G01N 2800/28; G01N 2800/52; G01N 33/6893; G01N 33/6896; A61P 9/00; A61P 9/10; A61P 21/02; A61P 21/04; A61P 25/00; A61P 25/14; A61P 25/16; A61P 25/20; A61P 25/28; A61P 27/06; A61P 35/00
See application file for complete search history.

(56) References Cited

U.S. PATENT DOCUMENTS

| | | |
|---|---|---|
| 5,200,339 A | 4/1993 | Abraham |
| 5,744,346 A | 4/1998 | Chrysler et al. |
| 5,849,560 A | 12/1998 | Abraham |
| 5,942,400 A | 8/1999 | Anderson et al. |
| 6,221,645 B1 | 4/2001 | Chrysler et al. |
| 6,319,689 B1 | 11/2001 | Powell et al. |
| 6,329,163 B1 | 12/2001 | Anderson et al. |
| 6,545,127 B1 | 4/2003 | Tang et al. |
| 6,627,739 B1 | 9/2003 | Anderson et al. |
| 6,706,485 B1 | 3/2004 | Gurney et al. |
| 6,727,074 B2 | 4/2004 | Gurney et al. |
| 6,852,482 B1 | 2/2005 | Chrysler et al. |
| 7,067,271 B1 | 6/2006 | Anderson et al. |
| 7,109,017 B1 | 9/2006 | Anderson et al. |
| 7,115,410 B1 | 10/2006 | Anderson et al. |
| 7,244,708 B2 | 7/2007 | Tang et al. |
| 7,252,963 B2 | 8/2007 | Anderson et al. |
| 7,262,043 B2 | 8/2007 | Anderson et al. |
| 7,276,349 B2 | 10/2007 | Anderson et al. |
| 7,314,726 B2 | 1/2008 | Komacker et al. |
| 7,413,737 B2 | 8/2008 | Wittrup et al. |
| 7,456,007 B1 | 11/2008 | Anderson et al. |
| 7,479,372 B2 | 1/2009 | Brady et al. |
| 7,514,408 B1 | 4/2009 | John et al. |

(Continued)

FOREIGN PATENT DOCUMENTS

| | | |
|---|---|---|
| WO | 1992003542 A1 | 3/1992 |
| WO | 1996040885 A2 | 12/1996 |

(Continued)

OTHER PUBLICATIONS

Dondelinger et al., "Understanding the Significance and Implications of Antibody Numbering and Antigen-Binding Surface/Residue Definition", Frontiers in Immunology, vol. 9, pp. 1-15 (2018).
Bernhardt, Wiebke, Examiner, Partial European Search Report for European Application No. 20204109.1, dated May 11, 2021, 20 pages.
Pajoohesh-Ganji et al., "Inhibition of amyloid precursor protein secretases reduces recovery after spinal cord injury," Brain Res., 1560: 73-82 (2014).

(Continued)

*Primary Examiner* — Kimberly Ballard
*Assistant Examiner* — Stacey N MacFarlane
(74) *Attorney, Agent, or Firm* — McNeill Baur PLLC

(57) ABSTRACT

The invention provides antagonistic antibodies to BACE1 and methods of using the same for the treatment of neurological disease and disorders.

6 Claims, 38 Drawing Sheets
Specification includes a Sequence Listing.

(56) References Cited

U.S. PATENT DOCUMENTS

| | | | |
|---|---|---|---|
| 7,569,391 | B2 | 8/2009 | Beyer et al. |
| 7,579,180 | B2 | 8/2009 | Citron et al. |
| 7,582,465 | B2 | 9/2009 | Citron et al. |
| 7,601,528 | B1 | 10/2009 | Benson et al. |
| 7,630,838 | B2 | 12/2009 | Chopra et al. |
| 7,678,760 | B2 | 3/2010 | Tang et al. |
| 7,691,977 | B2 | 4/2010 | Fuh et al. |
| 7,696,330 | B2 | 4/2010 | Meulen et al. |
| 7,758,859 | B2 | 7/2010 | Fuh et al. |
| 7,790,864 | B2 | 9/2010 | Desire |
| 7,799,899 | B2 | 9/2010 | Ackerly et al. |
| 7,825,221 | B2 | 11/2010 | Kirchhofer et al. |
| 7,829,669 | B2 | 11/2010 | Koelsch et al. |
| 7,834,154 | B2 | 11/2010 | Koch et al. |
| 7,989,597 | B2 | 8/2011 | Chang et al. |
| 8,414,890 | B2 | 4/2013 | Martin et al. |
| 9,453,079 | B2 | 9/2016 | Atwal et al. |
| 2002/0055459 | A1 | 5/2002 | Chopra et al. |
| 2007/0149763 | A1 | 6/2007 | Komacker et al. |
| 2008/0215249 | A1 | 9/2008 | Benson et al. |
| 2008/0247951 | A1 | 10/2008 | Koch et al. |
| 2009/0125289 | A1 | 5/2009 | Benson et al. |
| 2010/0047232 | A1 | 2/2010 | Atwal et al. |
| 2010/0055103 | A1 | 3/2010 | Chen et al. |
| 2010/0233156 | A1 | 9/2010 | Burns et al. |
| 2012/0171120 | A1 | 7/2012 | Dennis et al. |
| 2012/0237526 | A1 | 9/2012 | Strooper et al. |
| 2012/0282176 | A1 | 11/2012 | Bohrmann et al. |
| 2018/0057604 | A1 | 3/2018 | Liu et al. |

FOREIGN PATENT DOCUMENTS

| | | |
|---|---|---|
| WO | 9826059 A1 | 6/1998 |
| WO | 0100663 A2 | 1/2001 |
| WO | 0100665 A2 | 1/2001 |
| WO | 0129563 A1 | 4/2001 |
| WO | 0206306 A2 | 1/2002 |
| WO | 0247466 A2 | 6/2002 |
| WO | 02053594 A2 | 7/2002 |
| WO | 03039454 A2 | 5/2003 |
| WO | 03102244 A1 | 12/2003 |
| WO | 2004035606 A2 | 4/2004 |
| WO | 2004099402 A1 | 11/2004 |
| WO | 2005014815 A1 | 2/2005 |
| WO | 2006038684 A1 | 4/2006 |
| WO | 2007021886 A2 | 2/2007 |
| WO | 2007056470 A2 | 5/2007 |
| WO | 2007127506 A2 | 11/2007 |
| WO | 2007140371 A2 | 12/2007 |
| WO | 2007130697 A3 | 3/2008 |
| WO | 2008052187 A2 | 5/2008 |
| WO | 2008129023 A3 | 6/2009 |
| WO | 2009155609 A1 | 12/2009 |
| WO | 2009121948 A3 | 1/2010 |
| WO | 2010146058 A1 | 12/2010 |
| WO | 2012064836 A1 | 5/2012 |
| WO | 2012075037 A1 | 6/2012 |
| WO | 2013056054 A3 | 7/2013 |
| WO | 2013177062 A2 | 11/2013 |
| WO | 2014145806 A3 | 2/2015 |
| WO | 2016081640 A1 | 5/2016 |

OTHER PUBLICATIONS

Paul, Steven M., "Therapeutic Antibodies for Brain Disorders", Science Translational Medicine, AMS-American Association for the Advancement of Science, vol. 3, No. 84, May 25, 2011.

Pluckthun, "Antibodies from *Escherichia coli*" The Pharmacology of Monoclonal Antibodies 11 (1994).

Polson et al., "Antibody-drug conjugates targeted to CD79 for the treatment of non-Hodgkin lymphoma," Blood, vol. 10, No. 2, pp. 616-623 (2007).

Rajendran et al., "Efficient Inhibition of the Alzheimer's Disease β-Secretase by Membrane Targeting" Science 320:520-523 (2008).

Reardon et al., "Alzheimer's Drug Sneaks Through Blood-Brain Barrier", Nature News, Nov. 5, 2014, 3 pages.

Richards et al., "PS2APP Transgenic Mice, Coexpressing hPS2mut and hAPPswe, Show Age-Related Cognitive Deficits Associated with Discrete Brain Amyloid Deposition and Inflammation" Journal of Neuroscience 23(26):8989-9003 (2003).

Roberds et al., "BACE Knockout Mie are Healthy Despite Lacking the Primary β-Secretase Activity in Brain: Implications for Alzheimer's Disease Therapeutics" Human Molecular Genetics 10(12):1317-1324 (2001).

Rudikoff et al., "Single amino acid substitution altering antigen-binding specificity" Proc. Natl.Acad. Sci. 79 (1mmunology):1979-1983 (Mar. 1982).

Salum et al., "Fragment-Guided Approach to Incorporating Structural Information into a CoMFA Study: BACE-1 as an Example" Journal Comput. Aided Mol. Des. 24:803-817 (2010).

Shimizu et al., "Crystal Structure of and Active Form of BACE1, an Enzyme Responsible for Amyloid Protein Production", Molecular and Cellular Biology, vol. 28, No. 11, Jun. 1, 2008, pp. 3663-3671.

Sidhu et al., "Phage Display for Selection of Novel Binding Peptides" Method Enzymol 328:333-363 (2000).

Sidhu et al., "Phage-displayed Antibody Libraries of Synthetic Heavy Chain Complementarity Determining Regions" J. Mol. Bol 338:299-31 O (2004).

Singer et al., "Targeting BACE1 with siRNAs Ameliorates Alzheimer Disease Neuropathology in a Transgenic Model" Nature Neuroscience 8(10): 1343 (2005).

Sinha et al., "Purification and Cloning of Amyloid Precursor Protein β-Secretase from Human Brain" Nature 402:537-540 (1999).

Sopper et al., "Lymphocyte Subsets and Expression of Differentiation Markers in Blood and Lymphoid Organs of Rhesus Monkeys", Cytometry vol. 29, No. 4, Dec. 1, 1997, pp. 351-362.

Stachel et al., "Progress Toward the Development of a Viable BACE-1 Inhibitor" Drug Development Research 70:101-110 (2009).

Strooper et al., "The Secretases: Enzymes with Therapeutic Potential in Alzheimer Disease" Nature Reviews Neurology 6:99-107 (2010).

Tabrizi et al., "Biodistribution Mechanisms of Therapeutic Monoclonal Antibodies in Health and Disease," The AAPS Journal, vol. 12 (2010) 33-43.

Turner et al., "Structural Locations and Functional Roles of New Subsites S5, S6, and S7 in Memapsin 2 (β-Secretase)" Biochemistry 44:105-112 (2005).

UniProtKB/Swiss-Pro Entry, Accession No. P56817.

Vajdos et al., "Comprehensive Functional Maps fo the Antigen-binding Site of an Anti-ErbB2 Antibody Obtained with Shotgun Scanning Mutagenesis," Elsevier Science Ltd , pp. 415-427 (2002).

Van Dijk et al., "Human antibodies as next generation therapeutics" Current Opinion in Chemical Biology 5:368-374 (2001).

Varghese et al., "Human β-Secretase (BACE) and BACE Inhibitors: Progess Report" Current Topics in Medicinal Chemistry 6:569-578 (2006).

Vassar et al., "The Beta-Secretase Enzyme BACE in Health and Alzheimer's Disease: Regulation, Cell Biology, Function, and Therapeutic Potential", Journal of Neuroscience, vol. 29, No. 41, Oct. 14, 2009, pp. 12787-12794.

Vassar et al., "β-Secretase Cleavage of Alzheimer's Amyloid Precursor Protein by the Transmembrane Aspartic Protease BACE" Science 286:735-741 (1999).

Vassar, "The β-Secretase, BACE" Journal of Molecular Neuroscience 17:157-170 (2001).

Vassar, "β-Secretase (BACE) as a Drug Target for Alzheimer's Disease" Advanced Drug Delivery Reviews 54:1589-1602 (2002).

Wang et al., "Allosteric Inhibition of BACE1 by an Exosite-binding Antibody", Current Opinion in Structural Biology, vol. 23, No. 6, Dec. 1, 2013, pp. 797-805.

Yan et al., "Membrane-Anchored Aspartyl Protease with Alzheimer's Disease β-Secretase Activity" Nature 402:533-537 (1999).

Yu et al., "Boosting Brain Uptake of a Therapeutic Antibody by Reducing its Affinity for a Transcytosis Target", Science Translational Medicine, AAAS—American Association for the Advancement of Science, vol. 3, No. 84, May 25, 2011, pp. 1-8.

(56) References Cited

OTHER PUBLICATIONS

Ku et al., "Therapeutic bispecific cross the blood-brain barrier in nonhuman primates," Science Translational Medicine 6(261):1-11 (Nov. 5, 2014).
Zhou et al., "Inhibition of β-Secretase in Vivo via Antibody Binding to Unique loops (D and F) of BACE1" Journal of Biological Chemistry 286(10):8677-8687 (2011).
Arbel et al., "Immunotherapy for Alzheimer's Disease: Attacking Amyloid-13 from the Inside" Trends in Immunology 28(12):511-513 (2007).
Atwal et al., "A Therapeutic Antibody Targeting BACE1 Inhibits Amyloid-[Beta] Production in Vivo", Science Translational Medicine, AAAS-American Association of the the Advancement of Science, vol. 3, No. 84, May 25, 2011, 14 pages.
Bhattacharya et al., "Impact of genetic variation on three dimensional structure and function of proteins", PLOS One, Mar. 15, 2017 (22 pgs.).
Bigott-Hennkens et al., "In Vitro Receptor Binding Assays: General Methods and Considerations", The Quarterly Journal of Nuclear Medicine and Molecular Imaging, vol. 52, No. 3, Sep. 1, 2008, pp. 245-253.
Birtalan et al., "The Functional Capacity of the Natural Amino Acids for Molecular Recognition" Molecular Biosystems 6:1186-1194 (2010).
Cai et al., "BACE1 is the Major β-Secretase for Generation of AI3 Peptides by Neurons" Nature Neuroscience 4(3):233-234 (2001).
Carter et al., "Humanization of an anti-p185 HER2 antibody for human cancer therapy" P Natl Acad Sci USA 89:4285-4289 (May 1992).
Chang et al., "Amyloid-beta reduction by memapsin 2 (beta-secretase) immunization" The FASEB Journal 21:3184-3196 (2007).
Chang et al., "In Vivo Inhibition of AB Production by Memapsin 2 (β-Secretase) Inhibitors" Journal of Neurochemistry 89:1409-1416 (2004).
Chang et al., "P2-323: Memapsin 2 (beta-secretase, BACE) immunization as specific and safe therapy for Alzheimer's disease" Alzheimer's & Dementia 4(3):T467 (Jul. 2008).
Charrier et al., "Second Generation of Hydroxyethylamine BACE-1 Inhibitors: Optimizing Potency and Oral Bioavailability" Journal Med. Chem. 51 :3313-3317 (2008).
Chezal et al., "Evaluation of Radiolabeled (Hetero) Armatic Analogues of N-(2-diethylaminoethyl)-4-lodobenzamide for imaging and Targeted Radionuclide Therapy of Melanoma" Journal of Med. Chem. 51:3133-3144 (2008).
Citron, "β-Secretase as a Target for the Treatment of Alzheimer's Disease" Journal of Neuroscence Research 70:373-379 (2002).
Clackson et al., "Making antibody fragments using phage display libraries" Nature 352:624-628 (Aug. 1991).
Cole et al., "BACE1 Structure and Function in Health and Alzheimer's Disease", Current Alzheimer Research, Bentham Science Publication, vol. 5, No. 2, Apr. 1, 2008, pp. 100-120.
Couch et al., "Addressing Safety Liabilities of TfR Bispecific Antibodies that Cross the Blood-Brain barrier", Science Translational Medicine, AMS-American Association for the Advancement of Science, vol. 5, No. 183, May 1, 2013, 14 pages.
Dominguez et al., "Phenotypic and Biochemical Analyses of BACE1- and BACE2-Deficient Mice" Journal of Biological Chemistry 280(35):30797-30806 (2005).
Duebel, Stephen, "Handbook of Therapeutic Antibodies Chapter 6", Handbook of Therapeutic Antibodies, Wiley-VCH Weinheim, Jan. 1, 2007; pp. 119-144.
European Search Report for European Application No. 16194064.8, dated Apr. 24, 2017, 11 pages.
Fellouse et al., "High-throughput generation of synthetic antibodies from highly functional minimalist phage-displayed libraries" J Mol Biol. 373(4):924-40 (Nov. 2007).
Frank et al., "Strategies for enhancing antibody delivery to the brain," Biochimica et Biophysica Acta 1816 (2011) 191-198.

Gallop et al. et al., "Applications of combinatorial technologies to drug discovery. 1. background and peptide combinatorial libraries" J Med Chem 37(9): 1233-1251 (1994).
Gen Bank Accession No. AA T76270.1, immunoglobulin light chain variable region, partial (Mus musculus), pp. 1 (published 2005).
Ghosh et al., "β-Secretase as a Therapeutic Target for Alzheimer's Disease" Neurotherapeutics 5:399-408 (2008).
Haniu et al., "Characterization of Alzheimer's β-Secretase Protein BACE" Journal of Biological Chemistry 257:21099-21106 (2000).
Hong et al., "Structure of the Protease Domain of Memapsin 2 (β-Secretase) Complexed with Inhibitor" Science 290:150-153 ( 2000).
Hoogenboom, "Overview of Antibody Phage-Display Technology and Its Applications" Methods in Molecular Biology 178: 1-37(2001).
Howlett et al., "In Search of an Enzyme: The β-Secretase of Alzheimer's Disease is an Aspartic Proteinase" Trends in Neuroscience 23(11):565-570 ( 2000).
Hu et al., "Genetic deletion of BACE1 in mice affects remyelination of sciatic nerves," FASEB J., 22: 2970-2980 (2008).
Hussain et al., "Identification of a Novel Aspartic Protease (Asp 2) as β-Secretase" Molecular and Cellular Neuroscience 14(6):419-427 (1999).
International Search Report and Written Opinion issued in PCT/US2015/061401, dated May 3, 2016, 29 pages.
International Search Report and Written Opinion issued in PCT/US2015/061402, dated Mar. 1, 2016, 20 pages.
International Search Report for PCT/US2011/059964 (May 2013).
Komacker et al., "An Inhibitor Binding Pocket Distinct from the Catalytic Active Site on Human 13-APP Cleaving Enzyme" Biochemistry 44:11567-11573 (2005).
Kunkel et al., "Rapid and Efficient Site-specific Mutagenesis Without Phenotypic Selection" Method Enzymol 154:367-382 (1987).
Laird et al., "BACE1, Major Determinant of Selective Vulnerability of the Brain to Amyloid-B Amyloidogenesis, is Essential for Cognitive, Emotional, and Synaptic Functions" Journal of Neuroscience 25(50):11693-11709 (2005).
Lee et al., "High-affinity human antibodies from phage-displayed synthetic Fab libraries with a single framework scaffold" J Mol Biol 340(5):1073-1093 (2004).
Lemere et al., "Can Alzheimer Disease Be Prevented by Amyloid-βimmunotherapy" Nature Rev. Neurol. 6:108-119 (2010).
Lin et al., "Human Aspartic Protease memapsin 2 Cleaves the β-Secretase Site of β-Amyloid Precursor Protein" PNAS 97(4): 1456-1460 (2000).
Liu et al., "Amyloid B peptide alters intracellular vesicle trafficking and cholesterol homeostasis," Proc. Natl. Acad. Sci. USA, 95: 13266-13271 (1998).
Liu et al., "Glu 1 Site Cleavage and N-Terminally AB Production upon BACE Overexpression" Biochemistry 41 :3128-3136 (2002).
Luo et al., "Mice deficient in BACE1, the Alzheimer's β-Secretase, have Normal Phenotype and Abolished 13-Amyloid Generation" Nature Neuroscience 4(3):231-232 (2001).
Marks et al., "By-passing Immunization Human Antibodies from V-gene Libraries Displayed on Phage" J. Mol. Biol. 222:581-597 (1991).
Marks et al., "Selection of Human Antibodies from Phage Display Libraries" Methods in Molecular Biology 248:161-176 (2003).
McCafferty et al., "Phage antibodies: filamentous phage displaying antibody variable domains" Nature 348:552-554 (Dec. 6, 1990).
McConlogue et al., "Partial Reduction of BACE1 Has Dramatic Effects on Alzheimer Plaque and Synaptic Pathology in APP Transgenic Mice", Journal of Biological Chemistry, vol. 282, No. 36, Jun. 29, 2006, pp. 26326-26334.
McGuaghey et al., "Structure-Guided Design of β-Secretase (BACE-1) Inhibitors" Expert Opinion Drug Discov. 2 (8): 1129-1138 (2007).
Morris, Glenn E., "Epitope Mapping of Protein Antigens by Competition ELISA", The Protein Protocols Handbook, Jan. 1, 1996, pp. 595-600.
Nikolaev et al., "APP binds DR6 to trigger axon pruning and neuron death via distinct caspases" NATURE 457:981-990 (Feb. 19, 2009).

(56) References Cited

OTHER PUBLICATIONS

Ohno et al., "BACE1 Deficiency Rescues Memory Deficits and Cholinergic Dysfunction in a Mouse Model of Alzheimer's Disease" Neuron 41 :27-33 (2008).

| Ab Name | Epitope bin | VH HVR1 | H1 SEQ | VH HVR2 | H2 SEQ | VH HVR3 | H3 SEQ |
|---|---|---|---|---|---|---|---|
| 5531 | 2 | FTFSSYAMS | 1 | AISGSGGSTYYADSVKG | 22 | AKGGSQWLYAPGSWFDP | 50 |
| 5586 | 2 | FTFSSYAMS | 1 | AISGSGGSTYYADSVKG | 22 | AKGGSQWLYAPGSWFDP | 50 |
| 5583 | 2 | FTFSSYAMS | 1 | AISGSGGSTYYADSVKG | 22 | AKGGSQWLYAPGSWFDP | 50 |
| 5532 | 2 | FTFSSYAMS | 1 | AISGSGGSTYYADSVKG | 22 | AKGAGHGSYVKGWFDP | 51 |
| 5592 | 2 | FTFSSYAMS | 1 | AISGSGGSTYYADSVKG | 22 | AKGAGHGSYVKGWFDP | 51 |
| 5878 | 2 | FTFSSYAMS | 1 | AISGSGGSISTPYADSVKG | 25 | AKGAGHGSYVKGWFDP | 51 |
| 5874 | 2 | FTFGSYAMS | 2 | ATSGSGGSTYYADSVKG | 23 | AKGGSQWLYAPGSWFDP | 50 |
| 5875 | 2 | FTFSTYAMG | 3 | ATSGSGGSIYYADSVKG | 23 | AKGGSQWLYAPGSWFDP | 50 |
| 5876 | 2 | FTFSSRAMG | 4 | ATSGSGGSIYYADSVKG | 24 | AKGGSQWLYAPGSWFDP | 50 |
| 5880 | 2 | FTFGSYAMT | 5 | AISGSGSISTPYADSVKG | 25 | AKGAGHGSYVKGWFDP | 51 |
| 5881 | 2 | FTFSKYAMS | 6 | AISGSGSISTPYADSVKG | 25 | AKGAGHGSYVKGWFDP | 51 |
| 5260 | 3 | GTFSSYAIS | 7 | SIIPIFGTANYAQKFQG | 26 | ARSGGTKYGMLDV | 52 |
| 5572 | 3 | GTFSSYAIS | 7 | SIIPIFGTANYAQKFQG | 26 | ARSGGTKYGMLDV | 52 |
| 5536 | 3 | GTFSSYAIS | 7 | SIIPIFGTANYAQKFQG | 26 | ARSGGTKYGMLDV | 52 |
| 5571 | 3 | GTFSSYAIS | 7 | NIIPIFGTANYAQKFQG | 27 | ARSGGTKYGMLDV | 52 |
| 5883 | 3 | GTFSSYAIS | 7 | GIIPIGGANYAQKFQG | 28 | ARSGGTKYGMLDV | 52 |
| 5890 | 3 | GTFSSYAIS | 7 | NIIPGFGTANYAQKFQG | 29 | ARSGGTKYGMLDV | 52 |
| 5891 | 3 | GTFSSYAIS | 7 | NIIPIFGPANYAQKFQG | 31 | ARSGGTKYGMLDV | 52 |
| 5892 | 3 | GTFSSYAIS | 7 | NIIPIFGTATYAQKFQG | 232 | ARSGGTKYGMLDV | 52 |
| 5884 | 3 | GTFSGYGIS | 8 | NIIPGFGTANYAQKFQG | 29 | ARSGGTKYGMLDV | 52 |
| 6272 | 3 | GTFSGYGIS | 8 | NIIPGFGTANYAQKFQG | 29 | ARSGGTKYGMLDV | 52 |
| 6270 | 3 | GTFSGYGIS | 8 | NIIPGFGTANYAQKFQG | 29 | ARSGGTKYGMLDV | 52 |
| 6273 | 3 | GTFSGYGIS | 8 | NIIPGFGTANYAQKFQG | 29 | ARSGGTKYGMLDV | 52 |

FIG. 1A

| Ab Name | Epitope bin | VH HVR1 | H1 SEQ | VH HVR2 | H2 SEQ | VH HVR3 | H3 SEQ |
|---|---|---|---|---|---|---|---|
| 6274 | 3 | GTFSGYGIS | 8 | NIIPGFGTANYAQKFQG | 29 | ARSGGTKYGMLDV | 52 |
| 5893 | 3 | GTFRGYAIS | 9 | NIIPGFGTANYAQKFQG | 29 | ARSGGTKYGMLDV | 52 |
| 5887 | 3 | GTFRGYAIS | 9 | NIIPGFGTANYAQKFQG | 29 | ARSGGTKYGMLDV | 52 |
| 6275 | 3 | GTFRGYAIS | 9 | NIIPGFGTANYAQKFQG | 29 | ARSGGTKYGMLDV | 52 |
| 6279 | 3 | GTFRGYAIS | 9 | NIIPGFGTANYAQKFQG | 29 | ARSGGTKYGMLDV | 52 |
| 6276 | 3 | GTFRGYAIS | 9 | NIIPGLSTANYAQKFQG | 39 | ARSGGTKYGMLDV | 52 |
| 5888 | 3 | GTFWKYAIS | 10 | NIIPGFGTANYAQKFRG | 30 | ARSGGTKYGMLDV | 52 |
| 5894 | 3 | GTFSGYAIS | 11 | NIIPGFGTANYAQKFQG | 29 | ARSGGTKYGMLDV | 52 |
| 5543 | 3 | GSISSSSYYWG | 12 | SIYYSGSTYYNPSLKS | 32 | ARVGHGISYFDL | 53 |
| 5643 | 3 | GSISSSSYYWG | 12 | SIYYSGSTYYNPSLKS | 32 | ARVGHGISYFDL | 53 |
| 5644 | 3 | GSISSSSYYWG | 12 | SIYYSGSTYYNPSLKS | 32 | ARVGHGISYFDL | 53 |
| 5896 | 3 | GSISSSSYYWG | 12 | SIYRSGSTYYNPSLKS | 33 | ARVGHGISYFDL | 53 |
| 5902 | 3 | GSISSSSYYWG | 12 | SIYRSGSTWYNPSLKS | 35 | ARVGHGISYFDL | 53 |
| 5903 | 3 | GSISSSSYYWG | 12 | MIYYSGSTWYNPSLKS | 36 | ARVGHGISYFDL | 53 |
| 6290 | 3 | GSISSSSYYWG | 12 | MIYYSGSTWYNPSLKS | 36 | ARVGLGVSYFDL | 56 |
| 6291 | 3 | GSISSSSYYWG | 12 | MIYYSGSTWYNPSLKS | 36 | ARVGHGVSYFDL | 57 |
| 6293 | 3 | GSISSSSYYWG | 12 | SIYRSGSTYYNPSLRS | 41 | ARVGHGISYFDL | 57 |
| 6289 | 3 | GSISSSSYYWG | 12 | SIYRSGSTYYNPSLRS | 43 | VRVGHGISYFDL | 58 |
| 5747 | 3 | GSISSSSYYWG | 12 | NIYYSGSTYYNPSLKS | 44 | ARLGHGYSYFDL | 59 |
| 5982 | 3 | GSISSSSYYWG | 12 | NIYYSGSTYYNPSLKS | 44 | ARLGHGYSYFDL | 59 |
| 5985 | 3 | GSISSSSYYWG | 12 | NIYYSGSTYYNPSLRS | 44 | ARLGHGYNYFDL | 60 |
| 5983 | 3 | GSISSSSYYWG | 12 | NIYYSGSTYYNPSLRS | 45 | ARLGHGYNYFDL | 60 |
| 5984 | 3 | GSISSSSYYWG | 12 | NIYYSGSTYYNPSLKG | 46 | ARLGHGYNYFDL | 60 |

FIG. 1B

| Ab Name | Epitope bin | VH HVR1 | H1 SEQ | VH HVR2 | H2 SEQ | VH HVR3 | H3 SEQ |
|---|---|---|---|---|---|---|---|
| 5986 | 3 | GSISSSSYYWG | 12 | QIYYSGSTFYNPSLKS | 47 | ARLGHGYSYFDL | 59 |
| 6296 | 3 | GSISSSSYYWG | 12 | NIYYSGSTYYNPSLRG | 48 | ARLGHGNYNYFDL | 60 |
| 5897 | 3 | GSISWSSYYWS | 13 | SIYKSGRTYYNPSLKS | 34 | ARVGHGISYFDL | 53 |
| 5905 | 3 | GSISWSSYYWS | 13 | SIYRSGRTYYNPSLKS | 37 | ARVGHGISYFDL | 53 |
| 6311 | 3 | GSISWSSYYWS | 13 | SIYRSGRTYYNPSLKS | 37 | ARVGHGINYFDL | 55 |
| 6309 | 3 | GSISWSSYYWS | 13 | SIYRSGRTYYNPSLKS | 37 | ARVGHGINYFDL | 55 |
| 6310 | 3 | GSISWSSYYWS | 13 | SIYRSGRTYYNPSLKS | 37 | ARVGHGINYFDL | 55 |
| 6308 | 3 | GSISWSSYYWS | 13 | SIYRSGRTYYNPSLKS | 37 | ARVGHGINYFDL | 55 |
| 5990 | 3 | GSISWSSYYWS | 13 | SIYRSGRTYYNPSLKS | 37 | ARVGHGINYFDL | 55 |
| 6307 | 3 | GSISWSSYYWS | 13 | SIYRSGRTYYNPSLKG | 40 | ARVGHGINYFDL | 55 |
| 5931 | 3 | GSISWSSYYWS | 13 | STYRSGRTYYNPSLKG | 40 | ARVGHGINYFDL | 55 |
| 6298 | 3 | GSISWSSYYWS | 13 | NIYYSGSTYYNPSLKS | 44 | ARLGHGNYNYFDL | 60 |
| 5930 | 3 | GTLSGYAIS | 14 | NIIPGFGTANYAQKSQG | 38 | ARSGGTRYGMLDV | 54 |
| 5988 | 3 | GTLSGYAIS | 14 | NIIPGFGTANYAQKSQG | 38 | ARSGGTRYGMLDV | 54 |
| 6299 | 3 | GTLSGYAIS | 14 | NIIPGFGTANYAQKSQG | 38 | ARSGGTRYGMLDV | 54 |
| 6300 | 3 | GTLSGYAIS | 14 | NIIPGFGTANYAQKSQG | 38 | ARSGGTRYGMLDV | 54 |
| 6305 | 3 | GTLSGYAIS | 14 | NIIPGFGTANYAQKSQG | 38 | ARSGGTRYGMLDV | 54 |
| 5987 | 3 | GTLSGYAIS | 14 | NIIPGFGTANYAQKSQG | 38 | ARSGGTRYGMLDV | 54 |
| 6303 | 3 | GTLSGYAIS | 14 | NIIPGFGTANYAQKSQG | 38 | ARSGGTKYGMLDV | 52 |
| 6266 | 3 | GTLSGYGVS | 15 | NIIPGFGTANYAQKFQG | 29 | ARSGGTKYGMLDV | 52 |
| 6271 | 3 | GTISGYGIS | 16 | NIIPGFGTANYAQKFQG | 29 | ARSGGTKYGMLDV | 52 |
| 6297 | 3 | GPISSSSYYWG | 17 | NIYYSGSTYYNPSLRG | 48 | ARLGHGNYNYFDL | 60 |
| 6294 | 3 | GSISSSSHYWG | 18 | MIYYSGSTWYNPSLKS | 36 | ARVGHGVSYFDL | 57 |
| 5932 | 3 | GSISRGSYYWG | 19 | MIYYSGSTWYNPSLKS | 36 | ARVGHGISYFDL | 53 |

FIG. 1C

| Ab Name | Epitope bin | VH HVR1 | H1 SEQ | VH HVR2 | H2 SEQ | VH HVR3 | H3 SEQ |
|---|---|---|---|---|---|---|---|
| 6313 | 3 | GSISRGSYYWG | 19 | MIYYSGSTWYNPSLKS | 36 | ARVGHGVSYFDL | 57 |
| 6314 | 3 | GSISRGSYYWG | 19 | MIYYSGSTWYNPSLKS | 36 | ARVGHGVSYFDL | 57 |
| 6315 | 3 | GSISRGSYYWG | 19 | MIYYSGSTWYNPSLKS | 36 | ARVGHGVSYFDL | 57 |
| 5933 | 3 | GSISRGSYYWG | 19 | MIYYSGSTWYNPSLKS | 36 | ARVGHGVSYFDL | 53 |
| 6285 | 3 | GSTSSSSYYWG | 20 | SIYRSGSTYYNPSLKS | 33 | ARVGHGISYFDL | 53 |
| 6280 | 3 | GSTSSSSYYWG | 20 | SIYRSGSTYYNPSFKS | 42 | ARVGHGISYFDL | 53 |
| 6288 | 3 | GSTSSSSYYWG | 20 | SIYRSGSTYYNPSLRS | 43 | ARVGHGISYFDL | 53 |
| 5539 | 3 | YTFTGYYMH | 21 | SINPNSGGTNYAQKFQG | 49 | ARVRVRHYGMDV | 61 |

FIG. 1D

| Ab Name | Epitope bin | VL HVR1 | L1 SEQ | VL HVR2 | L2 SEQ | VL HVR3 | L3 SEQ |
|---|---|---|---|---|---|---|---|
| 5531 | 2 | RASQSISSYLN | 62 | AASSLQS | 69 | QQSYSVPLT | 75 |
| 5586 | 2 | RASQSISSYLN | 62 | AASSLQS | 69 | DESYSTPPWT | 98 |
| 5583 | 2 | RASQSVSSYLA | 63 | DASNRAT | 70 | VQRSNFPWT | 76 |
| 5532 | 2 | RASQSVSSYLA | 63 | DASNRAT | 70 | QQSSNFPFT | 77 |
| 5592 | 2 | RASQSVSSYLA | 63 | DASNRAT | 70 | QQSVNFPFT | 78 |
| 5878 | 2 | RASQSVSSYLA | 63 | DASNRAT | 70 | QQSVNFPFT | 78 |
| 5874 | 2 | RASQSVSSYLA | 63 | DASNRAT | 70 | VQRSNFPWT | 76 |
| 5875 | 2 | RASQSVSSYLA | 63 | DASNRAT | 70 | VQRSNFPWT | 76 |
| 5876 | 2 | RASQSVSSYLA | 63 | DASNRAT | 70 | VQRSNFPWT | 76 |
| 5880 | 2 | RASQSVSSYLA | 63 | DASNRAT | 70 | QQSVNFPFT | 78 |
| 5881 | 2 | RASQSVSSYLA | 63 | DASNRAT | 70 | QQSVNFPFT | 78 |
| 5260 | 3 | RASQSVGSNLA | 64 | GASTRAT | 71 | QQAVVWPPRT | 79 |
| 5572 | 3 | RASQSVGSNLA | 64 | GASTRAT | 71 | QQLYTWPPRT | 81 |
| 5536 | 3 | RASQSVGSNLA | 64 | GASTRAT | 71 | QQSYLWPPRT | 86 |
| 5571 | 3 | RASQSVSSNLA | 65 | GASTRAT | 71 | QQLILWPPRT | 80 |
| 5883 | 3 | RASQSVSSNLA | 65 | GASTRAT | 71 | QQLILWPPRT | 80 |
| 5890 | 3 | RASQSVGSNLA | 64 | GASTRAT | 71 | QQLYTWPPRT | 81 |
| 5891 | 3 | RASQSVGSNLA | 64 | GASTRAT | 71 | QQLYTWPPRT | 81 |
| 5892 | 3 | RASQSVGSNLA | 64 | GASTRAT | 71 | QQLYTWPPRT | 81 |
| 5884 | 3 | RASQSVSSNLA | 65 | GASTRAT | 71 | QQLILWPPRT | 80 |
| 6272 | 3 | RASQSVSSNLA | 65 | GASTRAT | 71 | QQLFLWPPRT | 85 |
| 6270 | 3 | RASQSVSSNLA | 65 | GASTRAT | 71 | QQLLLWPPRT | 90 |
| 6273 | 3 | RASQSVSSNIA | 66 | GASTRAT | 71 | QQLLLWPPRT | 90 |
| 6274 | 3 | RASQSVSSHLA | 67 | GASTRAT | 71 | QQLILWPPRT | 80 |
| 5893 | 3 | RASQSVGSNLA | 64 | GASTRAT | 71 | QQLYTWPPRT | 81 |
| 5887 | 3 | RASQSVSSNLA | 65 | GASTRAT | 71 | QQLILWPPRT | 80 |
| 6275 | 3 | RASQSVSSNLA | 65 | GASTRAT | 71 | QQLFLWPPRT | 85 |
| 6279 | 3 | RASQSVSSNLA | 65 | GASTRAT | 71 | QQLLLWPPRT | 90 |
| 6276 | 3 | RASQSVSSNLA | 65 | GASTRAT | 71 | QQLILWPPRT | 80 |

*FIG. 2A*

| Ab Name | Epitope bin | VL HVR1 | L1 SEQ | VL HVR2 | L2 SEQ | VL HVR3 | L3 SEQ |
|---|---|---|---|---|---|---|---|
| 5888 | 3 | RASQSVSSNLA | 65 | GASTRAT | 71 | QQLILWPPRT | 80 |
| 5894 | 3 | RASQSVGSNLA | 64 | GASTRAT | 71 | QQLYTWPPRT | 81 |
| 5543 | 3 | RASQSVSSYLA | 63 | DASNRAT | 70 | QQAYVWPPRT | 82 |
| 5643 | 3 | RASQSVSSYLA | 63 | DASNRAT | 70 | QQSLTWPPRT | 83 |
| 5644 | 3 | RASQSVSSYLA | 63 | DASKRAT | 72 | QQVYTWPPRT | 84 |
| 5896 | 3 | RASQSVSSYLA | 63 | DASNRAT | 70 | QQSLTWPPRT | 83 |
| 5902 | 3 | RASQSVSSYLA | 63 | DASKRAT | 72 | QQVYTWPPRT | 84 |
| 5903 | 3 | RASQSVSSYLA | 63 | DASKRAT | 72 | QQVYTWPPRT | 84 |
| 6290 | 3 | RASQSVSSYLA | 63 | DASKRAT | 72 | QQVYTWPPRT | 84 |
| 6291 | 3 | RASQSVSSYLA | 63 | GASKRAT | 73 | QQVYTWPPRT | 84 |
| 6293 | 3 | RASQSVSSYLA | 63 | DASKRAT | 72 | QQVYTWPPRT | 84 |
| 6289 | 3 | RASQSVSSYLA | 63 | DASNRAT | 70 | QQSLTWPPRT | 83 |
| 5747 | 3 | RASQSVSSYLA | 63 | DASNRAT | 70 | QQVYLWPPRT | 95 |
| 5982 | 3 | RASQSVSSYLA | 63 | DASNRAT | 70 | QQVYVWPPRT | 96 |
| 5985 | 3 | RASQSVSSYLA | 63 | DASNRAT | 70 | QQVYVWPPRT | 96 |
| 5983 | 3 | RASQSVSSYLA | 63 | DASNRAT | 70 | QQVYVWPPRT | 96 |
| 5984 | 3 | RASQSVSSYLA | 63 | DASNRAT | 70 | QQVYVWPPRT | 96 |
| 5986 | 3 | RASQSVSSYLA | 63 | DASNRAT | 70 | QQVYVWPPRT | 96 |
| 6296 | 3 | RASQSVSSYLA | 63 | DASNRAT | 70 | QQVYVWPPRT | 96 |
| 5897 | 3 | RASQSVSSYLA | 63 | DASNRAT | 70 | QQSLTWPPRT | 83 |
| 5905 | 3 | RASQSVSSYLA | 63 | DASKRAT | 72 | QQVYTWPPRT | 84 |
| 6311 | 3 | RASQSVSSYLA | 63 | DASNRAT | 70 | QQSLTWPPRT | 83 |
| 6309 | 3 | RASQSVSSYLA | 63 | DASNRAT | 70 | QQSITWPPRT | 93 |
| 6310 | 3 | RASQSVSSYLA | 63 | DASNRAT | 70 | QQSVTWPPRT | 94 |
| 6308 | 3 | RASQSVSSYLA | 63 | DASKRAT | 72 | QQSLVWPPRT | 92 |
| 5990 | 3 | RASRSVNSYLA | 68 | DASKRAT | 72 | QQVYTWPPRT | 84 |
| 6307 | 3 | RASQSVSSYLA | 63 | DASNRAT | 70 | QQSIVWPPRT | 91 |

*FIG. 2B*

| Ab Name | Epitope bin | VL HVR1 | L1 SEQ | VL HVR2 | L2 SEQ | VL HVR3 | L3 SEQ |
|---|---|---|---|---|---|---|---|
| 5931 | 3 | RASQSVSSYLA | 63 | DASKRAT | 72 | QQVYTWPPRT | 84 |
| 6298 | 3 | RASQSVSSYLA | 63 | DASNRAT | 70 | QQVYVWPPRT | 96 |
| 5930 | 3 | RASQSVGSNLA | 64 | GASTRAT | 71 | QQLYTWPPRT | 81 |
| 5988 | 3 | RASQSVGSNLA | 64 | GASTRAT | 71 | QQLYTWPPRT | 81 |
| 6299 | 3 | RASQSVGSNLA | 64 | GASTRAT | 71 | QQSYLWPPRT | 86 |
| 6300 | 3 | RASQSVGSNLA | 64 | GASTRAT | 71 | QQSFLWPPRT | 87 |
| 6305 | 3 | RASQSVGSNLA | 64 | GASTRAT | 71 | QQSFVWPPRT | 89 |
| 5987 | 3 | RASQSVSSNLA | 65 | GASTRAT | 71 | QQLFLWPPRT | 85 |
| 6303 | 3 | RASQSVSSNLA | 65 | GASTRAT | 71 | QQLLTWPPRT | 88 |
| 6266 | 3 | RASQSVSSNLA | 65 | GASTRAT | 71 | QQLILWPPRT | 80 |
| 6271 | 3 | RASQSVSSNLA | 65 | GASTRAT | 71 | QQLILWPPRT | 80 |
| 6297 | 3 | RASQSVSSYLA | 63 | DASNRAT | 70 | QQVYVWPPRT | 96 |
| 6294 | 3 | RASQSVSSYLA | 63 | DASKRAT | 72 | QQVYTWPPRT | 84 |
| 5932 | 3 | RASQSVSSYLA | 63 | DASKRAT | 72 | QQVYTWPPRT | 84 |
| 6313 | 3 | RASQSVSSYLA | 63 | DASNRAT | 70 | QQAYVWPPRT | 82 |
| 6314 | 3 | RASQSVSSYLA | 63 | DASNRAT | 70 | QQSIVWPPRT | 91 |
| 6315 | 3 | RASQSVSSYLA | 63 | DASKRAT | 72 | QQSLVWPPRT | 92 |
| 5933 | 3 | RASQSVSSYLA | 63 | GASKRAT | 73 | QQVYTWPPRT | 84 |
| 6285 | 3 | RASQSVSSYLA | 63 | DASSRAT | 74 | QQSLTWPPRT | 83 |
| 6280 | 3 | RASQSVSSYLA | 63 | DASNRAT | 70 | QQSLTWPPRT | 83 |
| 6288 | 3 | RASQSVSSYLA | 63 | DASNRAT | 70 | QQSLTWPPRT | 83 |
| 5539 | 3 | RASQSISSYLN | 62 | AASSLQS | 69 | QQPLSHPRT | 97 |

FIG. 2C

| Ab Name | Epitope bin | VH Sequence | VH SEQ |
|---|---|---|---|
| 5531 | 2 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGGSQWLYAPGSWFDPWGQGTLVTVSS | 99 |
| 5586 | 2 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGGSQWLYAPGSWFDPWGQGTLVTVSS | 99 |
| 5583 | 2 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGGSQWLYAPGSWFDPWGQGTLVTVSS | 99 |
| 5532 | 2 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGAGHGSYVKGWFDPWGQGTLVTVSS | 100 |
| 5592 | 2 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGAGHGSYVKGWFDPWGQGTLVTVSS | 100 |
| 5878 | 2 | EVQLLESGGGLVQPGGSLRLSCAASGFTFSSYAMSWVRQAPGKGLEWVSAISGSGISTPYADSVKGRFTISRDNSKNTLYLQMNSLRAEDTAVYYCAKGGSQWLYAPGSWFDPWGQGTLVTVSS | 101 |
| 5874 | 2 | EVQLLESGGGLVQPGGSLRLSCAASGFTFSSYAMSWVRQAPGKGLEWVSATSGSGGSTYYADSVKGRFTISRDNSKNTLYLQMDSLRAEDTAVYYCAKGGSQWLYAPGSWFDPWGQGTLVTVSS | 102 |
| 5875 | 2 | EVQLLESGGGLVQPGGSLRLSCAASGFTFSTYAMGWVRQAPGKGLEWVSATSGSGGSTYYADSVKGRFTISRDNSKNTLYLQMNSLRAEDTAVYYCAKGGSQWLYAPGSWFDPWGQGTLVTVSS | 103 |
| 5876 | 2 | EVQLLESGGGLVQPGGSLRLSCAASGFTFSSRAMGWVRQAPGKGLEWVSATSGSGGSIYYADSVKGRFTISRDNSKNTLYLQMNSLRAEDTAVYYCAKGGSQWLYAPGSWFDPWGQGTLVTVSS | 104 |
| 5880 | 2 | EVQLLESGGGLVQPGGSLRLSCAASGFTFGSYAMTWVRQAPGKGLEWVSAISGSGISTPYADSVKGRFTISRDNSKNTLYLQMNSLRAEDTAVYYCAKGAGHGSYVKGWFDPWGQGTLVTVSS | 105 |
| 5881 | 2 | EVQLLESGGGLVQPGGSLRLSCAASGFTFSSKYAMSWVRQAPGKGLEWVSAISGSGISTPYADSVKGRFTISRDNSKNTLYLQMNSLRAEDTAVYYCAKGAGHGSYVKGWFDPWGQGTLVTVSS | 106 |
| 5260 | 3 | QVQLVQSGAEVKKPGSSVKVSCKASGGTFSSYAISWVRQAPGQGLEWMGSIIPIFGTANYAQKFQGRVTITADESTSTAYMELSSLRSEDTAVYYCARSGGTKYGMLDVWGQGTMVTVSS | 107 |

FIG. 3A

| Ab Name | Epitope bin | VH Sequence | VH SEQ |
|---|---|---|---|
| 5572 | 3 | QVQLVQSGAEVKKPGSSVKVSCKASGGTFSSYAISWVRQAPGQGLEWMGSIIPIFGTANYAQKFQGRVTITADESTST AYMELSSLRSEDTAVYYCARSGGTKYGMLDVWGQGTMVTVSS | 107 |
| 5536 | 3 | QVQLVQSGAEVKKPGSSVKVSCKASGGTFSSYAISWVRQAPGQGLEWMGSIIPIFGTANYAQKFQGRVTITADESTST AYMELSSLRSEDTAVYYCARSGGTKYGMLDVWGQGTMVTVSS | 107 |
| 5571 | 3 | QVQLVQSGAEVKKPGSSVKVSCKASGGTFSSYAISWVRQAPGQGLEWMGNIIPIFGTANYAQKFQGRVTITADESTST AYMELSSLRSEDTAVYYCARSGGTKYGMLDVWGQGTMVTVSS | 108 |
| 5883 | 3 | QVQLVQSGAEVKKPGSSVKVSCKASGGTFSSYAISWVRQAPGQGLEWMGGIIPIGGGANYAQKFQGRVTITADESTST AYMELSSLRSEDTAVYYCARSGGTKYGMLDVWGQGTMVTVSS | 109 |
| 5890 | 3 | QVQLVQSGAEVKKPGSSVKVSCKASGGTFSSYAISWVRQAPGQGLEWMGNIIPGFGTANYAQKFQGRVTITADESTST AYMELSSLRSEDTAVYYCARSGGTKYGMLDVWGQGTMVTVSS | 110 |
| 5891 | 3 | QVQLVQSGAEVKKPGSSVKVSCKASGGTFSSYAISWVRQAPGQGLEWMGNIIPIFGPANYAQKFQGRVTITADESTST AYMELSSLRSEDTAVYYCARSGGTKYGMLDVWGQGTMVTVSS | 111 |
| 5892 | 3 | QVQLVQSGAEVKKPGSSVKVSCKASGGTFSSYAISWVRQAPGQGLEWMGNIIPIFGTATYAQKFQGRVTITADESTST AYMELSSLRSEDTAVYYCARSGGTKYGMLDVWGQGTMVTVSS | 112 |
| 5884 | 3 | QVQLVQSGAEVKKPGSSVKVSCKASGGTFSGYGISWVRQAPGQGLEWMGNIIPGFGTANYAQKFQGRVTITADESTST AYMELSSLRSEDTAVYYCARSGGTKYGMLDVWGQGTMVTVSS | 113 |
| 6272 | 3 | QVQLVQSGAEVKKPGSSVKVSCKASGGTFSGYGISWVRQAPGQGLEWMGNIIPGFGTANYAQKFQGRVTITADESTST AYMELSSLRSEDTAVYYCARSGGTKYGMLDVWGQGTMVTVSS | 113 |
| 6270 | 3 | QVQLVQSGAEVKKPGSSVKVSCKASGGTFSGYGISWVRQAPGQGLEWMGNIIPGFGTANYAQKFQGRVTITADESTST AYMELSSLRSEDTAVYYCARSGGTKYGMLDVWGQGTMVTVSS | 113 |
| 6273 | 3 | QVQLVQSGAEVKKPGSSVKVSCKASGGTFSGYGISWVRQAPGQGLEWMGNIIPGFGTANYAQKFQGRVTITADESTST AYMELSSLRSEDTAVYYCARSGGTKYGMLDVWGQGTMVTVSS | 113 |
| 6274 | 3 | QVQLVQSGAEVKKPGSSVKVSCKASGGTFSGYGISWVRQAPGQGLEWMGNIIPGFGTANYAQKFQGRVTITADESTST AYMELSSLRSEDTAVYYCARSGGTKYGMLDVWGQGTMVTVSS | 113 |

FIG. 3B

| Ab Name | Epitope bin | VH Sequence | VH SEQ |
|---|---|---|---|
| 5893 | 3 | QVQLVQSGAEVKKPGSSVKVSCKASGGTFRGYAISWVRQAPGQGLEWMGNIIPGFGTANYAQKFQGRVTITADESTST AYMELSSLRSEDTAVYYCARSGGTKYGMLDVWGQGTMVTVSS | 114 |
| 5887 | 3 | QVQLVQSGAEVKKPGSSVKVSCKASGGTFRGYAISWVRQAPGQGLEWMGNIIPGFGTANYAQKFQGRVTITADESTST AYMELSSLRSEDTAVYYCARSGGTKYGMLDVWGQGTMVTVSS | 114 |
| 6275 | 3 | QVQLVQSGAEVKKPGSSVKVSCKASGGTFRGYAISWVRQAPGQGLEWMGNIIPGFGTANYAQKFQGRVTITADESTST AYMELSSLRSEDTAVYYCARSGGTKYGMLDVWGQGTMVTVSS | 114 |
| 6279 | 3 | QVQLVQSGAEVKKPGSSVKVSCKASGGTFRGYAISWVRQAPGQGLEWMGNIIPGFGTANYAQKFQGRVTITADESTST AYMELSSLRSEDTAVYYCARSGGTKYGMLDVWGQGTMVTVSS | 114 |
| 6276 | 3 | QVQLVQSGAEVKKPGSSVKVSCKASGGTFRGYAISWVRQAPGQGLEWMGNIIPGLSTANYAQKFQGRVTITADESTST AYMELSSLRSEDTAVYYCARSGGTKYGMLDVWGQGTMVTVSS | 115 |
| 5888 | 3 | QVQLVQSGAEVKKPGSSVKVSCKASGGTFWKYAISWVRQAPGQGLEWMGNIIPGFGTANYAQKFQGRVTITADESTST AYMELSSLRSEDTAVYYCARSGGTKYGMLDVWGQGTMVTVSS | 116 |
| 5894 | 3 | QVQLVQSGAEVKKPGSSVKVSCKASGGTFSGYAISWVRQAPGQGLEWMGNIIPGFGTANYAQKFRGRVTITADESTST AYMELSSLRSEDTAVYYCARSGGTKYGMLDVWGQGTMVTVSS | 117 |
| 5543 | 3 | QLQLQESGPGLVKPSETLSLTCTVSGGSISISSSSYYWGWIRQPPGKGLEWIGSIYYSGSTYYNPSLKSRVTISVDTSKN QFSLKLSSVTAADTAVYYCARVGHGISYFDLWGRGTLVTVSS | 118 |
| 5643 | 3 | QLQLQESGPGLVKPSETLSLTCTVSGGSISLTCTVSGGSISSSSYYWGWIRQPPGKGLEWIGSIYYSGSTYYNPSLKSRVTISVDTSKN QFSLKLSSVTAADTAVYYCARVGHGISYFDLWGRGTLVTVSS | 118 |
| 5644 | 3 | QLQLQESGPGLVKPSETLSLTCTVSGGSISSSSYYWGWIRQPPGKGLEWIGSIYYSGSTYYNPSLKSRVTISVDTSKN QFSLKLSSVTAADTAVYYCARVGHGISYFDLWGRGTLVTVSS | 118 |
| 5896 | 3 | QLQLQESGPGLVKPSETLSLTCTVSGGSISSSSYYWGWIRQPPGKGLEWIGSIYRSGSTYYNPSLKSRVTISVDTSKN QFSLKLSSVTAADTAVYYCARVGHGISYFDLWGRGTLVTVSS | 119 |
| 5902 | 3 | QLQLQESGPGLVKPSETLSLTCTVSGGSISSSSYYWGWIRQPPGKGLEWIGSIYRSGSTWYNPSLKSRVTISVDTSKN QFSLKLSSVTAADTAVYYCARVGHGISYFDLWGRGTLVTVSS | 120 |
| 5903 | 3 | QLQLQESGPGLVKPSETLSLTCTVSGGSISSSSYYWGWIRQPPGKGLEWIGMIYYSGSTWYNPSLKSRVTISVDTSKN QFSLKLSSVTAADTAVYYCARVGHGISYFDLWGRGTLVTVSS | 121 |

FIG. 3C

| Ab Name | Epitope bin | VH Sequence | VH SEQ |
|---|---|---|---|
| 6290 | 3 | QLQLQESGPGLVKPSETLSLTCTVSGGSISSSSYYWGWIRQPPGKGLEWIGMIYYSGSTWYNPSLKSRVTISVDTSKN QFSLKLSSVTAADTAVYYCARVGLGVSYFDLWGRGTLVTVSS | 122 |
| 6291 | 3 | QLQLQESGPGLVKPSETLSLTCTVSGGSISSSSYYWGWIRQPPGKGLEWIGMIYYSGSTWYNPSLKSRVTISVDTSKN QFSLKLSSVTAADTAVYYCARVGHGVSYFDLWGRGTLVTVSS | 123 |
| 6293 | 3 | QLQLQESGPGLVKPSETLSLTCTVSGGSISSSSYYWGWIRQPPGKGLEWIGMIYYSGSTWYNPSLKSRVTISVDTSKN QFSLKLSSVTAADTAVYYCARVGHGVSYFDLWGRGTLVTVSS | 124 |
| 6289 | 3 | QLQLQESGPGLVKPSETLSLTCTVSGGSISSSSYYWGWIRQPPGKGLEWIGSIYRSGSTYYNPSLRSRVTISVDTSKN QFSLKLSSVTAADTAVYYCVRVGHGISYFDLWGRGTLVTVSS | 125 |
| 5747 | 3 | QLQLQESGPGLVKPSETLSLTCTVSGGSISSSSYYWGWIRQPPGKGLEWIGSIYRSGSTYYNPSLRSRVTISVDTSKN QFSLKLSSVTAADTAVYYCARLGHGYSYFDLWGRGTLVTVSS | 126 |
| 5982 | 3 | QLQLQESGPGLVKPSETLSLTCTVSGGSISSSSYYWGWIRQPPGKGLEWIGNIYYSGSTYYNPSLKSRVTISVDTSKN QFSLKLSSVTAADTAVYYCARLGHGYSYFDLWGRGTLVTVSS | 126 |
| 5985 | 3 | QLQLQESGPGLVKPSETLSLTCTVSGGSISSSSYYWGWIRQPPGKGLEWIGNIYYSGSTYYNPSLKSRVTISVDTSKN QFSLKLSSVTAADTAVYYCARLGHGYNYFDLWGRGTLVTVSS | 127 |
| 5983 | 3 | QLQLQESGPGLVKPSETLSLTCTVSGGSISSSSYYWGWIRQPPGKGLEWIGNIYYSGSTYYNPSLRSRVTISVDTSKN QFFLKLSSVTAADTAVYYCARLGHGYNYFDLWGRGTLVTVSS | 128 |
| 5984 | 3 | QLQLQESGPGLVKPSETLSLTCTVSGGSISSSSYYWGWIRQPPGKGLEWIGNIYYSGSTYYNPSLKSRVTISVDTSKN QFSLKLSSVTAADTAVYYCARLGHGYNYFDLWGRGTLVTVSS | 129 |
| 5986 | 3 | QLQLQESGPGLVKPSETLSLTCTVSGGSISSSSYYWGWIRQPPGKGLEWIGQIYYSGSTFYNPSLKSRVTISVDTSKN QFSLKLSSVTAADTAVYYCARLGHGYSYFDLWGRGTLVTVSS | 130 |
| 6296 | 3 | QLQLQESGPGLVKPSETLSLTCTVSGGSISSSSYYWGWIRQPPGKGLEWIGNIYYSGSTYYNPSLRGRVTISVDTSKN QFSLKLSSVTAADTAVYYCARVGHGYNYFDLWGRGTLVTVSS | 131 |
| 5897 | 3 | QLQLQESGPGLVKPSETLSLTCTVSGGSISWSSYYWSWIRQPPGKGLEWIGSIYKSGRTYYNPSLKSRVTISVDTSKN QFSLKLSSVTAADTAVYYCARVGHGISYFDLWGRGTLVTVSS | 132 |
| 5905 | 3 | QLQLQESGPGLVKPSETLSLTCTVSGGSISWSSYYWSWIRQPPGKGLEWIGSIYRSGRTYYNPSLKSRVTISVDTSKN QFSLKLSSVTAADTAVYYCARVGHGISYFDLWGRGTLVTVSS | 133 |

FIG. 3D

| Ab Name | Epitope bin | VH Sequence | VH SEQ |
|---|---|---|---|
| 6311 | 3 | QLQLQESGPGLVKPSETLSLTCTVSGGSISWSSYYWSWIRQPPGKGLEWIGSIYRSGRTYYNPSLKSRVTISVDTSKN QFSLKLSSVTAADTAVYYCARVGHGINYFDLWGRGTLVTVSS | 134 |
| 6309 | 3 | QLQLQESGPGLVKPSETLSLTCTVSGGSISWSSYYWSWIRQPPGKGLEWIGSIYRSGRTYYNPSLKSRVTISVDTSKN QFSLKLSSVTAADTAVYYCARVGHGINYFDLWGRGTLVTVSS | 134 |
| 6310 | 3 | QLQLQESGPGLVKPSETLSLTCTVSGGSISWSSYYWSWIRQPPGKGLEWIGSIYRSGRTYYNPSLKSRVTISVDTSKN QFSLKLSSVTAADTAVYYCARVGHGINYFDLWGRGTLVTVSS | 134 |
| 6308 | 3 | QLQLQESGPGLVKPSETLSLTCTVSGGSISWSSYYWSWIRQPPGKGLEWIGSIYRSGRTYYNPSLKSRVTISVDTSKN QFSLKLSSVTAADTAVYYCARVGHGINYFDLWGRGTLVTVSS | 134 |
| 5990 | 3 | QLQLQESGPGLVKPSETLSLTCTVSGGSISWSSYYWSWIRQPPGKGLEWIGSIYRSGRTYYNPSLKSRVTISVDTSKN QFSLKLSSVTAADTAVYYCARVGHGINYFDLWGRGTLVTVSS | 134 |
| 6307 | 3 | QLQLQESGPGLVKPSETLSLTCTVSGGSISWSSYYWSWIRQPPGKGLEWIGSIYRSGRTYYNPSLKGRVTISVDTSKN QFSLKLSSVTAADTAVYYCARVGHGINYFDLWGRGTLVTVSS | 135 |
| 5931 | 3 | QLQLQESGPGLVKPSETLSLTCTVSGGSISWSSYYWSWIRQPPGKGLEWIGSIYRSGRTYYNPSLKSRVTISVDTSKN QFSLKLSSVTAADTAVYYCARVGHGINYFDLWGRGTLVTVSS | 135 |
| 6298 | 3 | QLQLQESGPGLVKPSETLSLTCTVSGGSISWSSYYWSWIRQPPGKGLEWIGNIYYSGSTYYNPSLKSRVTISVDTSKN QFSLKLSSVTAADTAVYYCARLGHGYNYFDLWGRGTLVTVSS | 136 |
| 5930 | 3 | QVQLVQSGAEVKKPGSSVKVSCKASGGTLSGYAISWVRQAPGQGLEWMGNIIPGFGTANYAQKSQGRVTITADESTST AYMELSSLRSEDTAVYYCARSGGTRYGMLDVWGQGTMVTVSS | 137 |
| 5988 | 3 | QVQLVQSGAEVKKPGSSVKVSCKASGGTLSGYAISWVRQAPGQGLEWMGNIIPGFGTANYAQKSQGRVTITADESTST AYMELSSLRSEDTAVYYCARSGGTRYGMLDVWGQGTMVTVSS | 137 |
| 6299 | 3 | QVQLVQSGAEVKKPGSSVKVSCKASGGTLSGYAISWVRQAPGQGLEWMGNIIPGFGTANYAQKSQGRVTITADESTST AYMELSSLRSEDTAVYYCARSGGTRYGMLDVWGQGTMVTVSS | 137 |
| 6300 | 3 | QVQLVQSGAEVKKPGSSVKVSCKASGGTLSGYAISWVRQAPGQGLEWMGNIIPGFGTANYAQKSQGRVTITADESTST AYMELSSLRSEDTAVYYCARSGGTRYGMLDVWGQGTMVTVSS | 137 |
| 6305 | 3 | QVQLVQSGAEVKKPGSSVKVSCKASGGTLSGYAISWVRQAPGQGLEWMGNIIPGFGTANYAQKSQGRVTITADESTST AYMELSSLRSEDTAVYYCARSGGTRYGMLDVWGQGTMVTVSS | 137 |

FIG. 3E

| Ab Name | Epitope bin | VH Sequence | VH SEQ |
|---|---|---|---|
| 5987 | 3 | QVQLVQSGAEVKKPGSSVKVSCKASGGTLSGYAISWVRQAPGQGLEWMGNIIPGFGTANYAQKSQGRVTITADESTST AYMELSSLRSEDTAVYYCARSGGTRYGMLDVWGQGTMVTVSS | 137 |
| 6303 | 3 | QVQLVQSGAEVKKPGSSVKVSCKASGGTLSGYAISWVRQAPGQGLEWMGNIIPGFGTANYAQKSQGRVTITADESTST AYMELSSLRSEDTAVYYCARSGGTRYGMLDVWGQGTMVTVSS | 137 |
| 6266 | 3 | QVQLVQSGAEVKKPGSSVKVSCKASGGTLSGYGVSWVRQAPGQGLEWMGNIIPGFGTANYAQKFQGRVTITADESTST AYMELSSLRSEDTAVYYCARSGGTKYGMLDVWGQGTMVTVSS | 138 |
| 6271 | 3 | QVQLVQSGAEVKKPGSSVKVSCKASGGTISGYGISWVRQAPGQGLEWMGNIIPGFGTANYAQKFQGRVTITADESTST AYMELSSLRSEDTAVYYCARSGGTKYGMLDVWGQGTMVTVSS | 139 |
| 6297 | 3 | QLQLQESGPGLVKPSETLSLTCTVSGGPISSSSYYWGWIRQPPGKGLEWIGNIYYSGSTYYNPSLRGRVTISVDTSKN QFSLKLSSVTAADTAVYYCARLGHGYNYFDLWGRGTLVTVSS | 140 |
| 6294 | 3 | QLQLQESGPGLVKPSETLSLTCTVSGGSISSSSHYWGWIRQPPGKGLEWIGMIYYSGSTWYNPSLKSRVTISVDTSKN QFSLKLSSVTAADTAVYYCARVGHGVSYFDLWGRGTLVTVSS | 141 |
| 5932 | 3 | QLQLQESGPGLVKPSETLSLTCTVSGGSISRGSYYWGWIRQPPGKGLEWIGMIYYSGSTWYNPSLKSRVTISVDTSKN QFSLKLSSVTAADTAVYYCARVGHGISYFDLWGRGTLVTVSS | 142 |
| 6313 | 3 | QLQLQESGPGLVKPSETLSLTCTVSGGSISRGSYYWGWIRQPPGKGLEWIGMIYYSGSTWYNPSLKSRVTISVDTSKN QFSLKLSSVTAADTAVYYCARVGHGVSYFDLWGRGTLVTVSS | 143 |
| 6314 | 3 | QLQLQESGPGLVKPSETLSLTCTVSGGSISRGSYYWGWIRQPPGKGLEWIGMIYYSGSTWYNPSLKSRVTISVDTSKN QFSLKLSSVTAADTAVYYCARVGHGVSYFDLWGRGTLVTVSS | 143 |
| 6315 | 3 | QLQLQESGPGLVKPSETLSLTCTVSGGSISRGSYYWGWIRQPPGKGLEWIGMIYYSGSTWYNPSLKSRVTISVDTSKN QFSLKLSSVTAADTAVYYCARVGHGVSYFDLWGRGTLVTVSS | 143 |
| 5933 | 3 | QLQLQESGPGLVKPSETLSLTCTVSGGSTSSSSYYWGWIRQPPGKGLEWIGMIYYSGSTWYNPSLKSRVTISVDTSKN QFSLKLSSVTAADTAVYYCARVGHGISYFDLWGRGTLVTVSS | 144 |
| 6285 | 3 | QLQLQESGPGLVKPSETLSLTCTVSGGSTSSSSYYWGWIRQPPGKGLEWIGSIYRSGSTYYNPSFKSRVTISVDTSKN QFSLKLSSVTAADTAVYYCARVGHGISYFDLWGRGTLVTVSS | 145 |
| 6280 | 3 | QLQLQESGPGLVKPSETLSLTCTVSGGSTSSSSYYWGWIRQPPGKGLEWIGSIYRSGSTYYNPSFKSRVTISVDTSKN QFSLKLSSVTAADTAVYYCARVGHGISYFDLWGRGTLVTVSS | 145 |

FIG. 3F

| Ab Name | Epitope bin | VH Sequence | VH SEQ |
|---|---|---|---|
| 6288 | 3 | QLQLQESGPGLVKPSETLSLTCTVSGGSTSSSSYYWGWIRQPPGKGLEWIGSIYRSGSTYYNPSLRSRVTISVDTSKN QFSLKLSSVTAADTAVYYCARVGHGISYFDLWGRGTLVTVSS | 146 |
| 5539 | 3 | QVQLVQSGAEVKKPGASVKVSCKASGYTFTGYYMHWVRQAPGQGLEWMGSINPNSGGTNYAQKFQGRVTMTRDTSIST AYMELSRLRSDDTAVYYCARVRVRHYGMDVWGQGTTVTVSS | 147 |

*FIG. 3G*

| Ab Name | Epitope bin | VL Protein | VL SEQ |
|---|---|---|---|
| 5531 | 2 | DIQMTQSPSSLSASVGDRVTITCRASQSISSYLNWYQQKPGKAPKLLIYAASSLQSGVPSRFSGSGSGTDFTL TISSLQPEDFATYYCQQSYSVPLTFGGGTKVEIK | 148 |
| 5586 | 2 | DIQMTQSPSSLSASVGDRVTITCRASQSISSYLNWYQQKPGKAPKLLIYAASSLQSGVPSRFSGSGSGTDFTL TISSLQPEDFATYYCDESYSTPPWTFGGGTKVEIK | 149 |
| 5583 | 2 | EIVLTQSPATLSLSPGERATLSCRASQSVSSYLAWYQQKPGQAPRLLIYDASNRATGIPARFSGSGSGTDFTL TISSLEPEDFAVYYCVQRSNFPWTFGGGTKVEIK | 150 |
| 5532 | 2 | EIVLTQSPATLSLSPGERATLSCRASQSVSSYLAWYQQKPGQAPRLLIYDASNRATGIPARFSGSGSGTDFTL TISSLEPEDFAVYYCQQSNFPFTFGGGTKVEIK | 151 |
| 5592 | 2 | EIVLTQSPATLSLSPGERATLSCRASQSVSSYLAWYQQKPGQAPRLLIYDASNRATGIPARFSGSGSGTDFTL TISSLEPEDFAVYYCQQSVNFPFTFGGGTKVEIK | 152 |
| 5878 | 2 | EIVLTQSPATLSLSPGERATLSCRASQSVSSYLAWYQQKPGQAPRLLIYDASNRATGIPARFSGSGSGTDFTL TISSLEPEDFAVYYCQQSVNFPFTFGGGTKVEIK | 152 |
| 5874 | 2 | EIVLTQSPATLSLSPGERATLSCRASQSVSSYLAWYQQKPGQAPRLLIYDASNRATGIPARFSGSGSGTDFTL TISSLEPEDFAVYYCVQRSNFPWTFGGGTKVEIK | 150 |
| 5875 | 2 | EIVLTQSPATLSLSPGERATLSCRASQSVSSYLAWYQQKPGQAPRLLIYDASNRATGIPARFSGSGSGTDFTL TISSLEPEDFAVYYCVQRSNFPWTFGGGTKVEIK | 150 |
| 5876 | 2 | EIVLTQSPATLSLSPGERATLSCRASQSVSSYLAWYQQKPGQAPRLLIYDASNRATGIPARFSGSGSGTDFTL TISSLEPEDFAVYYCQQSNFPFTFGGGTKVEIK | 152 |
| 5880 | 2 | EIVLTQSPATLSLSPGERATLSCRASQSVSSYLAWYQQKPGQAPRLLIYDASNRATGIPARFSGSGSGTDFTL TISSLEPEDFAVYYCQQSVNFPFTFGGGTKVEIK | 152 |
| 5881 | 2 | EIVLTQSPATLSLSPGERATLSCRASQSVSSYLAWYQQKPGQAPRLLIYDASNRATGIPARFSGSGSGTDFTL TISSLEPEDFAVYYCQQSVNFPFTFGGGTKVEIK | 152 |
| 5260 | 3 | EIVMTQSPATLSVSPGERATLSCRASQSVGSNLAWYQQKPGQAPRLLIYGASTRATGIPARFSGSGSGTDFTL TISSLQSEDFAVYYCQQAVVWPPRTFGGGTKVEIK | 153 |
| 5572 | 3 | EIVMTQSPATLSVSPGERATLSCRASQSVGSNLAWYQQKPGQAPRLLIYGASTRATGIPARFSGSGSGTEFTL TISSLQSEDFAVYYCQQLYTWPPRTFGGGTKVEIK | 154 |

FIG. 4A

| Ab Name | Epitope bin | VL Protein | VL SEQ |
|---|---|---|---|
| 5536 | 3 | EIVMTQSPATLSVSPGERATLSCRASQSVGSNLAWYQQKPGQAPRLLIYGASTRATGIPARFSGSGSGTEFTLTISSLQSEDFAVYYCQQSYLWPPRTFGGGTKVEIK | 155 |
| 5571 | 3 | EIVMTQSPATLSVSPGERATLSCRASQSVSSNLAWYQQKPGQAPRLLIYGASTRATGIPARFSGSGSGTEFTLTISSLQSEDFAVYYCQQLILWPPRTFGGGTKVEIK | 156 |
| 5883 | 3 | EIVMTQSPATLSVSPGERATLSCRASQSVSSNLAWYQQKPGQAPRLLIYGASTRATGIPARFSGSGSGTEFTLTISSLQSEDFAVYYCQQLILWPPRTFGGGTKVEIK | 156 |
| 5890 | 3 | EIVMTQSPATLSVSPGERATLSCRASQSVGSNLAWYQQKPGQAPRLLIYGASTRATGIPARFSGSGSGTEFTLTISSLQSEDFAVYYCQQLYTWPPRTFGGGTKVEIK | 154 |
| 5891 | 3 | EIVMTQSPATLSVSPGERATLSCRASQSVGSNLAWYQQKPGQAPRLLIYGASTRATGIPARFSGSGSGTEFTLTISSLQSEDFAVYYCQQLYTWPPRTFGGGTKVEIK | 154 |
| 5892 | 3 | EIVMTQSPATLSVSPGERATLSCRASQSVGSNLAWYQQKPGQAPRLLIYGASTRATGIPARFSGSGSGTEFTLTISSLQSEDFAVYYCQQLYTWPPRTFGGGTKVEIK | 154 |
| 5884 | 3 | EIVMTQSPATLSVSPGERATLSCRASQSVSSNLAWYQQKPGQAPRLLIYGASTRATGIPARFSGSGSGTEFTLTISSLQSEDFAVYYCQQLILWPPRTFGGGTKVEIK | 156 |
| 6272 | 3 | EIVMTQSPATLSVSPGERATLSCRASQSVGSNLAWYQQKPGQAPRLLIYGASTRATGIPARFSGSGSGTEFTLTISSLQSEDFAVYYCQQLFLWPPRTFGGGTKVEIK | 157 |
| 6270 | 3 | EIVMTQSPATLSVSPGERATLSCRASQSVSSNLAWYQQKPGQAPRLLIYGASTRATGIPARFSGSGSGTEFTLTISSLQSEDFAVYYCQQLLLWPPRTFGGGTKVEIK | 158 |
| 6273 | 3 | EIVMTQSPATLSVSPGERATLSCRASQSVSSNIAWYQQKPGQAPRLLIYGASTRATGIPARFSGSGSGTEFTLTISSLQSEDFAVYYCQQLILWPPRTFGGGTKVEIK | 159 |
| 6274 | 3 | EIVMTQSPATLSVSPGERATLSCRASQSVSSHLAWYQQKPGQAPRLLIYGASTRATGIPARFSGSGSGTEFTLTISSLQSEDFAVYYCQQLILWPPRTFGGGTKVEIK | 160 |
| 5893 | 3 | EIVMTQSPATLSVSPGERATLSCRASQSVGSNLAWYQQKPGQAPRLLIYGASTRATGIPARFSGSGSGTEFTLTISSLQSEDFAVYYCQQLYTWPPRTFGGGTKVEIK | 154 |
| 5887 | 3 | EIVMTQSPATLSVSPGERATLSCRASQSVSSNLAWYQQKPGQAPRLLIYGASTRATGIPARFSGSGSGTEFTLTISSLQSEDFAVYYCQQLILWPPRTFGGGTKVEIK | 156 |

FIG. 4B

| Ab Name | Epitope bin | VL Protein | VL SEQ |
|---|---|---|---|
| 6275 | 3 | EIVMTQSPATLSVSPGERATLSCRASQSVSSNLAWYQQKPGQAPRLLIYGASTRATGIPARFSGSGSGTEFTL<br>TISSLQSEDFAVYYCQQLFLWPPRTFGGGTKVEIK | 157 |
| 6279 | 3 | EIVMTQSPATLSVSPGERATLSCRASQSVSSNLAWYQQKPGQAPRLLIYGASTRATGIPARFSGSGSGTEFTL<br>TISSLQSEDFAVYYCQQLLLWPPRTFGGGTKVEIK | 158 |
| 6276 | 3 | EIVMTQSPATLSVSPGERATLSCRASQSVSSNLAWYQQKPGQAPRLLIYGASTRATGIPARFSGSGSGTEFTL<br>TISSLQSEDFAVYYCQQLILWPPRTFGGGTKVEIK | 156 |
| 5888 | 3 | EIVMTQSPATLSVSPGERATLSCRASQSVSSNLAWYQQKPGQAPRLLIYGASTRATGIPARFSGSGSGTEFTL<br>TISSLQSEDFAVYYCQQLILWPPRTFGGGTKVEIK | 156 |
| 5894 | 3 | EIVMTQSPATLSVSPGERATLSCRASQSVGSNLAWYQQKPGQAPRLLIYGASTRATGIPARFSGSGSGTEFTL<br>TISSLQSEDFAVYYCQQLYTWPPRTFGGGTKVEIK | 154 |
| 5543 | 3 | EIVLTQSPATLSLSPGERATLSCRASQSVSSYLAWYQQKPGQAPRLLIYGASTRATGIPARFSGSGSGTDFTL<br>TISSLEPEDFAVYYCQQAYVWPPRTFGGGTKVEIK | 161 |
| 5643 | 3 | EIVLTQSPATLSLSPGERATLSCRASQSVSSYLAWYQQKPGQAPRLLIYDASNRATGIPARFSGSGSGTDFTL<br>TISSLEPEDFAVYYCQQVYTWPPRTFGGGTKVEIK | 162 |
| 5644 | 3 | EIVLTQSPATLSLSPGERATLSCRASQSVSSYLAWYQQKPGQAPRLLIYDASKRATGIPARFSGSGSGTDFTL<br>TISSLEPEDFAVYYCQQVYTWPPRTFGGGTKVEIK | 163 |
| 5896 | 3 | EIVLTQSPATLSLSPGERATLSCRASQSVSSYLAWYQQKPGQAPRLLIYDASNRATGIPARFSGSGSGTDFTL<br>TISSLEPEDFAVYYCQQSLTWPPRTFGGGTKVEIK | 162 |
| 5902 | 3 | EIVLTQSPATLSLSPGERATLSCRASQSVSSYLAWYQQKPGQAPRLLIYDASKRATGIPARFSGSGSGTDFTL<br>TISSLEPEDFAVYYCQQVYTWPPRTFGGGTKVEIK | 163 |
| 5903 | 3 | EIVLTQSPATLSLSPGERATLSCRASQSVSSYLAWYQQKPGQAPRLLIYDASKRATGIPARFSGSGSGTDFTL<br>TISSLEPEDFAVYYCQQVYTWPPRTFGGGTKVEIK | 163 |
| 5903* | 3 | EIVLTQSPATLSLSPGERATLSCRASQSVSSYLAWYQQKPGQAPRLLIYDASKRATGIPARFSGSGSGTDFTL<br>TISSLEPEDFAVYYCQQVYTWPPRTFGGGTKVEIK | 163 |
| 6290 | 3 | EIVLTQSPATLSLSPGERATLSCRASQSVSSYLAWYQQKPGQAPRLLIYDASKRATGIPARFSGSGSGTDFTL<br>TISSLEPEDFAVYYCQQVYTWPPRTFGGGTKVEIK | 163 |

FIG. 4C

| Ab Name | Epitope bin | VL Protein | VL SEQ |
|---|---|---|---|
| 6291 | 3 | EIVLTQSPATLSLSPGERATLSCRASQSVSSYLAWYQQKPGQAPRLLIYGASKRATGIPARFSGSGSGTDFTL TISSLEPEDFAVYYCQQVYTWPPRTFGGGTKVEIK | 164 |
| 6293 | 3 | EIVLTQSPATLSLSPGERATLSCRASQSVSSYLAWYQQKPGQAPRLLIYDASKRATGIPARFSGSGSGTDFTL TISSLEPEDFAVYYCQQVYTWPPRTFGGGTKVEIK | 163 |
| 6289 | 3 | EIVLTQSPATLSLSPGERATLSCRASQSVSSYLAWYQQKPGQAPRLLIYDASNRATGIPARFSGSGSGTDFTL TISSLEPEDFAVYYCQQSLTWPPRTFGGGTKVEIK | 162 |
| 5747 | 3 | EIVLTQSPATLSLSPGERATLSCRASQSVSSYLAWYQQKPGQAPRLLIYDASNRATGIPARFSGSGSGTDFTL TISSLEPEDFAVYYCQQVYLWPPRTFGGGTKVEIK | 165 |
| 5982 | 3 | EIVLTQSPATLSLSPGERATLSCRASQSVSSYLAWFQQKPGQAPRLLIYDASNRATGIPARFSGSGSGTDFTL TISSLEPEDFAVYYCQQVYTWPPRTFGGGTKVEIK | 166 |
| 5985 | 3 | EIVLTQSPATLSLSPGERATLSCRASQSVSSYLAWFQQKPGQAPRLLIYDASNRATGIPARFSGSGSGTDFTL TISSLEPEDFAVYYCQQVYTWPPRTFGGGTKVEIK | 166 |
| 5983 | 3 | EIVLTQSPATLSLSPGERATLSCRASQSVSSYLAWFQQKPGQAPRLLIYDASNRATGIPARFSGSGSGTDFTL TISSLEPEDFAVYYCQQVYTWPPRTFGGGTKVEIK | 166 |
| 5984 | 3 | EIVLTQSPATLSLSPGERATLSCRASQSVSSYLAWFQQKPGQAPRLLIYDASNRATGIPARFSGSGSGTDFTL TISSLEPEDFAVYYCQQVYTWPPRTFGGGTKVEIK | 166 |
| 5986 | 3 | EIVLTQSPATLSLSPGERATLSCRASQSVSSYLAWFQQKPGQAPRLLIYDASNRATGIPARFSGSGSGTDFTL TISSLEPEDFAVYYCQQVYTWPPRTFGGGTKVEIK | 166 |
| 6296 | 3 | EIVLTQSPATLSLSPGERATLSCRASQSVSSYLAWYQQKPGQAPRLLIYDASNRATGIPARFSGSGSGTDFTL TISSLEPEDFAVYYCQQVYTWPPRTFGGGTKVEIK | 166 |
| 5897 | 3 | EIVLTQSPATLSLSPGERATLSCRASQSVSSYLAWYQQKPGQAPRLLIYDASNRATGIPARFSGSGSGTDFTL TISSLEPEDFAVYYCQQSLTWPPRTFGGGTKVEIK | 162 |
| 5905 | 3 | EIVLTQSPATLSLSPGERATLSCRASQSVSSYLAWYQQKPGQAPRLLIYDASKRATGIPARFSGSGSGTDFTL TISSLEPEDFAVYYCQQVYTWPPRTFGGGTKVEIK | 163 |
| 6311 | 3 | EIVLTQSPATLSLSPGERATLSCRASQSVSSYLAWYQQKPGQAPRLLIYDASNRATGIPARFSGSGSGTDFTL TISSLEPEDFAVYYCQQSLTWPPRTFGGGTKVEIK | 162 |

FIG. 4D

| Ab Name | Epitope bin | VL Protein | VL SEQ |
|---|---|---|---|
| 6309 | 3 | EIVLTQSPATLSLSPGERATLSCRASQSVSSYLAWYQQKPGQAPRLLIYDASNRATGIPARFSGSGSGTDFTL TISSLEPEDFAVYYCQQSITWPPRTFGGGTKVEIK | 167 |
| 6310 | 3 | EIVLTQSPATLSLSPGERATLSCRASQSVSSYLAWYQQKPGQAPRLLIYDASNRATGIPARFSGSGSGTDFTL TISSLEPEDFAVYYCQQSVTWPPRTFGGGTKVEIK | 168 |
| 6308 | 3 | EIVLTQSPATLSLSPGERATLSCRASQSVSSYLAWYQQKPGQAPRLLIYDASKRATGIPARFSGSGSGTDFTL TISSLEPEDFAVYYCQQSLVWPPRTFGGGTKVEIK | 169 |
| 5990 | 3 | EIVLTQSPATLSLSPGERATLSCRASRSVNSYLAWYQQKPGQAPRLLIYDASKRATGIPARFSGSGSGTDFTL TISSLEPEDFAVYYCQQVYTWPPRTFGGGTKVEIK | 170 |
| 6307 | 3 | EIVLTQSPATLSLSPGERATLSCRASQSVSSYLAWYQQKPGQAPRLLIYDASNRATGIPARFSGSGSGTDFTL TISSLEPEDFAVYYCQQSIVWPPRTFGGGTKVEIK | 171 |
| 5931 | 3 | EIVLTQSPATLSLSPGERATLSCRASQSVSSYLAWYQQKPGQAPRLLIYDASKRATGIPARFSGSGSGTDFTL TISSLEPEDFAVYYCQQVYTWPPRTFGGGTKVEIK | 163 |
| 6298 | 3 | EIVMTQSPATLSLSPGERATLSCRASQSVSSYLAWFQQKPGQAPRLLIYDASNRATGIPARFSGSGSGTDFTL TISSLEPEDFAVYYCQQVYWPPRTFGGGTKVEIK | 166 |
| 5930 | 3 | EIVMTQSPATLSVSPGERATLSCRASQSVGSNLAWYQQKPGQAPRLLIYGASTRATGIPARFSGSGSGTEFTL TISSLQSEDFAVYYCQQLYTWPPRTFGGGTKVEIK | 154 |
| 5988 | 3 | GIVMTQSPATLSVSPGERATLSCRASQSVGSNLAWYQQKPGQAPRLLIYGASTRATGIPARFSGSGSGTEFTL TISSLQSEDFAVYYCQQLYTWPPRTFGGGTKVEIK | 172 |
| 6299 | 3 | EIVMTQSPATLSVSPGERATLSCRASQSVGSNLAWYQQKPGQAPRLLIYGASTRATGIPARFSGSGSGTEFTL TISSLQSEDFAVYYCQQSYLWPPRTFGGGTKVEIK | 155 |
| 6300 | 3 | EIVLTQSPATLSVSPGERATLSCRASQSVGSNLAWYQQKPGQAPRLLIYGASTRATGIPARFSGSGSGTEFTL TISSLQSEDFAVYYCQQSFLWPPRTFGGGTKVEIK | 173 |
| 6305 | 3 | EIVLTQSPATLSVSPGERATLSCRASQSVGSNLAWYQQKPGQAPRLLIYGASTRATGIPARFSGSGSGTEFTL TISSLQSEDFAVYYCQQLFLWPPRTFGGGTKVEIK | 174 |
| 5987 | 3 | EIVMTQSPATLSVSPGERATLSCRASQSVSSNLAWYQQKPGQAPRLLIYGASTRATGIPARFSGSGSGTEFTL TISSLQSEDFAVYYCQQLFLWPPRTFGGGTKVEIK | 157 |

FIG. 4E

| Ab Name | Epitope bin | VL Protein | VL SEQ |
|---|---|---|---|
| 6303 | 3 | EIVMTQSPATLSVSPGERATLSCRASQSVSSNLAWYQQKPGQAPRLLIFGASTRATGIPARFSGSGSGTEFTL<br>TISSLQSEDFAVYYCQQLLTWPPRTFGGGTKVEIK | 175 |
| 6266 | 3 | EIVMTQSPATLSVSPGERATLSCRASQSVSSNLAWYQQKPGQAPRLLIYGASTRATGIPARFSGSGSGTEFTL<br>TISSLQSEDFAVYYCQQLILWPPRTFGGGTKVEIK | 156 |
| 6271 | 3 | EIVMTQSPATLSVSPGERATLSCRASQSVSSNLAWYQQKPGQAPRLLIYGASTRATGIPARFSGSGSGTEFTL<br>TISSLQSEDFAVYYCQQLILWPPRTFGGGTKVEIK | 156 |
| 6297 | 3 | EIVLTQSPATLSLSPGERATLSCRASQSVSSYLAWFQQKPGQAPRLLIYDASNRATGIPARFSGSGSGTDFTL<br>TISSLEPEDFAVYYCQQVYWPPRTFGGGTKVEIK | 166 |
| 6294 | 3 | EIVLTQSPATLSLSPGERATLSCRASQSVSSYLAWYQQKPGQAPRLLIYDASKRATGIPARFSGSGSGTDFTL<br>TISSLEPEDFAVYYCQQVYTWPPRTFGGGTKVEIK | 163 |
| 5932 | 3 | EIVLTQSPATLSLSPGERATLSCRASQSVSSYLAWYQQKPGQAPRLLIYDASKRATGIPARFSGSGSGTDFTL<br>TISSLEPEDFAVYYCQQVYTWPPRTFGGGTKVEIK | 163 |
| 6313 | 3 | EIVLTQSPATLSLSPGERATLSCRASQSVSSYLAWYQQKPGQAPRLLIYDASNRATGIPARFSGSGSGTDFTL<br>TISSLEPEDFAVYYCQQAYVWPPRTFGGGTKVEIK | 161 |
| 6314 | 3 | EIVLTQSPATLSLSPGERATLSCRASQSVSSYLAWYQQKPGQAPRLLIYDASNRATGIPARFSGSGSGTDFTL<br>TISSLEPEDFAVYYCQQSIVWPPRTFGGGTKVEIK | 171 |
| 6315 | 3 | EIVLTQSPATLSLSPGERATLSCRASQSVSSYLAWYQQKPGQAPRLLIYDASKRATGIPARFSGSGSGTDFTL<br>TISSLEPEDFAVYYCQQSLVWPPRTFGGGAKVEIK | 176 |
| 5933 | 3 | EIVLTQSPATLSLSPGERATLSCRASQSVSSYLAWYQQKPGQAPRLLIYGASKRATGIPARFSGSGSGTDFTL<br>TISSLEPEDFAVYYCQQVYTWPPRTFGGGTKVEIK | 164 |
| 6285 | 3 | EIVLTQSPATLSLSPGERATLSCRASQSVSSYLAWYQQKPGQAPRLLIYDASSRATGIPARFSGSGSGTDFTL<br>TISSLEPEDFAVYYCQQSLTWPPRTFGGGTKVEIK | 177 |
| 6280 | 3 | EIVLTQSPATLSLSPGERATLSCRASQSVSSYLAWYQQKPGQAPRLLIYDASNRATGIPARFSGSGSGTDFTL<br>TISSLEPEDFAVYYCQQSLTWPPRTFGGGTKVEIK | 162 |
| 6288 | 3 | EIVLTQSPATLSLSPGERATLSCRASQSVSSYLAWYQQKPGQAPRLLIYDASNRATGIPARFSGSGSGTDFTL<br>TISSLEPEDFAVYYCQQSLTWPPRTFGGGTKVEIK | 162 |
| 5539 | 3 | DIQMTQSPSSLSASVGDRVTITCRASQSISSYLNWYQQKPGKAPKLLIYAASSLQSGVPSRFSGSGSGTDFTL<br>TISSLQPEDFATYYCQQPLSHPRTFGGGTKVEIK | 178 |

FIG. 4F

| | Octet Affinity Measurements | | | | |
|---|---|---|---|---|---|
| Ab Name | KD Human-IgG, pH 7.5 (M) | KD Murine-IgG, pH 7.5 (M) | KD Human-IgG, pH 5.0 (M) | KD Murine-IgG, pH 5.0 (M) | KD (M) Biacore |
| 5260 | 9.40E-08 | 9.40E-08 | 1.20E-07 | 1.80E-07 | 1.45E-08 |
| 5531 | 7.60E-08 | 4.20E-08 | W.B. | W.B. | 1.23E-07 |
| 5532 | 7.60E-08 | 4.80E-08 | W.B. | W.B. | 1.30E-07 |
| 5536 | 1.50E-08 | 2.20E-08 | 1.70E-08 | 6.80E-09 | P.F. |
| 5539 | 7.90E-08 | 1.10E-07 | W.B. | W.B. | 3.05E-08 |
| 5543 | 2.60E-08 | 2.40E-08 | 4.80E-08 | 4.00E-08 | 7.01E-09 |
| 5571 | 5.00E-09 | 5.40E-09 | 8.20E-09 | 8.40E-09 | 7.31E-09 |
| 5572 | 8.60E-10 | 2.50E-09 | 1.50E-09 | 2.00E-09 | 2.82E-09 |
| 5583 | 7.80E-08 | 5.10E-08 | W.B. | W.B. | 8.18E-08 |
| 5586 | 1.10E-07 | 1.20E-07 | 1.80E-07 | 1.80E-06 | P.F. |
| 5592 | 5.90E-08 | 3.80E-08 | W.B. | W.B. | 1.05E-07 |
| 5643 | 9.60E-09 | 1.00E-08 | 2.00E-08 | 1.70E-08 | 1.06E-08 |
| 5644 | 1.50E-08 | 1.70E-08 | 1.20E-08 | 1.10E-08 | 1.33E-08 |
| 5747 | 3.3E-09 | 2.20E-09 | 3.0E-9 | 3.1E-09 | |
| 5874 | 3.30E-08 | 2.20E-08 | P.F. | 2.00E-07 | 1.30E-09 |
| 5875 | 3.20E-08 | 2.20E-08 | 5.00E-08 | 1.20E-07 | 1.94E-09 |
| 5876 | 9.40E-09 | 9.70E-09 | 3.10E-08 | 4.30E-08 | 7.20E-10 |
| 5878 | 2.50E-09 | 2.70E-09 | 1.10E-08 | 1.40E-08 | 3.60E-08 |
| 5880 | 1.00E-09 | 1.20E-09 | 4.50E-09 | 6.10E-09 | 6.55E-08 |
| 5881 | 2.60E-09 | 2.40E-09 | 1.10E-08 | 1.50E-08 | 7.92E-09 |
| 5883 | 4.60E-09 | 6.60E-09 | 8.70E-09 | 1.10E-08 | 6.04E-09 |
| 5884 | 9.20E-10 | 1.30E-09 | 1.40E-09 | 2.00E-09 | 2.62E-09 |
| 5884* | 4.6E-10 | 4.90E-10 | 8.6E-10 | 1.3E-09 | 5.23E-09 |
| 5887 | 1.10E-09 | 1.40E-09 | 2.20E-09 | 2.30E-09 | 3.58E-09 |

*FIG. 5A*

| Ab Name | KD Human-IgG, pH 7.5 (M) | KD Murine-IgG, pH 7.5 (M) | KD Human-IgG, pH 5.0 (M) | KD Murine-IgG, pH 5.0 (M) | KD (M) Biacore |
|---|---|---|---|---|---|
| 5887* | 4.5E-10 | 5.40E-10 | 1.4E-9 | 1.8E-09 | 7.08E-09 |
| 5888 | 8.60E-10 | 1.40E-09 | 1.80E-09 | 2.00E-09 | 4.25E-09 |
| 5890 | 5.50E-10 | 1.00E-09 | 6.40E-10 | 7.90E-10 | 3.22E-09 |
| 5891 | 6.50E-10 | 1.40E-09 | 9.60E-10 | 1.10E-09 | 3.29E-09 |
| 5892 | 8.80E-10 | 1.30E-09 | 3.90E-10 | 1.10E-09 | 2.97E-09 |
| 5893 | 3.30E-10 | 9.80E-10 | 3.80E-10 | 7.30E-10 | 2.76E-09 |
| 5894 | 2.70E-10 | 8.60E-10 | 3.00E-10 | 6.50E-10 | 2.95E-09 |
| 5894* | <3.8E-10 | <4.0E-10 | <2.7E-10 | <3.8E-10 | |
| 5896 | 1.90E-09 | 2.90E-09 | 3.00E-09 | 3.10E-09 | 3.40E-09 |
| 5896* | 7.1E-10 | 8.00E-10 | 1.1E-9 | 1.00E-09 | 5.18E-09 |
| 5897 | 9.50E-10 | 1.10E-09 | 8.20E-10 | 8.20E-10 | 2.07E-09 |
| 5902 | 3.90E-09 | 5.30E-09 | 1.40E-09 | 1.50E-09 | 3.28E-09 |
| 5903 | 1.60E-09 | 1.50E-09 | 8.60E-10 | 7.60E-10 | 8.65E-09 |
| 5903* | 5.3E-10 | 5.10E-10 | <3.4E-10 | <4.3E-10 | 2.41E-09 |
| 5905 | 1.30E-09 | 1.40E-09 | 1.10E-09 | 1.10E-09 | 3.53E-09 |
| 5905* | 5.1E-10 | 4.00E-10 | 2.7E-10 | 3.8E-10 | |
| 5930 | <2.9E-10 | <3.E-10 | <2.3E-10 | <2.9.E-10 | 6.41E-09 |
| 5931 | <2.2E-10 | <2.3E-10 | <2.2E-10 | <2.8E-10 | |
| 5932 | 3.1E-10 | <3E-10 | <2.3E-10 | <3E-10 | |
| 5933 | 3.2E-10 | <2.4E-10 | <2.0E-10 | <2.4E-10 | |
| 5982 | 2.9E-09 | 2.00E-09 | 2.3E-9 | 2.3E-09 | |
| 5983 | 3.5E-10 | <2.4E-10 | 3.4E-10 | 3.4E-20 | |
| 5984 | 4.3E-10 | 3.60E-10 | 3.4E-10 | 3.7E-10 | |
| 5985 | 8.7E-10 | 6.50E-10 | 6.8E-10 | 8.1E-10 | |
| 5986 | 7.8E-10 | 5.40E-10 | <2.4E-10 | <2.7E-10 | |

*FIG. 5B*

| Ab Name | KD Human-IgG, pH 7.5 (M) | KD Murine-IgG, pH 7.5 (M) | KD Human-IgG, pH 5.0 (M) | KD Murine-IgG, pH 5.0 (M) | KD (M) Biacore |
|---|---|---|---|---|---|
| 5987 | <3.2E-10 | <2.9E-10 | <2.5E-10 | <2.9E-10 | |
| 5988 | <2.9E-10 | <2.9E-10 | <2.5E-10 | <2.9E-10 | |
| 5990 | <1.8E-10 | <1.8E-10 | <1.8E-10 | <2.3E-10 | |
| 6266 | <3E-10 | <3.1E-10 | <2.4E-10 | 3.2E-10 | 1.12E-09 |
| 6270 | <2.9E-10 | <4.0E-10 | <2.9E-10 | <4.1E-10 | 4.64E-09 |
| 6271 | <3.1E-10 | <3.1E-10 | <2.4E-10 | <3.1E-10 | |
| 6272 | <8.7E-10 | <4.1E-10 | <3.9E-10 | <4.0E-10 | |
| 6273 | <3.9E-10 | <3.9E-10 | <2.6E-10 | <4.0E-10 | |
| 6274 | <3.7E-10 | <3.7E-10 | 5.3E-10 | 7.6E-10 | 4.18E-09 |
| 6275 | <4.8E-10 | <4.9E-10 | <3.4E-10 | <3.7E-10 | 2.68E-09 |
| 6276 | <5.9E-10 | <6.2E-10 | <4.1E-10 | <5.4E-10 | |
| 6279 | <4.5E-10 | <4.6E-10 | <3.6E-10 | <4.3E-10 | 2.11E-09 |
| 6280 | <3.2E-10 | <3.2E-10 | 3.10E-10 | <3.1E-10 | |
| 6285 | 3.2E-10 | <2.8E-10 | 4.3E-10 | 4.1E-10 | |
| 6288 | <2.1E-10 | <2.3E-10 | <2.1E-10 | 2.8E-10 | 4.79E-09 |
| 6289 | 3.7E-10 | 2.80E-10 | 3.9E-10 | 3.8E-10 | 7.37E-09 |
| 6290 | <2.6E-10 | <2.7E-10 | <2.3E-10 | <2.7E-10 | 3.19E-09 |
| 6291 | <2.8E-10 | <2.6E-10 | <2.6E-10 | <3.0E-10 | |
| 6293 | <2.8E-10 | <2.8E-10 | <2.8E-10 | <2.8E-10 | 8.26E-09 |
| 6294 | <3E-10 | <3.0E-10 | <2.7E-10 | <3.4E-10 | |
| 6296 | 2.8E-10 | <2.4E-10 | 2E-10 | <2.4E-10 | 3.29E-09 |
| 6297 | 4E-10 | <2.6E-10 | 2.8E-10 | 3.2E-10 | 3.87E-09 |
| 6298 | 3.9E-10 | 4.60E-10 | 3.2E-10 | 4.0E-10 | |
| 6299 | <4.1E-10 | <4.1E-10 | <2.8E-10 | <4.6E-10 | 5.82E-09 |
| 6300 | <8E-10 | <6.8E-10 | <3.4E-10 | <4.0E-10 | |

*FIG. 5C*

| Ab Name | KD Human-IgG, pH 7.5 (M) | KD Murine-IgG, pH 7.5 (M) | KD Human-IgG, pH 5.0 (M) | KD Murine-IgG, pH 5.0 (M) | KD (M) Biacore |
|---|---|---|---|---|---|
| 6303 | <3.2E-10 | <3.5E-10 | <2.6E-10 | <3.2E-10 | 3.09E-09 |
| 6305 | 5.3E-10 | 5.60E-10 | 9.6E-10 | 1.6E-09 | |
| 6307 | <1.4E-10 | <1.5E-10 | <1.3E-10 | <1.7E-10 | |
| 6308 | <1.4E-10 | <1.5E-10 | <1.4E-10 | <1.7E-10 | |
| 6309 | 3.4E-10 | 3.20E-10 | 3.5E-10 | 3.7E-10 | |
| 6310 | 4.6E-10 | 4.70E-10 | 4.4E-10 | 5.0E-10 | 1.63E-09 |
| 6311 | 2.5E-10 | 2.40E-10 | 2.0E-10 | 2.1E-10 | |
| 6313 | 4.1E-10 | 2.70E-10 | <2.1E-10 | <2.4E-10 | |
| 6314 | 3.8E-10 | 3.30E-10 | <2.2E-10 | <2.6E-10 | |
| 6315 | <2.5E-10 | <2.6E-10 | <2.1E-10 | <2.5E-10 | |

^Mix of 30 min and 120 min dissociation experiments
* Antibody KD determined in two separate assay runs
P.F. = Poor Fit/No reported KD
W.B. = Weak binding/No fit

FIG. 5D

| Ab Name | Small substrate assay Human-BACE1 (% inhibition) | Small substrate assay Human-BACE1 (std. error, n = 4) | Small substrate assay Murine-BACE1 (% inhibition) | Small substrate assay Murine-BACE1 (std. error, n = 4) |
|---|---|---|---|---|
| 5260 | -54% | -10% | -35% | -8% |
| 5531 | 61% | 4% | 57% | 9% |
| 5532 | 56% | 5% | 50% | 8% |
| 5536 | 32% | 3% | 30% | 15% |
| 5539 | 42% | 4% | 23% | 3% |
| 5543 | 61% | 4% | 61% | 9% |
| 5571 | -89% | -17% | -175% | -16% |
| 5572 | 75% | 4% | 77% | 9% |
| 5583 | 44% | 8% | 34% | 8% |
| 5586 | 41% | 6% | 51% | 7% |
| 5592 | 63% | 4% | 60% | 8% |
| 5643 | -64% | -16% | -20% | -8% |
| 5644 | 65% | 4% | 63% | 9% |
| 5874 | 37% | 12% | 33% | 8% |
| 5875 | 51% | 4% | 39% | 8% |
| 5876 | 58% | 4% | 46% | 8% |
| 5878 | 99% | 5% | 98% | 10% |
| 5880 | 99% | 5% | 97% | 10% |
| 5881 | 97% | 5% | 98% | 10% |
| 5883 | -129% | -9% | -275% | -30% |
| 5884 | -102% | -6% | -243% | -25% |
| 5887 | -102% | -12% | -230% | -18% |
| 5888 | -86% | -9% | -183% | -25% |
| 5890 | 66% | 7% | 69% | 9% |
| 5891 | 71% | 6% | 70% | 9% |
| 5892 | 64% | 4% | 64% | 9% |
| 5893 | 72% | 4% | 69% | 9% |
| 5894 | 69% | 4% | 69% | 9% |
| 5896 | -4% | -8% | -3% | -10% |
| 5897 | 1% | 4% | -3% | -12% |
| 5902 | 66% | 5% | 66% | 9% |
| 5903 | 68% | 4% | 69% | 9% |
| 5905 | 65% | 7% | 72% | 9% |

FIG. 6

| | HTRF Long Substrate | | | FRET Short Substrate | | |
|---|---|---|---|---|---|---|
| Ab Name | Data Mode | EC50 (M) | \|dS\| | Data Mode | EC50 (M) | \|dS\| |
| 5260 | decreasing | 7.20E-07 | 106.2 | decreasing | 3.68E-08 | 55.62 |
| 5531 | decreasing | 1.51E-07 | 103.1 | decreasing | 2.12E-08 | 68.54 |
| 5532 | decreasing | 1.04E-07 | 100.7 | decreasing | 5.23E-08 | 94.59 |
| 5536 | decreasing | 5.78E-10 | 84.97 | N.D. | | |
| 5539 | decreasing | 6.94E-10 | 92.22 | N.D. | | |
| 5543 | decreasing | 3.00E-08 | 92.94 | decreasing | 9.11E-09 | 84.7 |
| 5571 | decreasing | 5.06E-09 | 91.95 | increasing | 4.17E-10 | 78.38 |
| 5572 | decreasing | 1.28E-09 | 89.17 | decreasing | 1.59E-08 | 69.75 |
| 5583 | decreasing | 1.72E-07 | 87.25 | decreasing | 9.72E-09 | 72.74 |
| 5586 | decreasing | 2.39E-09 | 97.3 | N.D. | | |
| 5592 | decreasing | 1.89E-07 | 96.02 | decreasing | 9.59E-08 | 94.72 |
| 5643 | decreasing | 1.77E-08 | 107.7 | decreasing | 1.41E-09 | 96.2 |
| 5644 | decreasing | 8.75E-09 | 115.6 | decreasing | 8.47E-09 | 80.43 |
| 5874 | decreasing | 3.97E-09 | 116.1 | decreasing | 7.98E-10 | 105.2 |
| 5875 | decreasing | 4.90E-09 | 116.1 | decreasing | 1.99E-09 | 100 |
| 5876 | decreasing | 1.67E-09 | 109.8 | decreasing | 7.03E-10 | 117.3 |
| 5878 | decreasing | 1.64E-07 | 103.3 | decreasing | 2.43E-08 | 69.49 |
| 5880 | decreasing | 1.71E-07 | 97.19 | decreasing | 7.88E-09 | 69.66 |
| 5881 | decreasing | 3.37E-08 | 110.1 | decreasing | 5.93E-09 | 83.91 |
| 5883 | decreasing | 5.93E-09 | 71.45 | increasing | 6.07E-10 | 117.2 |
| 5884 | decreasing | 7.76E-09 | 81.71 | increasing | 4.78E-10 | 91.84 |
| 5887 | decreasing | 5.50E-09 | 84.97 | increasing | 4.82E-10 | 103.6 |

FIG. 7A

| Ab Name | HTRF Long Substrate | | | FRET Short Substrate | | |
|---|---|---|---|---|---|---|
| | Data Mode | EC50 (M) | \|dS\| | Data Mode | EC50 (M) | \|dS\| |
| 5888 | decreasing | 2.50E-09 | 95.34 | increasing | 6.02E-10 | 101.3 |
| 5890 | decreasing | 4.06E-09 | 72.43 | decreasing | 3.24E-08 | 61.59 |
| 5891 | decreasing | 3.03E-09 | 80.77 | decreasing | 1.24E-08 | 47.16 |
| 5892 | decreasing | 1.19E-09 | 83.93 | decreasing | 1.64E-08 | 53.1 |
| 5893 | decreasing | 3.59E-09 | 78.29 | decreasing | 8.84E-09 | 62.99 |
| 5894 | decreasing | 1.79E-09 | 112.7 | decreasing | 8.58E-09 | 63.43 |
| 5896 | decreasing | 3.46E-09 | 102.4 | decreasing | 3.35E-09 | 86.98 |
| 5897 | decreasing | 1.39E-09 | 95.35 | decreasing | 5.28E-10 | 90.49 |
| 5902 | decreasing | 1.41E-09 | 81.24 | decreasing | 1.41E-09 | 89.02 |
| 5903 | decreasing | 1.38E-09 | 95.23 | decreasing | 3.12E-09 | 86.52 |
| 5905 | decreasing | 3.91E-09 | 78.64 | decreasing | 1.33E-09 | 89.42 |

N.D. not determind

*FIG. 7B*

| Ab Name | IC50 (nM) | Percent Inhibition |
| --- | --- | --- |
| 5260 | 46.7 | 74 |
| 5531 | poor inhibition | |
| 5532 | poor inhibition | |
| 5536 | 42.39 | 84 |
| 5539 | 17.59 | 45 |
| 5543 | 18.3 | 65 |
| 5571 | 7.11 | 84 |
| 5572 | 27.1 | 73 |
| 5583 | poor inhibition | |
| 5586 | poor inhibition | |
| 5592 | poor inhibition | |
| 5643 | 9.71 | 60 |
| 5644 | 8.33 | 72 |
| 5747 | 25.55 | 74 |
| 5874 | poor inhibition | |
| 5875 | poor inhibition | |
| 5876 | poor inhibition | |
| 5878 | poor inhibition | |
| 5880 | poor inhibition | |
| 5881 | poor inhibition | |
| 5883 | 9.11 | 82 |
| 5884 | 4.56 | 83 |
| 5884* | 3.51 | 75 |
| 5887 | 1.74 | 75 |
| 5887* | 2.53 | 82 |
| 5888 | 1.79 | 82 |
| 5890 | 8.45 | 77 |
| 5891 | 18 | 78 |
| 5892 | 9.52 | 73 |
| 5893 | 9.46 | 73 |
| 5894 | 6.48 | 78 |
| 5894* | 5.43 | 73 |
| 5896 | 2.7 | 65 |
| 5896* | 5.72 | 67 |
| 5897 | 0.30 | 62 |
| 5902 | 1.59 | 67 |

FIG. 8A

| Ab Name | IC50 (nM) | Percent Inhibition |
| --- | --- | --- |
| 5903 | 1.63 | 72 |
| 5903* | 7.27 | 73 |
| 5905 | 0.33 | 65 |
| 5905* | 0.83 | 73 |
| 5930 | 7.52 | 74 |
| 5931 | 0.91 | 69 |
| 5932 | 6.26 | 57 |
| 5933 | 3.60 | 67 |
| 5982 | 27.34 | 71 |
| 5983 | 7.34 | 72 |
| 5984 | 22.61 | 70 |
| 5985 | poor inhibition | 73 |
| 5986 | 5.42 | 67 |
| 5987 | 7.20 | 69 |
| 5988 | 3.55 | 75 |
| 5990 | 0.53 | 61 |
| 6266 | 1.66 | 87 |
| 6270 | 4.48 | 85 |
| 6271 | 1.77 | 83 |
| 6272 | 43.61 | 82 |
| 6273 | 5.71 | 82 |
| 6274 | 4.82 | 85 |
| 6275 | 1.27 | 71 |
| 6276 | 7.40 | 81 |
| 6279 | 6.23 | 71 |
| 6280 | 8.29 | 65 |
| 6285 | 15.44 | 57 |
| 6288 | 11.00 | 67 |
| 6289 | 5.21 | 74 |
| 6290 | 3.17 | 63 |
| 6291 | 1.41 | 68 |
| 6293 | 0.88 | 75 |
| 6294 | 3.53 | 59 |
| 6296 | 7.92 | 62 |
| 6297 | 3.89 | 63 |
| 6298 | 1.95 | 67 |

*FIG. 8B*

| Ab Name | IC50 (nM) | Percent Inhibition |
|---|---|---|
| 6299 | 10.44 | 70 |
| 6300 | 9.10 | 71 |
| 6303 | 4.10 | 76 |
| 6305 | 9.69 | 67 |
| 6307 | 0.45 | 68 |
| 6308 | 0.68 | 60 |
| 6309 | 0.30 | 60 |
| 6310 | 0.17 | 71 |
| 6311 | 0.15 | 63 |
| 6313 | 2.78 | 67 |
| 6314 | 3.38 | 71 |
| 6315 | poor fit | 73 |

* Inhibition by this antibody determined in two separate assay runs

| Clone | Mutation | ka (1/Ms) | kd (1/s) | KD (nM) | Tm (°C) |
|---|---|---|---|---|---|
| 6266wt | | 3.71E+05 | 4.03E-04 | 1.09 | 69.2 |
| 6266.1 | G31H,F54I | 6.54E+05 | 1.61E-04 | 0.24 | 72.8 |
| 6266.2 | G31H,F54I,T53K,F83A | 2.45E+05 | 1.42E-04 | 0.58 | 74.2 |
| 6266.3 | G31H,F54I,T56Y | 4.80E+05 | 1.42E-04 | 0.29 | 73 |
| 6266.4 | G31H,F54I,T53K | 6.38E+05 | 1.70E-04 | 0.26 | 72.4 |
| 6266.5 | G31H,F54I,K99Q,T53K,F83A | 4.28E+05 | 2.28E-04 | 0.53 | 73.8 |
| 6266.6 | G31H,F54I,K99Q,T56Y,F83A | 3.56E+05 | 2.78E-04 | 0.78 | 72 |
| 6266.7 | G31H,F54I,M100bE,T56Y,F83A | 5.42E+05 | 3.33E-04 | 0.62 | 73.2 |
| 6266.8 | S30K,S95G,T56Y | 4.88E+05 | 2.75E-04 | 0.56 | n/a |
| 6266.9 | S30K,S95G,T53K | 4.45E+05 | 3.05E-04 | 0.68 | n/a |
| 6266.10 | T53K | 7.56E+05 | 5.06E-04 | 0.69 | 72.8 |
| 6266.11 | T56Y | 8.91E+05 | 4.10E-04 | 0.46 | 69 |
| 6266.12 | S30N | 8.54E+05 | 4.47E-04 | 0.52 | 72.2 |
| 6266.13 | V34M | 7.34E+05 | 4.11E-04 | 0.56 | 70.8 |
| 6266.14 | T56V,Y100W | 8.39E+05 | 4.74E-04 | 0.57 | 69.2 |
| 6266.15 | M100bE | 7.74E+05 | 4.95E-04 | 0.64 | 69.8 |

*FIG. 14*

ANTIBODIES AGAINST BACE1 AND USE THEREOF FOR NEURAL DISEASE IMMUNOTHERAPY

CROSS-REFERENCE TO RELATED APPLICATIONS

This application is a divisional of U.S. application Ser. No. 15/525,791, filed May 10, 2017, which is a national phase entry pursuant to 35 U.S.C. § 371 of International Application No. PCT/US2015/061401, filed Nov. 18, 2015, which claims the benefit of priority of U.S. Provisional Application No. 62/081,966, filed Nov. 19, 2014, all of which are incorporated by reference herein in their entirety for any purpose.

SEQUENCE LISTING

The present application is filed with a Sequence Listing in electronic format. The Sequence Listing is provided as a file entitled "2020-12-02_01146-0040-01US_ST25.txt" created on Dec. 2, 2020, which is 181,893 bytes in size. The information in the electronic format of the sequence listing is incorporated herein by reference in its entirety.

FIELD OF THE INVENTION

The present invention relates generally to antibodies which are BACE1 antagonists that, for example, inhibit or decrease BACE1 activity and to compositions comprising such antibodies. Additional embodiments include methods for treating and diagnosing various neurological diseases or disorders, as well as methods of reducing APP and/or Aβ polypeptides in a patient.

BACKGROUND

Amyloidosis is not a single disease entity but rather a diverse group of progressive disease processes characterized by extracellular tissue deposits of a waxy, starch-like protein called amyloid, which accumulates in one or more organs or body systems. As the amyloid deposits accumulate, they begin to interfere with the normal function of the organ or body system. There are at least 15 different types of amyloidosis. The major forms are primary amyloidosis without known antecedent, secondary amyloidosis following some other condition, and hereditary amyloidosis.

Many diseases of aging are based on or associated with amyloid-like proteins and are characterized, in part, by the buildup of extracellular deposits of amyloid or amyloid-like material that contribute to the pathogenesis, as well as the progression of the disease. These diseases include, but are not limited to, neurological disorders such as Alzheimer's Disease (AD), Lewy body dementia, Down's syndrome, hereditary cerebral hemorrhage with amyloidosis (Dutch type); the Guam Parkinson-Dementia complex. Other diseases which are based on or associated with amyloid-like proteins are progressive supranuclear palsy, multiple sclerosis, Creutzfeld Jacob disease, Parkinson's disease, HIV-related dementia, ALS (amyotropic lateral sclerosis), Adult Onset Diabetes, senile cardiac amyloidosis, endocrine tumors, and others, including macular degeneration.

The polypeptide β-amyloid (Aβ) is likely to play a central role in the pathogenesis of Alzheimer's disease (AD). Vassar et al., *J. Neurosci.* 29:12787-12794 (2009). Aβ polypeptide accumulation in the CNS results in synaptic dysfunction, axon degeneration and neuronal death. The brains of AD patients show a characteristic pathology of prominent neuropathologic lesions, such as neurofibrillary tangles (NFTs), and amyloid-rich senile plaques. The major component of amyloid plaques is Aβ. These lesions are associated with massive loss of populations of central nervous system (CNS) neurons and their progression accompanies the clinical dementia associated with AD.

Aβ is the proteolytic product of the precursor protein, beta amyloid precursor protein (β-APP or APP). APP is a type-I trans-membrane protein which is sequentially cleaved by two proteases, a β- and γ-secretase. The β-secretase, known as β-site amyloid precursor protein cleaving enzyme 1 (BACE1), first cleaves APP to expose the N-terminus of Aβ, thereby producing a membrane bound fragment known as C99. Vassar et al., *J. Neurosci.*, 29:12787-12794 (2009) and UniProtKB/Swiss-Prot Entry P56817 (BACE1_HUMAN). The γ-secretase then is able to cleave C99 to produce the mature Aβ polypeptide. Aβ is produced with heterogenous C termini ranging in length from 38 amino acids to 43 amino acids. The 42 amino acid form of Aβ ($A\beta_{42}$) is the fibrillogenic form of Aβ and is over produced in patients with Down's syndrome and has been suggested to play a role in the early pathogenesis of AD. Vassar et al., *J. Neurosci.* 29:12787-12794 (2009). BACE1 has thus become a therapeutic target as its inhibition would presumably inhibit APP and Aβ production.

Indeed, BACE1 knock-out mice ($BACE1^{-/-}$) do not produce cerebral Aβ, confirming that BACE1 is the major, if not only, enzyme responsible for producing Aβ in the brain. Roberds et al., *Human Mol. Genetics* 10:1317-1324 (2001). Moreover, BACE1 knockout mice in AD models do not form amyloid plaques; cognitive defects and cholinergic dysfunction are rescued as well. McConlogue et al., *J. Biol. Chem.* 282: 26326-26334 (2007); Ohno et al., *Neuron* 41: 27-33 (2004); and Laird et al., *J. Neurosci.* 25:11693-11709 (2005). Additionally, BACE1 heterozygous knock-out mice have reduced plaque formation indicating the complete inhibition of BACE1 activity is not necessary for plaque reduction. McConlogue et al., *J. Biol. Chem.* 282: 26326-26334 (2007).

It would be beneficial to have an effective therapeutic inhibitor of BACE1 to reduce APP and Aβ production in patients with neurological diseases and disorders, such as AD. The invention provided herein relates to such inhibitors, including their use in a variety of methods.

All references cited herein, including patent applications and publications, are incorporated by reference in their entirety.

SUMMARY

The invention provides BACE1 antagonist antibodies and methods of using the same. Specifically, the antibodies inhibit or reduce the activity of BACE1.

In some embodiments, an isolated antibody that binds to BACE1 is provided, wherein the antibody comprises:
  a) an HVR-H1 sequence selected from SEQ ID NOs: 1 to 6; an HVR-H2 sequence selected from SEQ ID NOs: 22 to 25; an HVR-H3 sequence selected from SEQ ID NOs: 50 and 51; an HVR-L1 sequence selected from SEQ ID NOs: 62 and 63; an HVR-L2 sequence selected from SEQ ID NOs: 69 and 70; and an HVR-L3 sequence selected from SEQ ID NOs: 75 to 78 and 98; or
  b) an HVR-H1 sequence selected from SEQ ID NOs: 7 to 21, 218, and 222 to 224; an HVR-H2 sequence selected from SEQ ID NOs: 26 to 49, 232, 219, and 225; an HVR-H3 sequence selected from SEQ ID NOs: 52 to 61, 220, 221, 226, and 227; an HVR-L1 sequence selected from SEQ ID NOs: 64 to 68; an HVR-L2 sequence selected from SEQ ID NOs: 69 to 74 and 217; and an HVR-L3 sequence selected from SEQ ID NOs: 79 to 97.

In some embodiments, an isolated antibody that binds to BACE1 is provided, wherein the antibody comprises the HVR-H1, HVR-H2, HVR-H3, HVR-L1, HVR-L2, and HVR-L3 of an antibody selected from the antibodies in Table 1. In some embodiments, the antibody is selected from 6266 and 6266 variants 1-15. In some embodiments, the antibody comprises an HVR-H1 sequence selected from SEQ ID NOs: 15, 218, and 222 to 224; an HVR-H2 sequence selected from SEQ ID NOs: 29, 219, and 255; an HVR-H3 sequence selected from SEQ ID NOs: 52, 220, 221, 226, and 227; an HVR-L1 sequence of SEQ ID NO: 65; an HVR-L2 sequence selected from SEQ ID NOs: 71, 73, and 217; and an HVR-L3 sequence of SEQ ID NO: 80. In some embodiments, the antibody comprises:
   a) a heavy chain variable domain sequence having at least 90% sequence identity to an amino acid sequence selected from SEQ ID NOs: 99 to 147, 194 to 200, and 209 to 216; or
   b) a light chain variable domain sequence having at least 90% sequence identity to an amino acid sequence selected from SEQ ID NOs: 148 to 178, 187 to 194, and 201 to 208; or
   c) a heavy chain variable domain sequence as in (a) and a light chain variable domain sequence as in (b).

In some embodiments, an isolated antibody that binds BACE1 comprises:
   a) a heavy chain variable domain sequence selected from SEQ ID NOs: 99 to 147, 194 to 200, and 209 to 216; or
   b) a light chain variable domain sequence selected from SEQ ID NOs: 148 to 178, 187 to 194, and 201 to 208; or
   c) a heavy chain variable domain sequence as in (a) and a light chain variable domain sequence as in (b).

In some embodiments, an isolated antibody that binds BACE1 comprises:
   a) a heavy chain variable domain sequence having at least 90% sequence identity to a sequence selected from SEQ ID NOs: 138, 194 to 200, and 209 to 216; or
   b) a light chain variable domain sequence having at least 90% sequence identity to a sequence selected from SEQ ID NOs: 156, 187 to 194, and 201 to 208; or
   c) a heavy chain variable domain sequence as in (a) and a light chain variable domain sequence as in (b).

In some embodiments, an isolated antibody that binds BACE1 comprises:
   a) a heavy chain variable domain sequence selected from SEQ ID NOs: 138, 194 to 200, and 209 to 216; or
   b) a light chain variable domain sequence selected from SEQ ID NOs: 156, 187 to 194, and 201 to 208; or
   c) a heavy chain variable domain sequence as in (a) and a light chain variable domain sequence as in (b); or
   d) a heavy chain variable domain sequence and a light chain variable domain sequence of an antibody selected from 6266 and 6266 variants 1-15.

In some embodiments, the isolated antibody modulates the activity of BACE1. In some embodiments, the antibody inhibits the activity of BACE1. In some embodiments, BACE1 activity is measured using a homogeneous time-resolved fluorescence (HTRF) assay. In some embodiments, BACE1 activity is measured using a cell line that expresses a BACE1 substrate. In some embodiments, the BACE1 substrate is amyloid precursor protein (APP). In some embodiments, BACE1 activity is measured in tissue from an animal that has been administered the anti-BACE1 antibody. In some embodiments, the tissue is brain tissue. In some embodiments, the animal is selected from a mouse, rat, rabbit, dog, monkey, and non-human primate.

In some embodiments, the antibody is an allosteric inhibitor of BACE1 activity. In some embodiments, the antibody binds BACE1 with an affinity (KD) of between 0.1 nM and 10 nM, or between 0.1 nM and 8 nM, or between 0.1 nM and 7 nM, or between 0.1 nM and 5 nM, or between 0.5 nM and 5 nM, or between 0.1 nM and 3 nM, or between 0.5 nM and 3 nM, as measured by surface plasmon resonance (SPR). In some embodiments, the antibody achieves a maximum inhibition of BACE1 activity of greater than 60%, greater than 70%, greater than 75%, or greater than 80%, as measured, for example, using the dissociated cortical neuron culture assay.

An antibody of the invention can be in any number of forms. For example, an antibody of the invention can be a human antibody or chimeric antibody. In other aspects the antibody of the invention is a full length antibody or a fragment thereof (e.g., a fragment comprising an antigen binding component). In some embodiments, the antibody fragment is selected from a Fab, Fab', Fab'-SH, F(ab')2, Fv, and scFv. In some embodiments, the antibody is a full length IgG1 antibody. In other aspects of the invention, the antibody is a monoclonal antibody. In another aspect, an antibody of the invention can be linked or conjugated to an agent or moiety, e.g. a cytotoxic agent, to create an immunoconjugate.

In some embodiments, a pharmaceutical formulation is provided which comprises an antibody of the invention and a pharmaceutically acceptable carrier. In additional embodiments an isolated nucleic acid encoding an antibody of the invention is provided, as well as vector that comprises the nucleic acid encoding an antibody of the invention. In another aspect, a host cell comprising the nucleic acid encoding an antibody of the invention is provided as well as methods for producing an antibody of the invention comprising culturing the host cell comprising the nucleic acid encoding an antibody of the invention under conditions suitable for production of the antibody.

In another embodiment, a method of treating an individual having a neurological disease or disorder comprising administering to the individual an effective amount of an antibody of the invention is provided.

In an additional embodiment, a method of reducing amyloid plaques, or inhibiting amyloid plaque formation, in a patient suffering from, or at risk of contracting, a neurological disease or disorder comprising administering to the individual an effective amount of an antibody of the invention is provided.

In some embodiments, a method of reducing Aβ protein in a patient comprising administering to the patient an effective amount of an antibody of the invention. In some aspects, the patient is suffering from, or at risk of contracting, a neurological disease or disorder.

In another embodiment, a method of inhibiting axon degeneration in a patient comprising administering to the patient an effective amount of an antibody of the invention is provided.

In an additional embodiment, a method of diagnosing a neurological disease or disorder in patient comprising contacting a biological sample isolated from the patient with an antibody of the invention under conditions suitable for binding of the antibody to a BACE1 polypeptide, and detecting whether a complex is formed between the antibody and the BACE1 polypeptide.

In some embodiments, a method of determining whether a patient is eligible for therapy with an anti-BACE1 antibody, comprising contacting a biological sample isolated from the patient with an antibody of the invention under conditions suitable for binding of the antibody to a BACE1 polypeptide, and detecting whether a complex is formed between the antibody and the BACE1 polypeptide, wherein the presence of a complex between the antibody and BACE1 is indicative of a patient eligible for therapy with an anti-BACE1 antibody. In some aspects the patient is suffering from, or at risk of contracting, a neurological disease or disorder.

In some aspects, biological samples that may be used in the diagnosis of a neurological disease or condition; or for predicting responsiveness, or determining eligibility, of a patient to a treatment with a BACE1 antibody include, but are not limited to, fluids such as serum, plasma, saliva, gastric secretions, mucus, cerebrospinal fluid, lymphatic fluid and the like or tissue or cell samples obtained from an organism such as neuronal, brain, cardiac or vascular tissue.

In some aspects of the methods of the invention, the patient is mammalian. In another aspect, the patient is human. In another aspect, the neurological disease or disorder is selected from the group consisting of Alzheimer's disease (AD), traumatic brain injury, stroke, glaucoma, dementia, muscular dystrophy (MD), multiple sclerosis (MS), amyotrophic lateral sclerosis (ALS), cystic fibrosis, Angelman's syndrome, Liddle syndrome, Paget's disease, traumatic brain injury, Lewy body disease, postpoliomyelitis syndrome, Shy-Draeger syndrome, olivopontocerebellar atrophy, Parkinson's disease, multiple system atrophy, striatonigral degeneration, supranuclear palsy, bovine spongiform encephalopathy, scrapie, Creutzfeldt-Jakob syndrome, kuru, Gerstmann-Straussler-Scheinker disease, chronic wasting disease, fatal familial insomnia, bulbar palsy, motor neuron disease, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome, dementia (including, but not limited to, Pick's disease, and spinocerebellar ataxia). In some aspects, the neurological disease or disorder is Alzheimer's disease. In some embodiments, the neurological disease or disorder is selected from the group consisting of Alzheimer's disease, stroke, traumatic brain injury and glaucoma.

BRIEF DESCRIPTION OF THE FIGURES

FIGS. 1A-1D show the epitope bin and heavy chain HVR-H1, HVR-H2, and HVR-H3 sequences of certain anti-BACE1 antibodies described herein.

FIGS. 2A-2C show the epitope bin and light chain HVR-L1, HVR-L2, and HVR-L3 sequences of certain anti-BACE1 antibodies described herein.

FIGS. 3A-3G show the epitope bin and heavy chain variable region (VH) sequences of certain anti-BACE1 antibodies described herein.

FIGS. 4A-4F show the epitope bin and light chain variable region (VL) sequences of certain anti-BACE1 antibodies described herein.

FIGS. 5A-5D show the affinity ($K_D$) of certain anti-BACE1 antibodies for human BACE1 at pH 7.5 (column 2), murine BACE1 at pH 7.5 (column 3), human BACE1 at pH 5.0 (column 4), and murine BACE1 at pH 5.0 (column 5) using an Octet® system (ForteBio); and the affinity ($K_D$) of certain anti-BACE1 antibodies for human BACE1 by surface plasmon resonance (Biacore™). For certain antibodies, affinities determined in two separate assays are shown.

FIG. 6 shows modulation of BACE1 activity by the anti-BACE1 antibodies using a short substrate assay.

FIGS. 7A-7B shows modulation of BACE1 activity by the anti-BACE1 antibodies using a long substrate assay and a short substrate assay.

FIGS. 8A-8C show in vitro modulation of APP processing in cells by the anti-BACE1 antibodies.

Figure 12B:
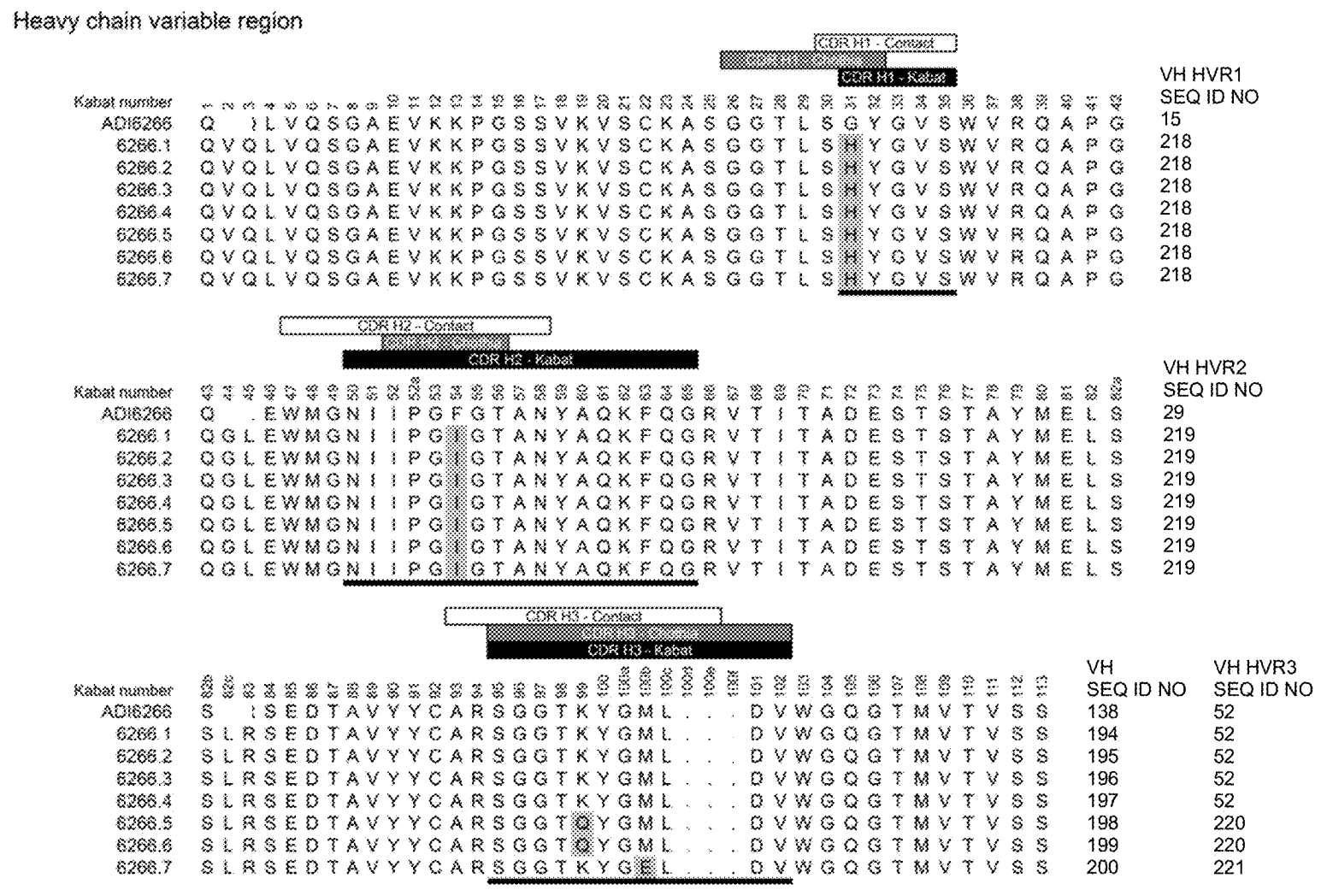

FIG. 12A-B show the (A) light chain variable region sequences and (B) heavy chain variable region sequences of the affinity-matured variants 1-7 of antibody 6266.

Figure 13B:
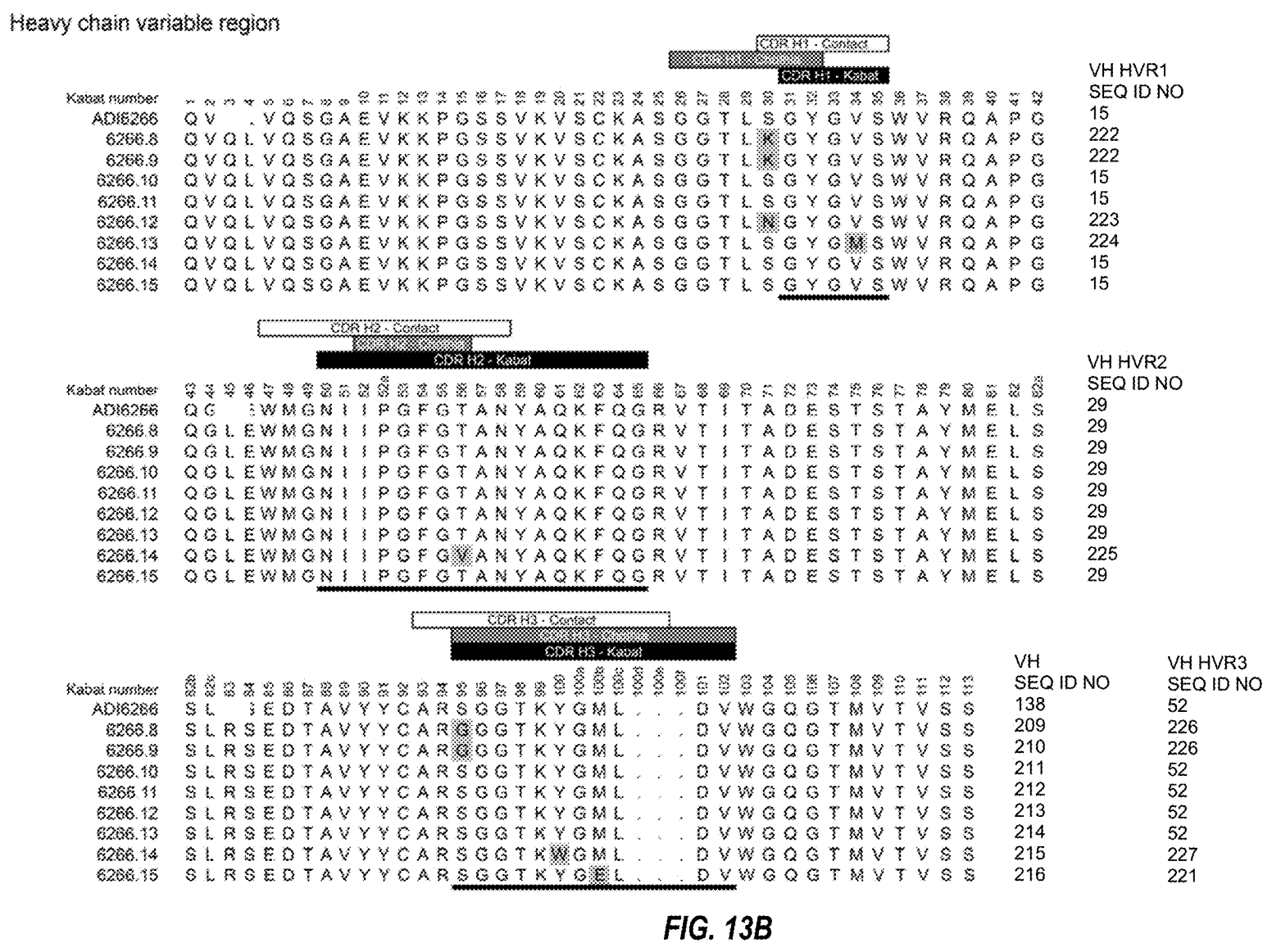

FIG. 13A-B show the (A) light chain variable region sequences and (B) heavy chain variable region sequences of the affinity-matured variants 8-15 of antibody 6266.

FIG. 14 shows affinity constants and melting temperature for the affinity-matured variants of antibody 6266.

DETAILED DESCRIPTION OF EMBODIMENTS OF THE INVENTION

I. Definitions

Figure 9:
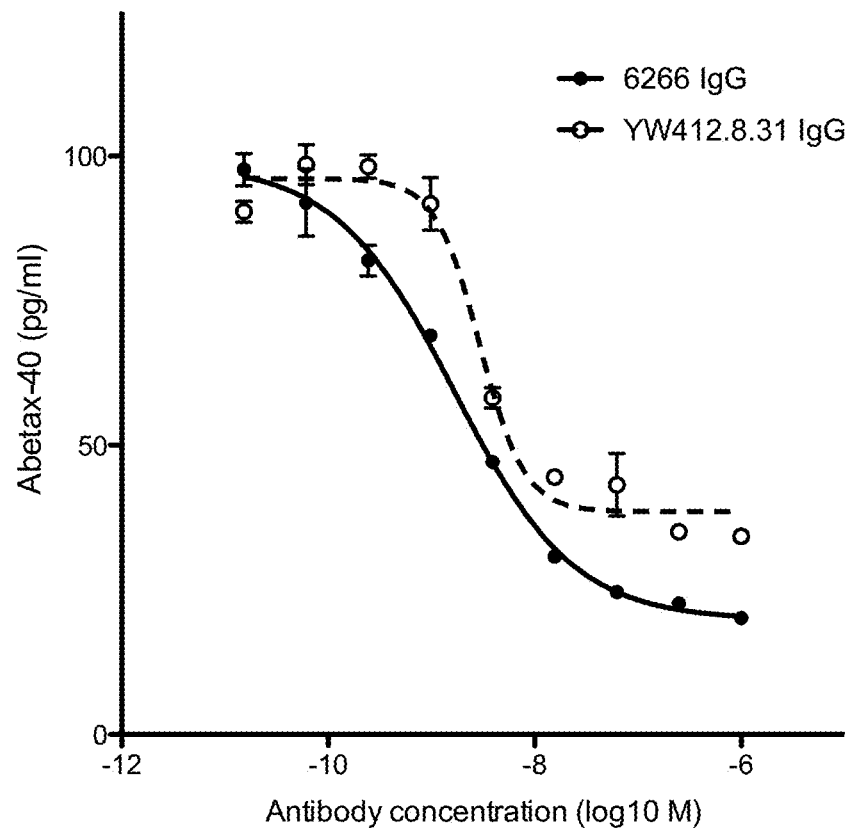
FIG. 9 shows the effects of the indicated anti-BACE1 antibodies on processing of endogenous amyloid precursor protein (APP). Experiments were performed using cultures of E16.5 cortical neurons from wild-type CD1 mice.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-beta-secretase antibody", "anti-BACE1 antibody", "an antibody that binds to beta-secretase" and "an antibody that binds to BACE1" refer to an antibody that is capable of binding BACE1 with sufficient affinity such that the antibody is useful as a diagnostic and/or therapeutic agent in targeting BACE1. In some embodiments, the extent of binding of an anti-BACE1 antibody to an unrelated, non-BACE1 protein is less than about 10% of the binding of the antibody to BACE1 as measured, e.g., by a radioimmunoassay (RIA). In certain embodiments, an antibody that binds to BACE1 has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$M). In certain embodiments, an anti-BACE1 antibody binds to an epitope of BACE1 that is conserved among BACE1 from different species and isoforms.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In some embodiments, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, MH Publication 91-3242, Bethesda Md. (1991), vols. 1-3. In some embodiments, for the VL, the subgroup is subgroup kappa I as in Kabat et al., supra. In some embodiments, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-BACE1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "BACE1," as used herein, refers to any native beta-secretase 1 (also called β-site amyloid precursor protein cleaving enzyme 1, membrane-associated aspartic protease 2, memapsin 2, aspartyl protease 2 or Asp2) from any vertebrate source, including mammals such as primates (e.g. humans) and rodents (e.g., mice and rats), unless otherwise indicated. The term encompasses "full-length," unprocessed BACE1 as well as any form of BACE1 that results from processing in the cell. The term also encompasses naturally occurring variants of BACE1, e.g., splice variants or allelic variants. The amino acid sequence of an exemplary BACE1 polypeptide is shown in SEQ ID NO:179 below, and is the sequence for human BACE1, isoform A as reported in Vassar et al., Science 286:735-741 (1999), which is incorporated herein by reference in its entirety.

```
                                          (SEQ ID NO: 179)
MAQALPWLLLWMGAGVLPAHGTQHGIRLPLRSGLGGAPLGLRLPRETDE

EPEEPGRRGSFVEMVDNLRGKSGQGYYVEMTVGSPPQTLNILVDTGSSN

FAVGAAPHPFLHRYYQRQLSSTYRDLRKGVYVPYTQGKWEGELGTDLVS

IPHGPNVTVRANIAAITESDKFFINGSNWEGILGLAYAEIARPDDSLEP

FFDSLVKQTHVPNLFSLQLCGAGFPLNQSEVLASVGGSMIIGGIDHSLY

TGSLWYTPIRREWYYEVIIVRVEINGQDLKMDCKEYNYDKSIVDSGTTN

LRLPKKVFEAAVKSIKAASSTEKFPDGFWLGEQLVCWQAGTTPWNIFPV

ISLYLMGEVTNQSFRITILPQQYLRPVEDVATSQDDCYKFAISQSSTGT

VMGAVIMEGFYVVFDRARKRIGFAVSACHVHDEFRTAAVEGPFVTLDME

DCGYNIPQTDESTLMTIAYVMAAICALFMLPLCLMVCQWCCLRCLRQQH

DDFADDISLLK
```

Several other isoforms of human BACE1 exist including isoforms B, C and D. See UniProtKB/Swiss-Prot Entry P56817, which is incorporated herein by reference in its entirety. Isoform B is shown in SEQ ID NO:180 and differs from isoform A (SEQ ID NO:179) in that it is missing amino acids 190-214 (i.e. deletion of amino acids 190-214 of SEQ ID NO:179). Isoform C is shown in SEQ ID NO:181 and differs from isoform A (SEQ ID NO:179) in that it is missing amino acids 146-189 (i.e. deletion of amino acids 146-189 of (SEQ ID NO:179). Isoform D is shown in SEQ ID NO:182 and differs from isoform A (SEQ ID NO:179) in that it is missing amino acids 146-189 and 190-214 (i.e. deletion of amino acids 146-189 and 190-214 of SEQ ID NO:179).

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "neurological disorder" or "neurological disease" refer to or describe a disease or disorder of the central and/or peripheral nervous system in mammals. Examples of neurological disorders include, but are not limited to the following list of disease and disorders. Neuropathy disorders are diseases or abnormalities of the nervous system characterized by inappropriate or uncontrolled nerve signaling or lack thereof, and include, but are not limited to, chronic pain (including nociceptive pain (pain caused by an injury to body tissues, including cancer-related pain), neuropathic pain (pain caused by abnormalities in the nerves, spinal cord, or brain), and psychogenic pain (entirely or mostly related to a psychological disorder), headache, migraine, neuropathy, and symptoms and syndromes often accompanying such neuropathy disorders such as vertigo or nausea. Amyloidoses are a group of diseases and disorders associated with extracellular proteinaceous deposits in the CNS, including, but not limited to, secondary amyloidosis, age-related amyloidosis, Alzheimer's Disease (AD), mild cognitive impairment (MCI), Lewy body dementia, Down's syndrome, hereditary cerebral hemorrhage with amyloidosis (Dutch type); the Guam Parkinson-Dementia complex, cerebral amyloid angiopathy, Huntington's disease, progressive supranuclear palsy, multiple sclerosis; Creutzfeld Jacob disease, Parkinson's disease, transmissible spongiform encephalopathy, HIV-related dementia, amyotropic lateral sclerosis (ALS), inclusion-body myositis (IBM), and ocular diseases relating to beta-amyloid deposition (i.e., macular degeneration, drusen-related optic neuropathy, and cataract). Cancers of the CNS are characterized by aberrant proliferation of one or more CNS cell (i.e., a neural cell) and include, but are not limited to, glioma, glioblastoma multiforme, meningioma, astrocytoma, acoustic neuroma, chondroma, oligodendroglioma, medulloblastomas, ganglioglioma, Schwannoma, neurofibroma, neuroblastoma, and extradural, intramedullary or intradural tumors. Ocular diseases or disorders are diseases or disorders of the eye, which for the purposes herein is considered a CNS organ subject to the BBB. Ocular diseases or disorders include, but are not limited to, disorders of sclera, cornea, iris and ciliary body (i.e., scleritis, keratitis, corneal ulcer, corneal abrasion, snow blindness, arc eye, Thygeson's superficial punctate keratopathy, corneal neovascularisation, Fuchs' dystrophy, keratoconus, keratoconjunctivitis sicca, iritis and uveitis), disorders of the lens (i.e., cataract), disorders of choroid and retina (i.e., retinal detachment, retinoschisis, hypertensive retinopathy, diabetic retinopathy, retinopathy, retinopathy of prematurity, age-related macular degeneration, macular degeneration (wet or dry), epiretinal membrane, retinitis pigmentosa and macular edema), glaucoma, floaters, disorders of optic nerve and visual pathways (i.e., Leber's hereditary optic neuropathy and optic disc drusen), disorders of ocular muscles/binocular movement accommodation/refraction (i.e., strabismus, ophthalmoparesis, progressive external opthalmoplegia, esotropia, exotropia, hypermetropia, myopia, astigmatism, anisometropia, presbyopia and ophthalmoplegia), visual disturbances and blindness (i.e., amblyopia, Lever's congenital amaurosis, scotoma, color blindness, achromatopsia, nyctalopia, blindness, river blindness and micro-opthalmia/coloboma), red eye, Argyll Robertson pupil, keratomycosis, xerophthalmia and andaniridia. Viral or microbial infections of the CNS include, but are not limited to, infections by viruses (i.e., influenza, HIV, poliovirus, rubella), bacteria (i.e., *Neisseria* sp., *Streptococcus* sp., *Pseudomonas* sp., *Proteus* sp., *E. coli, S. aureus, Pneumococcus* sp., *Meningococcus* sp., *Haemophilus* sp., and *Mycobacterium tuberculosis*) and other microorganisms such as fungi (i.e., yeast, *Cryptococcus neoformans*), parasites (i.e., *Toxoplasma gondii*) or amoebas resulting in CNS pathophysiologies including, but not limited to, meningitis, encephalitis, myelitis, vasculitis and abscess, which can be acute or chronic. Inflammation of the CNS is inflammation that is caused by an injury to the CNS, which can be a physical injury (i.e., due to accident, surgery, brain trauma, spinal cord injury, concussion) or an injury due to or related to one or more other diseases or disorders of the CNS (i.e., abscess, cancer, viral or microbial infection). Ischemia of the CNS, as used herein, refers to a group of disorders relating to aberrant blood flow or vascular behavior in the brain or the causes therefor, and includes, but is not limited to, focal brain ischemia, global brain ischemia, stroke (i.e., subarachnoid hemorrhage and intracerebral hemorrhage), and aneurysm. Neurodegenerative diseases are a group of diseases and disorders associated with neural cell loss of function or death in the CNS, and include, but are not limited to, adrenoleukodystrophy, Alexander's disease, Alper's disease, amyotrophic lateral sclerosis, ataxia telangiectasia, Batten disease, cockayne syndrome, corticobasal degeneration, degeneration caused by or associated with an amyloidosis, Friedreich's ataxia, frontotemporal lobar degeneration, Kennedy's disease, multiple system atrophy, multiple sclerosis, primary lateral sclerosis, progressive supranuclear palsy, spinal muscular atrophy, transverse myelitis, Refsum's disease, and spinocerebellar ataxia. Seizure diseases and disorders of the CNS involve inappropriate and/or abnormal electrical conduction in the CNS, and include, but are not limited to, epilepsy (i.e., absence seizures, atonic seizures, benign Rolandic epilepsy, childhood absence, clonic seizures, complex partial seizures, frontal lobe epilepsy, febrile seizures, infantile spasms, juvenile myoclonic epilepsy, juvenile absence epilepsy, Lennox-Gastaut syndrome, Landau-Kleffner Syndrome, Dravet's syndrome, Otahara syndrome, West syndrome, myoclonic seizures, mitochondrial disorders, progressive myoclonic epilepsies, psychogenic seizures, reflex epilepsy, Rasmussen's Syndrome, simple partial seizures, secondarily generalized seizures, temporal lobe epilepsy, toniclonic seizures, tonic seizures, psychomotor seizures, limbic epilepsy, partial-onset seizures, generalized-onset seizures, status epilepticus, abdominal epilepsy, akinetic seizures, autonomic seizures, massive bilateral myoclonus, catamenial epilepsy, drop seizures, emotional seizures, focal seizures, gelastic seizures, Jacksonian March, Lafora Disease, motor seizures, multifocal seizures, nocturnal seizures, photosensitive seizure, pseudo seizures, sensory seizures, subtle seizures, sylvan seizures, withdrawal seizures, and visual reflex seizures)Behavioral disorders are disorders of the CNS characterized by aberrant behavior on the part of the afflicted subject and include, but are not limited to, sleep disorders (i.e., insomnia, parasomnias, night terrors, circadian rhythm sleep disorders, and narcolepsy), mood disorders (i.e., depression, suicidal depression, anxiety, chronic affective disorders, phobias, panic attacks, obsessive-compulsive disorder, attention deficit hyperactivity disorder (ADHD), attention deficit disorder (ADD), chronic fatigue syndrome, agoraphobia, post-traumatic stress disorder, bipolar disorder), eating disorders (i.e., anorexia or bulimia), psychoses, developmental behavioral disorders (i.e., autism, Rett's syndrome, Aspberger's syndrome), personality disorders and psychotic disorders (i.e., schizophrenia, delusional disorder, and the like). Lysosomal storage disorders are metabolic disorders which are in some cases associated with the CNS or have CNS-specific symptoms; such disorders include, but are not limited to Tay-Sachs disease, Gaucher's disease, Fabry disease, mucopolysaccharidosis (types I, II, III, IV, V, VI and VII), glycogen storage disease, GM1-gangliosidosis, metachromatic leukodystrophy, Farber's disease, Canavan's leukodystrophy, and neuronal ceroid lipofuscinoses types 1 and 2, Niemann-Pick disease, Pompe disease, and Krabbe's disease.

II. COMPOSITIONS AND METHODS

In some aspects, the invention is based, in part, on antibodies which bind BACE1 and reduce and/or inhibit BACE1 activity. In certain embodiments, antibodies that bind to the active site or an exosite of BACE1 are provided.

A. Exemplary Anti-BACE1 Antibodies

In some embodiments, anti-BACE1 antibodies are provided. In some embodiments, an anti-BACE1 antibody provided herein is an allosteric inhibitor of BACE1 activity. Nonlimiting exemplary anti-BACE1 antibodies include antibodies comprising the heavy chain and light chain variable regions of the antibodies listed in Table 1. The heavy and light chain variable regions of the antibodies listed in Table 1 are shown in FIGS. 3 and 4, respectively.

TABLE 1

| Anti-BACE1 Antibodies | | | | | |
|---|---|---|---|---|---|
| Ab | Ab | Ab | Ab | Ab | Ab |
| 5531 | 5572 | 5893 | 6290 | 6311 | 5987 |
| 5586 | 5536 | 5887 | 6291 | 6309 | 6303 |
| 5583 | 5571 | 6275 | 6293 | 6310 | 6266 |
| 5532 | 5883 | 6279 | 6289 | 6308 | 6271 |
| 5592 | 5890 | 6276 | 5747 | 5990 | 6297 |
| 5878 | 5891 | 5888 | 5982 | 6307 | 6294 |
| 5874 | 5892 | 5894 | 5985 | 5931 | 5932 |
| 5875 | 5884 | 5543 | 5983 | 6298 | 6313 |
| 5876 | 6272 | 5643 | 5984 | 5930 | 6314 |
| 5880 | 6270 | 5644 | 5986 | 5988 | 6315 |
| 5881 | 6273 | 5896 | 6296 | 6299 | 5933 |
| 5260 | 6274 | 5902 | 5897 | 6300 | 6285 |
| 6288 | 5539 | 5903 | 5905 | 6305 | 6280 |
| 6266.1 | 6266.2 | 6266.3 | 6266.4 | 6266.5 | 6266.6 |
| 6266.7 | 6266.8 | 6266.9 | 6266.10 | 6266.11 | 6266.12 |
| 6266.13 | 6266.14 | 6266.15 | | | |

In some embodiments, an anti-BACE1 antibody described herein, including but not limited to antibodies comprising one or more HVRs, or all six HVRs, of an antibody listed in Table 1, is an allosteric inhibitor of BACE1 activity. In some embodiments, an anti-BACE1 antibody binds BACE1 with an affinity ($K_D$) of less than 10 nM, less than 9 nM, less than 8 nM, less than 7 nM, less than 6 nM, less than 5 nM, less than 4 nM, or less than 3 nM, as measured by surface plasmon resonance (SPR). In some embodiments, an anti-BACE1 antibody binds BACE1 with an affinity ($K_D$) of between 0.1 nM and 10 nM, or between 0.1 nM and 8 nM, or between 0.1 nM and 7 nM, or between 0.1 nM and 5 nM, or between 0.5 nM and 5 nM, or between 0.1 nM and 3 nM, or between 0.5 nM and 3 nM, as measured by surface plasmon resonance (SPR). In some embodiments, an anti-BACE1 antibody achieves a maximum inhibition of BACE1 activity of greater than 60%, greater than 70%, greater than 75%, or greater than 80%, as measured, for example, using the dissociated cortical neuron culture assay described in Example 2E.

In some aspects, the invention provides an anti-BACE1 antibody comprising at least one, two, three, four, five, or six HVRs of an antibody selected from the anti-BACE1 antibodies listed in Table 1. FIGS. 1 and 2 show the heavy chain and light chain HVR sequences, respectively, of each of those antibodies. In some embodiments, the invention provides an anti-BACE1 antibody comprising HVR-H1, HVR-H2, HVR-H3, HVR-L1, HVR-L2, and HVR-L3 of an antibody selected from the anti-BACE1 antibodies listed in Table 1.

In some embodiments, an anti-BACE1 antibody is provided, wherein the antibody comprises an HVR-H1 sequence selected from SEQ ID NOs: 1 to 6; an HVR-H2 sequence selected from SEQ ID NOs: 22 to 25; an HVR-H3 sequence selected from SEQ ID NOs: 50 and 51; an HVR-L1 sequence selected from SEQ ID NOs: 62 and 63; an HVR-L2 sequence selected from SEQ ID NOs: 69 and 70; and an HVR-L3 sequence selected from SEQ ID NOs: 75 to 78 and 98. In some embodiments, an anti-BACE1 antibody is provided, wherein the antibody comprises an HVR-H1 sequence selected from SEQ ID NOs: 7 to 21, 218, and 222 to 224; an HVR-H2 sequence selected from SEQ ID NOs: 26 to 49, 232, 219, and 225; an HVR-H3 sequence selected from SEQ ID NOs: 52 to 61, 220, 221, 226, and 227; an HVR-L1 sequence selected from SEQ ID NOs: 64 to 68; an HVR-L2 sequence selected from SEQ ID NOs: 69 to 74 and 217; and an HVR-L3 sequence selected from SEQ ID NOs: 79 to 97. In some embodiments, an anti-BACE1 antibody is provided, wherein the antibody comprises an HVR-H1 sequence selected from SEQ ID NOs: 15, 218, and 222 to 224; an HVR-H2 sequence selected from SEQ ID NOs: 29, 219, and 255; an HVR-H3 sequence selected from SEQ ID NOs: 52, 220, 221, 226, and 227; an HVR-L1 sequence of SEQ ID NO: 65; an HVR-L2 sequence selected from SEQ ID NOs: 71, 73, and 217; and an HVR-L3 sequence of SEQ ID NO: 80. In some embodiments, an anti-BACE1 antibody is provided, wherein the antibody comprises an HVR-H1 of SEQ ID NO: 15; an HVR-H2 sequence of SEQ ID NO: 29; an HVR-H3 sequence of SEQ ID NO: 52; an HVR-L1 sequence of SEQ ID NO: 65; an HVR-L2 sequence of SEQ ID NO: 71; and an HVR-L3 sequence of SEQ ID NO: 80. In some embodiments, an anti-BACE1 antibody is provided, wherein the antibody comprises an HVR-H1, HVR-H2, HVR-H3, HVR-L1, HVR-L2, and HVR-L3 of an antibody selected from antibody 6266 variants 1-15.

In some aspects, the invention provides an antibody comprising at least one, at least two, or all three VH HVR sequences selected of an antibody selected from the anti-BACE1 antibodies listed in Table 1. In some embodiments, the invention provides an antibody comprising HVR-H1, HVR-H2, and HVR-H3 of an antibody selected from the anti-BACE1 antibodies listed in Table 1. In some embodiments, an anti-BACE1 antibody is provided, wherein the antibody comprises an HVR-H1 sequence selected from SEQ ID NOs: 1 to 6; an HVR-H2 sequence selected from SEQ ID NOs: 22 to 25; and an HVR-H3 sequence selected from SEQ ID NOs: 50 and 51. In some embodiments, an anti-BACE1 antibody is provided, wherein the antibody comprises an HVR-H1 sequence selected from SEQ ID NOs: 7 to 21, 218, and 222 to 224; and HVR-H2 sequence selected from SEQ ID NOs: 26 to 49, 232, 219, and 225; and an HVR-H3 sequence selected from SEQ ID NOs: 52 to 61, 220, 221, 226, and 227. In some embodiments, an anti-BACE1 antibody is provided, wherein the antibody comprises an HVR-H1 sequence selected from SEQ ID NOs: 15, 218, and 222 to 224; an HVR-H2 sequence selected from SEQ ID NOs: 29, 219, and 255; and an HVR-H3 sequence selected from SEQ ID NOs: 52, 220, 221, 226, and 227. In some embodiments, an anti-BACE1 antibody is provided, wherein the antibody comprises an HVR-H1 of SEQ ID NO: 15; an HVR-H2 sequence of SEQ ID NO: 29; and an HVR-H3 sequence of SEQ ID NO: 52. In some embodiments, an anti-BACE1 antibody is provided, wherein the antibody comprises an HVR-H1, HVR-H2, and HVR-H3 of an antibody selected from antibody 6266 variants 1-15.

In some aspects, the invention provides an antibody comprising at least one, at least two, or all three VL HVR sequences selected of an antibody selected from the anti-BACE1 antibodies listed in Table 1. In some embodiments, the invention provides an antibody comprising HVR-L1, HVR-L2, and HVR-L3 of an antibody selected from the anti-BACE1 antibodies listed in Table 1. In some embodiments, an anti-BACE1 antibody is provided, wherein the antibody comprises an HVR-L1 sequence selected from SEQ ID NOs: 62 and 63; an HVR-L2 sequence selected from SEQ ID NOs: 69 and 70; and an HVR-L3 sequence selected from SEQ ID NOs: 75 to 78 and 98. In some embodiments, an anti-BACE1 antibody is provided, wherein the antibody comprises an HVR-L1 sequence selected from SEQ ID NOs: 64 to 68; an HVR-L2 sequence selected from SEQ ID NOs: 69 to 74 and 217; and an HVR-L3 sequence selected from SEQ ID NOs: 79 to 97. In some embodiments, an anti-BACE1 antibody is provided, wherein the antibody comprises an HVR-L1 sequence of SEQ ID NO: 65; an HVR-L2 sequence of SEQ ID NO: 71, 73, or 217; and an HVR-L3 sequence of SEQ ID NO: 80. In some embodiments, an anti-BACE1 antibody is provided, wherein the antibody comprises an HVR-L1 sequence of SEQ ID NO: 65; an HVR-L2 sequence of SEQ ID NO: 71; and an HVR-L3 sequence of SEQ ID NO: 80. In some embodiments, an anti-BACE1 antibody is provided, wherein the antibody comprises an HVR-L1, HVR-L2, and HVR-L3 of an antibody selected from antibody 6266 variants 1-15.

In another aspect, a heavy chain is provided, comprising a VH domain comprising at least one, at least two, or all three VH HVR sequences of an antibody selected from the anti-BACE1 antibodies listed in Table 1. In some embodiments, a heavy chain is provided, comprising a VH domain comprising all three VH HVR sequences of an antibody selected from the anti-BACE1 antibodies listed in Table 1. In another aspect, a heavy chain is provided, comprising a VH domain comprising an HVR-H1 sequence selected from SEQ ID NOs: 1 to 6; an HVR-H2 sequence selected from SEQ ID NOs: 22 to 25; and an HVR-H3 sequence selected from SEQ ID NOs: 50 and 51. In another aspect, a heavy chain is provided, comprising a VH domain comprising an HVR-H1 sequence selected from SEQ ID NOs: 7 to 21, 218, and 222 to 224; and HVR-H2 sequence selected from SEQ ID NOs: 26 to 49, 232, 219, and 225; and an HVR-H3 sequence selected from SEQ ID NOs: 52 to 61, 220, 221, 226, and 227. In some embodiments, a heavy chain is provided, comprising a VH domain comprising an HVR-H1 sequence selected from SEQ ID NOs: 15, 218, and 222 to 224; an HVR-H2 sequence selected from SEQ ID NOs: 29, 219, and 255; and an HVR-H3 sequence selected from SEQ ID NOs: 52, 220, 221, 226, and 227. In some embodiments, a heavy chain is provided, comprising a VH domain comprising an HVR-H1 of SEQ ID NO: 15; an HVR-H2 sequence of SEQ ID NO: 29; and an HVR-H3 sequence of SEQ ID NO: 52. In some embodiments, a heavy chain is provided, comprising a VH domain comprising an HVR-H1, HVR-H2, and HVR-H3 of an antibody selected from antibody 6266 variants 1-15.

In another aspect, a light chain is provided, comprising a VL domain comprising at least one, at least two, or all three VL HVR sequences of an antibody selected from the anti-BACE1 antibodies listed in Table 1. In some embodiments, a light chain is provided, comprising a VL domain comprising all three VL HVR sequences of an antibody selected from the anti-BACE1 antibodies listed in Table 1. In another aspect, a light chain is provided, comprising a VL domain comprising an HVR-L1 sequence selected from SEQ ID NOs: 62 and 63; an HVR-L2 sequence selected from SEQ ID NOs: 69 and 70; and an HVR-L3 sequence selected from SEQ ID NOs: 75 to 78 and 98. In another aspect, a light chain is provided, comprising a VL domain comprising an HVR-L1 sequence selected from SEQ ID NOs: 64 to 68; an HVR-L2 sequence selected from SEQ ID NOs: 69 to 74 and 217; and an HVR-L3 sequence selected from SEQ ID NOs: 79 to 97. In some embodiments, a light chain is provided, comprising a VL domain comprising an HVR-L1 sequence of SEQ ID NO: 65; an HVR-L2 sequence of SEQ ID NO: 71, 73, or 217; and an HVR-L3 sequence of SEQ ID NO: 80. In some embodiments, a light chain is provided, comprising a VL domain comprising an HVR-L1 sequence of SEQ ID NO: 65; an HVR-L2 sequence of SEQ ID NO: 71; and an HVR-L3 sequence of SEQ ID NO: 80. In some embodiments, a light chain is provided, comprising a VL domain comprising an HVR-L1, HVR-L2, and HVR-L3 of an antibody selected from antibody 6266 variants 1-15.

In another aspect, an anti-BACE1 antibody comprises a heavy chain variable domain (VH) sequence having at least 90%, 91%, 92%, 93%, 94%, 95%, 96%, 97%, 98%, 99%, or 100% sequence identity to the VH of an anti-BACE1 antibody of Table 1. In some embodiments, an anti-BACE1 antibody comprises a heavy chain variable domain (VH) sequence having at least 90%, 91%, 92%, 93%, 94%, 95%, 96%, 97%, 98%, 99%, or 100% sequence identity to an amino acid sequence selected from SEQ ID NOs: 99 to 147, 194 to 200, and 209 to 216. In some embodiments, an anti-BACE1 antibody comprises a heavy chain variable domain (VH) sequence having at least 90%, 91%, 92%, 93%, 94%, 95%, 96%, 97%, 98%, 99%, or 100% sequence identity to the amino acid sequence selected from SEQ ID NOs: 138, 194 to 200, and 209 to 216. In some embodiments, an anti-BACE1 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 138. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-BACE1 antibody comprising that sequence retains the ability to bind to BACE1 and/or inhibit or reduce BACE1 activity. In certain embodiments, a total of 1 to 10 amino acids have been substituted, inserted and/or deleted in any one of SEQ ID NO: 99 to 147. In certain embodiments, substitutions, insertions, or deletions occur in regions outside the HVRs (i.e., in the FRs). Optionally, the anti-BACE1 antibody comprises the VH sequence in any one of SEQ ID NO: 99 to 147, 194 to 200, and 209 to 216, including post-translational modifications of that sequence. In a particular embodiment, the VH comprises one, two or three HVRs of an anti-BACE1 antibody listed in Table 1. In some embodiments, the VH comprises an HVR-H1 sequence selected from SEQ ID NOs: 1 to 6; an HVR-H2 sequence selected from SEQ ID NOs: 22 to 25; and an HVR-H3 sequence selected from SEQ ID NOs: 50 and 51. In some embodiments, the VH comprises an HVR-H1 sequence selected from SEQ ID NOs: 7 to 21, 218, and 222 to 224; and HVR-H2 sequence selected from SEQ ID NOs: 26 to 49, 232, 219, and 225; and an HVR-H3 sequence selected from SEQ ID NOs: 52 to 61, 220, 221, 226, and 227. In some embodiments, the VH comprises an HVR-H1 sequence selected from SEQ ID NOs: 15, 218, and 222 to 224; an HVR-H2 sequence selected from SEQ ID NOs: 29, 219, and 255; and an HVR-H3 sequence selected from SEQ ID NOs: 52, 220, 221, 226, and 227. In some embodiments, the VH comprises an HVR-H1 of SEQ ID NO: 15; an HVR-H2 sequence of SEQ ID NO: 29; and an HVR-H3 sequence of SEQ ID NO: 52. In some embodiments, the VH comprises an HVR-H1, HVR-H2, and HVR-H3 of an antibody selected from antibody 6266 variants 1-15.

In another aspect, an anti-BACE1 antibody comprises a light chain variable domain (VL) sequence having at least 90%, 91%, 92%, 93%, 94%, 95%, 96%, 97%, 98%, 99%, or 100% sequence identity to the VL of an anti-BACE1 antibody of Table 1. In another aspect, an anti-BACE1 antibody is provided, wherein the antibody comprises a light chain variable domain (VL) having at least 90%, 91%, 92%, 93%, 94%, 95%, 96%, 97%, 98%, 99%, or 100% sequence identity to an amino acid sequence selected from SEQ ID NOs: 148 to 178, 187 to 194, and 201 to 208. In some embodiments, an anti-BACE1 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 156. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-BACE1 antibody comprising that sequence retains the ability to bind to BACE1 and/or inhibit or reduce BACE1 activity. In certain embodiments, a total of 1 to 10 amino acids have been substituted, inserted and/or deleted in any one of SEQ ID NOs: 148 to 178, 187 to 194, and 201 to 208. In certain embodiments, the substitutions, insertions, or deletions occur in regions outside the HVRs (i.e., in the FRs). Optionally, the anti-BACE1 antibody comprises the VL sequence in any one of SEQ ID NOs: 148 to 178, 187 to 194, and 201 to 208, including post-translational modifications of that sequence. In a particular embodiment, the VL comprises one, two or three HVRs of an anti-BACE1 antibody listed in Table 1. In some embodiments, the VL comprises an HVR-L1 sequence selected from SEQ ID NOs: 62 and 63; an HVR-L2 sequence selected from SEQ ID NOs: 69 and 70; and an HVR-L3 sequence selected from SEQ ID NOs: 75 to 78 and 98. In some embodiments, the VL comprises an HVR-L1 sequence selected from SEQ ID NOs: 64 to 68; an HVR-L2 sequence selected from SEQ ID NOs: 69 to 74 and 217; and an HVR-L3 sequence selected from SEQ ID NOs: 79 to 97. In some embodiments, the VL comprises an HVR-L1 sequence of SEQ ID NO: 65; an HVR-L2 sequence of SEQ ID NO: 71, 73, or 217; and an HVR-L3 sequence of SEQ ID NO: 80. In some embodiments, the VL comprises an HVR-L1 sequence of SEQ ID NO: 65; an HVR-L2 sequence of SEQ ID NO: 71; and an HVR-L3 sequence of SEQ ID NO: 80. In some embodiments, the VL comprises an HVR-L1, HVR-L2, and HVR-L3 of an antibody selected from antibody 6266 variants 1-15.

In another aspect, an anti-BACE1 antibody is provided, wherein the antibody comprises a VH as in any of the embodiments provided above, and a VL as in any of the embodiments provided above. In some embodiments, an anti-BACE1 antibody is provided, wherein the antibody comprises a VH sequence selected from SEQ ID NOs: 99 to 106 and a VL sequence selected from SEQ ID NOs: 148 to 152. In some embodiments, an anti-BACE1 antibody is provided, wherein the antibody comprises a VH sequence selected from SEQ ID NOs: 107 to 147, 194 to 200, and 209 to 216, and a VL sequence selected from SEQ ID NOs: 153 to 178, 187 to 194, and 201 to 208. In some embodiments, an anti-BACE1 antibody is provided, wherein the antibody comprises a VH and a VL of an anti-BACE1 antibody listed in Table 1. In some embodiments, the antibody comprises a VH sequence selected from SEQ ID NOs: 138, 194 to 200, and 209 to 216, and a VL sequence selected from SEQ ID NO: 156, 187 to 194, and 201 to 208, including post-translational modifications of those sequences. In some embodiments, the antibody comprises the VH and VL sequences of SEQ ID NO: 138 and SEQ ID NO: 156, respectively, including post-translational modifications of those sequences. In some embodiments, an anti-BACE1 antibody is provided, wherein the antibody comprises a VH and a VL of an antibody selected from antibody 6266 variants 1-15.

In a further aspect, the invention provides an antibody that binds to the same epitope as an anti-BACE1 antibody provided herein, such as the anti-BACE1 antibodies listed in Table 1. For example, in certain embodiments, an antibody is provided that binds to the same epitope as an anti-BACE1 antibody comprising a VH sequence selected from SEQ ID NOs: 99 to 106 and a VL sequence selected from SEQ ID NOs: 148 to 152. In certain embodiments, an antibody is provided that binds to the same epitope as an anti-BACE1 antibody comprising a VH sequence selected from SEQ ID NOs: 107 to 147, 194 to 200, and 209 to 216, and a VL sequence selected from SEQ ID NOs: 153 to 178, 187 to 194, and 201 to 208. In certain embodiments, an antibody is provided that binds to the same epitope as an anti-BACE1 antibody comprising the VH and VL sequences of SEQ ID NO: 138 and SEQ ID NO: 156, respectively.

In another embodiment, an antibody is provided that competes for binding (e.g., binds to the same epitope) as any anti-BACE1 antibody described herein.

In a further aspect of the invention, an anti-BACE1 antibody according to any of the above embodiments is a monoclonal antibody, including a chimeric or human antibody. In some embodiments, an anti-BACE1 antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, an anti-BACE1 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

In some embodiments, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Natl. Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for BACE1 and the other is for any other antigen. In certain embodiments, bispecific antibodies may bind to two different epitopes of BACE1. Bispecific antibodies may also be used to localize cytotoxic agents to cells which express BACE1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to BACE1 as well as another, different antigen (see, US 2008/069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 2 under the heading of "conservative substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Original Residue | Exemplary Substitutions | Preferred Substitutions |
| --- | --- | --- |
| Ala (A) | Val; Leu; Ile | Val |
| Arg (R) | Lys; Gin; Asn | Lys |

TABLE 2-continued

| Original Residue | Exemplary Substitutions | Preferred Substitutions |
| --- | --- | --- |
| Asn (N) | Gln; His; Asp, Lys; Arg | Gin |
| Asp (D) | Glu; Asn | Glu |
| Cys (C) | Ser; Ala | Ser |
| Gln (Q) | Asn; Glu | Asn |
| Glu (E) | Asp; Gin | Asp |
| Gly (G) | Ala | Ala |
| His (H) | Asn; Gin; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gin; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Natl. Acad. Sci. USA* 83:7059-7063 (1986)) and Hellstrom, I et al., *Proc. Natl. Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Natl. Acad. Sci.* USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Intl. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816, 567. In some embodiments, isolated nucleic acid encoding an anti-BACE1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In some embodiments, the host cell is eukaryotic, e.g. a Chinese Hamster Ovary (CHO) cell or lymphoid cell (e.g., Y0, NS0, Sp20 cell). In some embodiments, a method of making an anti-BACE1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-BACE1 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-BACE1 antibodies provided herein may be identified, screened for, or characterized for their physical/chemical properties and/or biological activities by various assays known in the art.

1. Binding Assays and Other Assays

In some aspects, an antibody of the invention is tested for its antigen binding activity, e.g., by known methods such as ELISA, Western blot, etc.

In another aspect, competition assays may be used to identify an antibody that competes with any of the anti-BACE1 antibodies described herein for binding to BACE1. In certain embodiments, such a competing antibody binds to the same epitope (e.g., a linear or a conformational epitope) that is bound by any of the antibodies descried herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized BACE1 is incubated in a solution comprising a first labeled antibody that binds to BACE1 (e.g., an anti-BACE1 antibody described herein) and a second unlabeled antibody that is being tested for its ability to compete with the first antibody for binding to BACE1. The second antibody may be present in a hybridoma supernatant. As a control, immobilized BACE1 is incubated in a solution comprising the first labeled antibody but not the second unlabeled antibody. After incubation under conditions permissive for binding of the first antibody to BACE1, excess unbound antibody is removed, and the amount of label associated with immobilized BACE1 is measured. If the amount of label associated with immobilized BACE1 is substantially reduced in the test sample relative to the control sample, then that indicates that the second antibody is competing with the first antibody for binding to BACE1. See Harlow and Lane (1988) *Antibodies: A Laboratory Manual* ch. 14 (Cold Spring Harbor Laboratory, Cold Spring Harbor, N.Y.).

2. Activity Assays

In some aspects, assays are provided for identifying anti-BACE1 antibodies thereof having biological activity.

Biological activity may include, e.g., inhibition or reduction of BACE1 aspartyl protease activity; or inhibition or reduction in APP cleavage by BACE1; or inhibition or reduction in Aβ production. Antibodies having such biological activity in vivo and/or in vitro are also provided.

In certain embodiments, an antibody of the invention is tested for such biological activity. For example, BACE1 protease activity can be tested in a homogeneous time-resolved fluorescence HTRF assay, as described in detail in the Examples, using synthetic substrate peptides.

Briefly, a homogeneous time-resolved fluorescence (HTRF) assay can be used to measure BACE1 aspartyl protease activity with the use of an amyloid precursor protein BACE1 cleavage site peptide. For example, the Bi27 peptide (Biotin-KTEEISEVNLDAEFRHDSGYEVHHQKL (SEQ ID NO: 183), American Peptide Company)), is combined with BACE1 pre-incubated with an anti-BACE antibody in BACE reaction buffer (50 mM sodium acetate pH 4.4 and 0.1% CHAPS) in a 384-well plate (Proxiplate™, Perkin-Elmer). The proteolytic reaction mixture is incubated at ambient temperature for 75 minutes and was quenched by the addition of 5 μL HTRF detection mixture containing 2 nM Streptavidin-D2 and 150 nM of an anti-amyloid beta antibody labeled with Europium cryptate in detection buffer (200 mM Tris pH 8.0, 20 mM EDTA, 0.1% BSA, and 0.8M KF). The final reaction mixture is incubated at ambient temperature for 60 minutes and the TR-FRET signal is measured using an EnVision Multilabel Plate Reader™ (Perkin-Elmer) at an excitation wavelength of 320 nm and emission wavelengths of 615 and 665 nm.

In some embodiments, BACE1 protease activity may be measured using a microfluidic capillary electrophoretic (MCE) assay. An MCE assay reaction can be carried out in a standard enzymatic reaction, initiated by the addition of substrate to enzyme and 4× compound, containing human BACE1 (extracellular domain), amyloid precursor protein beta secretase active site peptide (FAM-KTEEISEVNL-DAEFRWKK-CONH$_2$ (SEQ ID NO:186)), 50 mM NaOAc pH 4.4 and 0.1% CHAPS. After incubation for 60 minutes at ambient temperature, the product and substrate in each reaction is separated using a 12-sipper microfluidic chip analyzed on an LC3000® (both, Caliper Life Sciences). The separation of product and substrate is optimized by choosing voltages and pressure using the manufacturer's optimization software. Substrate conversion is calculated from the electrophoregram using HTS Well Analyzer software (Caliper Life Sciences).

In addition, BACE1 protease activity can be tested in vivo in cell lines which express BACE1 substrates such as APP, as described in the Examples herein; or in transgenic mice which express BACE1 substrates, such as human APP, as described in PCT Publication No. WO 2012/064836 A1.

Additionally, BACE1 protease activity can be tested with anti-BACE1 antibodies in animal models. For example, animal models of various neurological diseases and disorders, and associated techniques for examining the pathological processes associated with these models, are readily available in the art. Animal models of various neurological disorders include both non-recombinant and recombinant (transgenic) animals. Non-recombinant animal models include, for example, rodent, e.g., murine, models. Such models can be generated by introducing cells into syngeneic mice using standard techniques, e.g. subcutaneous injection, tail vein injection, spleen implantation, intraperitoneal implantation, and implantation under the renal capsule. In vivo models include models of stroke/cerebral ischemia, in vivo models of neurodegenerative diseases, such as mouse models of Parkinson's disease; mouse models of Alzheimer's disease; mouse models of amyotrophic lateral sclerosis; mouse models of spinal muscular atrophy; mouse/rat models of focal and global cerebral ischemia, for instance, common carotid artery occlusion or middle cerebral artery occlusion models; or in ex vivo whole embryo cultures. As one nonlimiting example, there are a number of art-known mouse models for Alzheimer's disease ((see, e.g. Rakover et al., *Neurodegener. Dis.* (2007); 4(5): 392-402; Mouri et al., *FASEB J.* (2007) July; 21 (9): 2135-48; Minkeviciene et al., *J. Pharmacol. Exp. Ther.* (2004) November; 311 (2):677-82 and Yuede et al., *Behav Pharmacol.* (2007) September; 18 (5-6): 347-63). The various assays may be conducted in known in vitro or in vivo assay formats, as known in the art and described in the literature. Various such animal models are also available from commercial vendors such as the Jackson Laboratory.

D. Immunoconjugates

The invention also provides immunoconjugates comprising an anti-BACE1 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some embodiments, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-BACE1 antibodies provided herein is useful for detecting the presence of BACE1 in a biological sample. The term "detecting" as used herein encompasses quantitative or qualitative detection. In certain embodiments, a biological sample comprises a cell or tissue, such as serum, plasma, saliva, gastric secretions, mucus, cerebrospinal fluid, lymphatic fluid, neuronal tissue, brain tissue, cardiac tissue or vascular tissue.

In some embodiments, an anti-BACE1 antibody for use in a method of diagnosis or detection is provided. In a further aspect, a method of detecting the presence of BACE1 in a biological sample is provided. In certain embodiments, the method comprises contacting the biological sample with an anti-BACE1 antibody as described herein under conditions permissive for binding of the anti-BACE1 antibody to BACE1, and detecting whether a complex is formed between the anti-BACE1 antibody and BACE1. Such method may be an in vitro or in vivo method. In some embodiments, an anti-BACE1 antibody is used to select subjects eligible for therapy with an anti-BACE1 antibody, e.g. where BACE1 is a biomarker for selection of patients.

Exemplary disorders that may be diagnosed using an antibody of the invention include neurodegenerative diseases (including, but not limited to, Lewy body disease, postpoliomyelitis syndrome, Shy-Draeger syndrome, olivopontocerebellar atrophy, Parkinson's disease, multiple system atrophy, striatonigral degeneration, tauopathies (including, but not limited to, Alzheimer disease and supranuclear palsy), prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), stroke, muscular dystrophy, multiple sclerosis, Amyotrophic lateral sclerosis (ALS), Angelman's syndrome, Liddle syndrome, Paget's syndrome, traumatic brain injury, bulbar palsy, motor neuron disease, and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia).

In certain embodiments, labeled anti-BACE1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-BACE1 antibody as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In some aspects, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-BACE1 antibodies provided herein may be used in therapeutic methods.

In some aspects, an anti-BACE1 antibody for use as a medicament is provided. In further aspects, an anti-BACE1 antibody for use in treating a neurological disease or disorder is provided (e.g., AD). In certain embodiments, an anti-BACE1 antibody for use in a method of treatment is provided. In certain embodiments, the invention provides an anti-BACE1 antibody for use in a method of treating an individual having a neurological disease or disorder comprising administering to the individual an effective amount of the anti-BACE1 antibody. In one such embodiment, the method further comprises administering to the individual an effective amount of at least one additional therapeutic agent. In further embodiments, the invention provides an anti-BACE1 antibody for use in reducing or inhibiting amlyoid plaque formation in a patient at risk or suffering from a neurological disease or disorder (e.g., AD). In certain embodiments, the invention provides an anti-BACE1 antibody for use in a method of reducing or inhibiting Aβ production in an individual comprising administering to the individual an effective of the anti-BACE1 antibody. An "individual" according to any of the above embodiments is preferably a human. In certain aspect, the anti-BACE antibody for use in the methods of the invention reduces or inhibits BACE1 activity. For example, the anti-BACE1 antibody reduces or inhibits the ability of BACE1 to cleave APP.

In a further aspect, the invention provides for the use of an anti-BACE1 antibody in the manufacture or preparation of a medicament. In some embodiments, the medicament is for treatment of neurological disease or disorder. In a further embodiment, the medicament is for use in a method of treating neurological disease or disorder comprising administering to an individual having neurological disease or disorder an effective amount of the medicament. In one such embodiment, the method further comprises administering to the individual an effective amount of at least one additional therapeutic agent, e.g., as described below. In a further embodiment, the medicament is for inhibiting BACE1 activity. In a further embodiment, the medicament is for use in a method of inhibiting Aβ production or plaque formation in an individual comprising administering to the individual an amount effective of the medicament to inhibit Aβ production or plaque formation. An "individual" according to any of the above embodiments may be a human.

In a further aspect, the invention provides a method for treating Alzheimer's disease. In some embodiments, the method comprises administering to an individual having AD an effective amount of an anti-BACE1 antibody. In one such embodiment, the method further comprises administering to the individual an effective amount of at least one additional therapeutic agent. An "individual" according to any of the above embodiments may be a human.

In a further aspect, the invention provides pharmaceutical formulations comprising any of the anti-BACE1 antibodies provided herein, e.g., for use in any of the above therapeutic methods. In some embodiments, a pharmaceutical formulation comprises any of the anti-BACE1 antibodies provided herein and a pharmaceutically acceptable carrier. In another embodiment, a pharmaceutical formulation comprises any of the anti-BACE1 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Certain embodiments of the invention provide for the antibody or fragment thereof to traverse the blood-brain barrier. Certain neurodegenerative diseases are associated with an increase in permeability of the blood-brain barrier, such that the antibody or active fragment thereof can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or fragment thereof across the blood-brain barrier include, but are not limited to, circumventing the blood-brain barrier entirely, or by creating openings in the blood-brain barrier. Circumvention methods include, but are not limited to, direct injection into the brain (see e.g., Papanastassiou et al., Gene Therapy 9: 398-406 (2002)) and implanting a delivery device in the brain (see e.g., Gill et al., Nature Med. 9: 589-595 (2003); and Gliadel Wafers™, Guildford Pharmaceutical). Methods of creating openings in the barrier include, but are not limited to, ultrasound (see e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see e.g., U.S. Pat. Nos. 5,112,596, 5,268,164, 5,506,206, and 5,686,416), and transfection of neurons that straddle the blood-brain barrier with vectors containing genes encoding the antibody or fragment thereof (see e.g., U.S. Patent Publication No. 2003/0083299).

Lipid-based methods of transporting the antibody or fragment thereof across the blood-brain barrier include, but are not limited to, encapsulating the antibody or fragment thereof in liposomes that are coupled to antibody binding fragments that bind to receptors on the vascular endothelium of the blood-brain barrier (see e.g., U.S. Patent Application Publication No. 20020025313), and coating the antibody or active fragment thereof in low-density lipoprotein particles (see e.g., U.S. Patent Application Publication No. 20040204354) or apolipoprotein E (see e.g., U.S. Patent Application Publication No. 20040131692).

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-BACE1 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-BACE1 antibody.

III. EXAMPLES

The following are examples of methods and compositions of the invention. It is understood that various other embodiments may be practiced, given the general description provided above.

Example 1: Generation of Anti-BACE1 Antibodies

Fully-human antibodies specifically binding to BACE1 were generated using a yeast-based human antibody display library, selected against human BACE1 extracellular domain (BACE1-ECD), amino acids 1-457 of SEQ ID NO: 179.

Eight naïve human synthetic yeast libraries each of ~$10^9$ diversity were propagated as described previously (see, e.g.: Xu et al, 2013, *Protein Eng. Des. Sel.*, 26: 663-70; WO2009036379; WO2010105256; WO2012009568). For the first two rounds of selection, a magnetic bead sorting technique utilizing the Miltenyi MACS system was performed, as described (see, e.g., Siegel et al., 2004, *J. Immunol. Methods*, 286: 141-53). Briefly, yeast cells (~$10^{10}$ cells/library) were incubated with 200 nM biotinylated BACE1-ECD for 15 min at room temperature in FACS wash buffer (phosphate-buffered saline (PBS)/0.1% bovine serum albumin (BSA)). After washing once with 50 ml ice-cold wash buffer, the cell pellet was resuspended in 40 mL wash buffer, and Streptavidin MicroBeads (500 μl) were added to the yeast and incubated for 15 min at 4° C. Next, the yeast were pelleted, resuspended in 5 mL wash buffer, and loaded onto a Miltenyi LS column. After the 5 mL was loaded, the column was washed 3 times with 3 ml FACS wash buffer. The column was then removed from the magnetic field, and the yeast were eluted with 5 mL of growth media and then grown overnight. The following rounds of sorting were performed using flow cytometry. Approximately $1 \times 10^8$ yeast were pelleted, washed three times with wash buffer, and incubated with decreasing concentrations of biotinylated BACE1-ECD (100 to 1 nM) under equilibrium conditions at room temperature. Yeast were then washed twice and stained with LC-FITC (diluted 1:100) and either SA-633 (diluted 1:500) or EA-PE (diluted 1:50) secondary reagents for 15 min at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences) and sort gates were determined to select for binders. After the final round of sorting, yeast were plated and individual colonies were picked for characterization.

Optimization of select antibodies was carried out by a performing both light chain and heavy chain diversification, each described below.

Light chain diversification: Heavy chain plasmids were extracted and transformed into a light chain library with a diversity of approximately $1 \times 10^6$. Selections were performed as described above with one round of MACS sorting and two rounds of FACS sorting using biotinylated BACE1-ECD titrations so select for higher affinity.

Heavy chain diversification: The CDRH3 of was recombined into a premade library with CDRH1 and CDRH2 variants of a diversity of $1 \times 10^8$ and selections were performed as described above. Affinity pressures were applied by incubating the antigen antibody yeast complex with parental Fab or unbiotinylated antigen for different amounts of time to select for the highest affinity antibodies. Additional cycles of diversification utliized error prone PCR-based mutagenesis of the heavy chain and the light chain. Selections were performed similar to previous cycles using FACS sorting for all three rounds and with increased times for Fab pressure.

Seventy-eight antibodies were chosen from the selection process for sequencing and further characterization. The heavy chain and light chain HVRs for the seventy-eight antibodies are shown in FIGS. 1 and 2, respectively. The heavy chain and light chain variable region sequences are shown in FIGS. 3 and 4, respectively.

The antibodies were determined to be in two separate epitope bins. The epitope bin for each antibody (either bin "2" or bin "3") is shown in FIGS. 1 to 4.

Example 2: Characterization of Anti-BACE1 Antibodies

The anti-BACE1 antibodies selected in Example 1 were further characterized using the assays described below.

A. Binding Kinetics Using Octet® System

The binding affinities for the 78 anti-BACE1 antibodies selected in Example 1 for human and murine BACE1 ECD were determined using an Octet® System (ForteBio) as follows. Anti-BACE1 antibodies were loaded onto anti-human capture (AHC) sensors (tips) followed by 60 seconds baseline in assay buffer. Tips were then exposed to 200 nM of human BACE1 ECD (produced in CHO cells or purchased from R&D Systems) or murine BACE1 ECD (produced in CHO cells; SEQ ID NO: 231). Tips were transferred to assay buffer for 5 minutes, 30 minutes, or 120 minutes depending on the off-rate, for off-rate measurement. Assay buffer was either PBS+0.1% BSA, pH 7.5; or PBS+ 0.1% BSA, pH 5.0. Kinetics were analyzed using a 1:1 binding model.

The results of that experiment are shown in FIG. 5. Measurements with the "<" designations prior to the $K_D$ reach the lower limit of measurable off-rate for that assay run.

B. Binding Kinetics Using Surface Plasmon Resonance (BIAcore™)

Binding affinities of certain anti-BACE1 IgGs were measured by surface plasmon resonance (SRP) using a BIAcore™-T100 instrument. Anti-BACE1 human IgGs were captured by mouse anti-human Fc antibody (GE Healthcare, cat #BR-1008-39) coated on CM5 biosensor chips to achieve approximately 150 response units (RU). For kinetics measurements, two-fold serial dilutions (125 nM to 0 nM) of human BACE1 (R&D Systems) were injected in HBS-P buffer (0.01 M HEPES pH 7.4, 0.15 M NaCl, 0.05% v/v Surfactant P20, GE Healthcare) at 25° C. with a flow rate of 30 μl/min. Association rates ($k_{on}$) and dissociation rates ($k_{off}$) were calculated using a simple one-to-one Langmuir binding model (BIAcore Evaluation Software version 3.2). The equilibrium dissociation constant ($K_D$) was calculated as the ratio $k_{off}/k_{on}$.

The results of that experiment are shown in FIG. 5.

C. Epitope Binning

Epitope binning of the 78 antibodies was performed using the Octet® System. Briefly, a first antibody is loaded onto multiple AHC tips followed by 60 seconds baseline in assay buffer, pH 7.5. Tips are then exposed to 200 nM human BACE1 for 180 seconds to allow for antigen binding. Tips are transferred to wells containing 50 μg/ml second antibody in assay buffer for 90 seconds. If the second antibody shows clear binding, it is considered to be a non-competitor (i.e., in a different epitope bin from the first antibody). If the second antibody does not show clear binding, it is considered to be a competitor (i.e., in the same epitope bin as the first antibody). The binding determination is made by comparing the second antibody binding to BACE1 in the presence of the first antibody to the first antibody blocking itself. To choose the first antibodies, an assay similar to the assay described above is carried out, and antibodies showing mutually exclusive binding are selected.

The epitope bin for each antibody is shown in FIGS. 1 to 4. The 78 antibodies fell into two epitope bins.

D. In Vitro Inhibition Assays

Additionally, the ability of antibodies to modulate BACE1 proteolytic activity on certain BACE substrates was assessed in vitro using the HTRF assay.

In the first assay, certain anti-BACE1 antibodies were diluted in reaction buffer (50 mM NaAcetate pH 4.4, 0.1% CHAPS) to approximately 0.6 µM. BACE1 ECD was diluted in reaction buffer to 0.3 µM. 3 µL of BACE1 and 3 µL of anti-BACE1 antibody were combined in a well of a 384 well plate and incubated for 30 minutes. 3 µL of FRET short substrate Mca-SEVNLDAEFRK(Dnp)RR-NH$_2$ (Mca: (7-Methoxycoumarin-4-yl)acetyl, Dnp: 2, 4-Dinitrophenyl; R&D Systems) (SEQ ID NO: 184) was added and mixed by pulse spin. Fluorescence of the cleaved substrate was monitored every 10 minutes for 1 hour (excitation 320 nm, emission 405 nm). Each anti-BACE1 antibody was tested in quadruplicate. Modulation of BACE1 activity was calculated as ((free enzyme activity)–(IgG:enxyme activity))/ (free enzyme activity). Positive values represent inhibition and negative values represent activation.

The results of that experiment are shown in FIG. 6. In this short substrate assay, both enzyme inhibition (positive percentages), and enzyme activation (negative values) were observed.

In the second assay, certain anti-BACE1 antibodies were tested in a HTRF assay as follows. Two microliters of 375 nM Bi27 (Biotin-KTEEISEVNLDAE-FRHDSGYEVHHQKL (SEQ ID NO:183), American Peptide Company)), an amyloid precursor protein BACE1 cleavage site peptide bearing a substitution to increase sensitivity to BACE1 cleavage, was combined with 3 µL of 125 nM BACE1 pre-incubated with an anti-BACE antibody in BACE reaction buffer (50 mM sodium acetate pH 4.4 and 0.1% CHAPS) in a 384-well plate (Proxiplate™, Perkin-Elmer). The proteolytic reaction mixture was incubated at ambient temperature for 75 minutes and was quenched by the addition of 5 µL HTRF detection mixture containing 2 nM Streptavidin-D2 and 150 nM of 6E10 anti-amyloid beta antibody (Covance, Emoryville, Calif.) labeled with Europium cryptate in detection buffer (200 mM Tris pH 8.0, 20 mM EDTA, 0.1% BSA, and 0.8M KF). The final reaction mixture was incubated at ambient temperature for 60 minutes and the TR-FRET signal was measured using an EnVision Multilabel Plate Reader™ (Perkin-Elmer) at an excitation wavelength of 320 nm and emission wavelengths of 615 and 665 nm. Reactions lacking BACE1 enzyme and reactions lacking anti-BACE1 antibodies were used as controls. Additionally, reactions using a short FRET peptide (Rh-EVNLDAEFK-quencher (SEQ ID NO: 185), Invitrogen) were also performed identically to the HTRF reactions described above.

A synthetic peptide inhibitor of BACE1, OM99-2 (Cal-Biochem®, Catalog #496000) was used as a control. The resulting fluorogenic products from the control reactions were measured as above, but at an excitation wavelength of 545 nm and an emission wavelength of 585 nm. Obtained data were analyzed using GraphPad Prism 5™ (LaJolla, Calif.).

The results of that experiment are shown in FIG. 7. A "decreasing" data mode indicates inhibition, while an "increasing" data mode indicated activation.

Without intending to be bound by any particular theory, modulation of enzyme activity by allosteric inhibitors may, in some instances, result in either activation or inhibition of activity depending on the substrate. For example, a change in conformation caused by an allosteric inhibitor may cause better binding of one substrate and may interfere with binding of another substrate, resulting in differing, or even opposite, activity modulation.

E. In vivo Activity Assay in Primary Cultures

To determine whether the observed in vitro inhibitory action of the anti-BACE1 antibodies on APP processing was also present in a cellular context, in vivo studies were performed. The ability of the antibodies to inhibit $A\beta_{x-40}$ production in primary cultures of mouse cortical neurons expressing endogenous levels of wild-type human amyloid precursor protein was assessed as follows. Briefly, dissociated cortical neuron cultures were prepared from E16.5 CD1 mice. Neurons were seeded at a density of $2.5 \times 10^4$ cells/well in a 96-well plate and grown for five days in Neurobasal media (Life Technologies) in vitro. 50 µl of fresh media containing anti-BACE antibodies or control IgG1 prepared in an 8-point dilution series was incubated with the neurons for 24 hours at 37° C. Cell supernatants were harvested and assayed for the presence of mouse $A\beta_{x-40}$ using a sandwich ELISA Briefly, rabbit polyclonal antibody specific for the C terminus of $A\beta_{x-40}$ (Millipore, Bedford, Mass.) was coated onto plates, and biotinylated anti-mouse Aβ monoclonal antibody M3.2 (Covance, Dedham, Mass.) was used for detection. The assay had lower limit of quantification values of 1.96 pg/ml in plasma and 39.1 pg/g in brain. $A\beta_{x-40}$ values were normalized for cell viability, as determined using the CellTiter-Glo Luminescent Cell Viability Assay (Promega). Data was plotted using a four-parameter non-linear regression curve-fitting program (Prism, Graphpad).

The results of that experiment are shown in FIG. 8. Percent inhibition refers to the maximum inhibition (as % of control) seen with each antibody; percent inhibition was determined as follows: (baseline $A\beta_{x-40}$–minimal $A\beta_{x-40}$)/ baseline $A\beta_{x-40}$*100 (baseline $A\beta_{x-40}$ is in the absence of any treatment).

A similar experiment was performed with antibody 6266 and YW412.8.31.

The results of that experiment are shown in FIG. 9. Antibody 6266 had an $IC_{50}$ of 1.7 nM and a maximum inhibition of 79%, compared to an $IC_{50}$ of 2.9 nM and a maximum inhibition of 62% exhibited by antibody YW412.8.31 (see PCT Publication No. WO 2012/064836 A1).

F. In Vivo Activity Assay in Mice

The ability of anti-BACE1 antibodies to modulate amyloidogenic processing was also assessed in wild-type mice. A single dose of control IgG antibody or an anti-BACE1 antibody (100 mg/kg) was delivered systemically by intraperitoneal (IP) injection to 8-week old wild-type C57Bl/6J mice (n=6 per group). After 24 hours, brain samples were harvested following PBS perfusion, and forebrain from one hemibrain was homogenized in 5M GuHCL, 50 mM Tris pH 8.0, and further diluted in Casein Blocking Buffer (0.25% casein/0.05% sodium azide, 20 µg/ml aprotinin/5 mM EDTA, pH 8.0/10 µg/ml leupeptin in PBS) for $A\beta_{x-40}$ analysis. The concentrations of total mouse $A\beta_{x-40}$ in brain were determined using a sandwich ELISA. Briefly, rabbit polyclonal antibody specific for the C terminus of $A\beta_{1-40}$ (Millipore, Bedford, Mass.) was coated onto plates, and biotinylated anti-mouse Aβ monoclonal antibody M3.2 (Covance, Dedham, Mass.) was used for detection. The assay had lower limit of quantification values of 1.96 pg/ml in plasma and 39.1 pg/g in brain.

Figure 10:
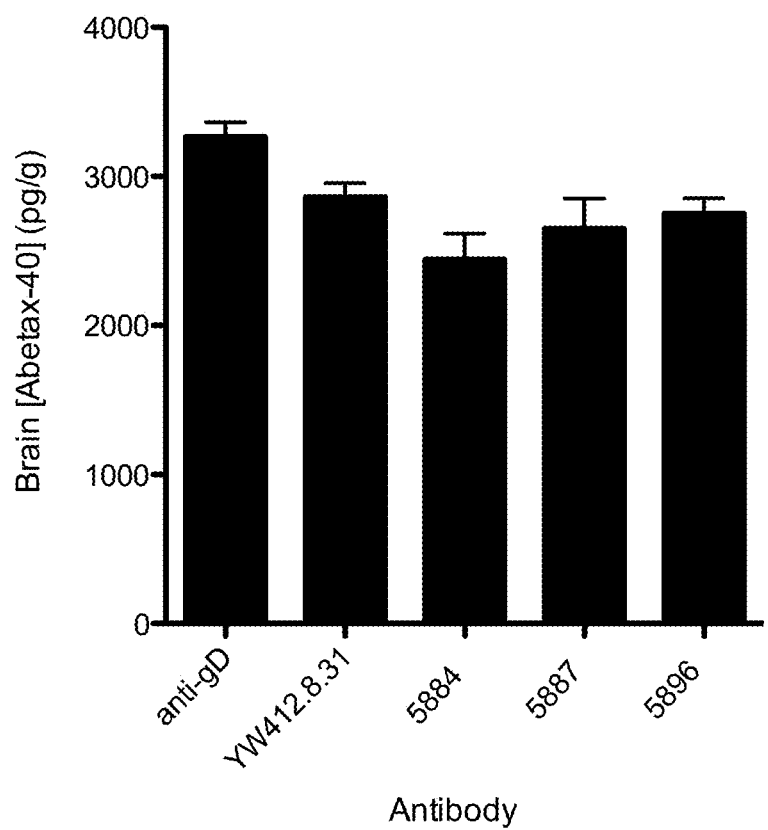
FIG. 10 shows $A\beta_{x-40}$ levels observed in the brain (cortex) of mice treated with 100 mg/kg of the indicated anti-BACE1 antibodies or control IgG antibody.

The results of that experiment are shown in FIG. 10. Administration of antibody 5884 showed the greatest reduction in $A\beta_{x-40}$ levels in mouse brain. Antibody 6226 is derived from antibody 5884, and varies at only two positions in the heavy chain (in HVR-H1).

G. Pharmacokinetics in Cynomolgus Monkeys

The PK profiles of antibody 6266 and antibody 6310 were compared to the PK profile of antibody YW412.8.31 (see PCT Publication No. WO 2012/064836 A1). Antibodies were administered as a single intravenous (IV) dose at 10 mg/kg. Each antibody was administered to four monkeys. Antibody concentration in serum was measured at the following time points: 7 days pre-dose, 15 minutes and 8 hours post-dose, and 1, 3, 7, 10, 14, 17, 21, 28, 35, and 42 days post-dose. The concentrations of the dosed antibodies in cynomolgus monkey serum were measured with an ELISA using a sheep anti-human IgG monkey adsorbed antibody coat, followed by adding serum samples starting at a dilution of 1:100, and finished by adding a goat anti-human IgG antibody conjugated to horseradish peroxidase monkey adsorbed for detection. The assay had a standard curve range of 0.78-50 mg/mL and a limit of detection of 0.08 mg/mL. Results below this limit of detection were reported as less than reportable (LTR).

Figure 11:
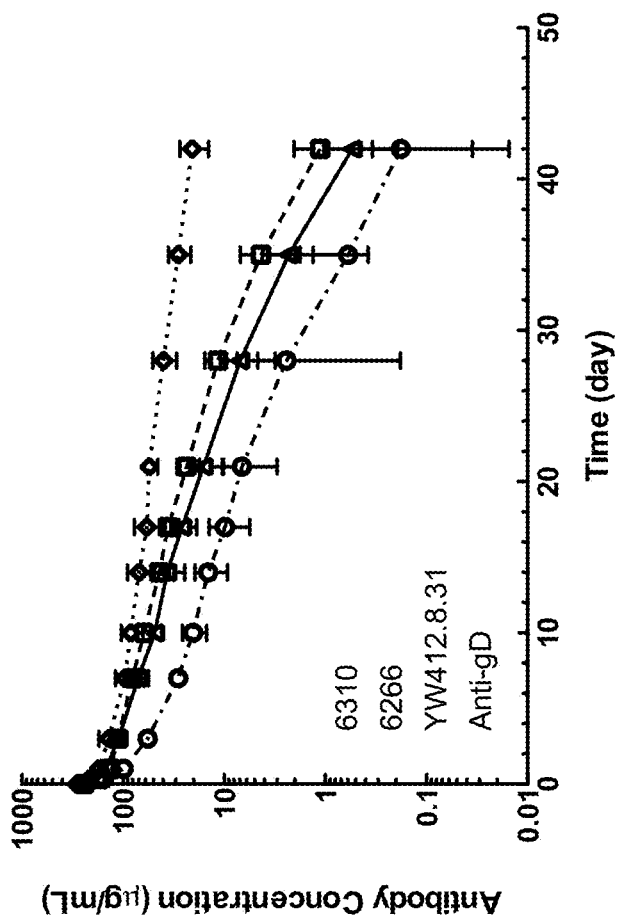
FIG. 11 shows serum antibody concentration over time in cynomolgus monkeys following a single IV dose.

The results of that experiment are shown in FIG. 11. No significant difference was observed in the cynomolgus monkey pharmacokinetics of antibody 6266 compared to YW412.8.31. Antibody 6310 was cleared approximately twice as fast as YW412.8.31.

Example 3: Affinity Maturation of 6266 Antibody

Antibody 6266 was affinity matured as follows.
NNK Walk Library Design and Phage Panning For library randomization, each position of the CDRs was randomized by oligonucleotide-directed mutagenesis with an "NNK" codon, where N is any of the four natural nucleotides, and K is 50% T (thymine) and 50% G (guanine). The NNK codon can encode any of the 20 natural amino acids. Libraries for the light chain and heavy chain were made separately, and each of the 3 CDRs of each chain was randomized at the same time. This results in clones that have 0 to 3 random amino acid changes in each chain, with up to one mutation in each CDR. Libraries were made in a phage Fab fragment display vector by standard methods. Binding clones were selected by incubating the phage display libraries with 5, 0.5, and 0.1 nM biotinylated BACE1 in successive rounds of selection, and then competed with 100 nM non-biotinylated BACE1 at room temperature or 37° C. to reduce binding of the lower affinity clones to BACE1. Bound clones were captured on ELISA plates coated with neutravidin, washed and eluted in 100 mM HCl for 20 minutes at room temperature. The eluted phage was neutralized with 1/10 volume of 1 M Tris pH 8.0 and used to infect E. coli for amplification for the next round of selection.

Deep Sequencing and Data Analysis

For deep sequencing, phagemid DNA was isolated from selected rounds. The VH and the VL segment from each sample were amplified by an 18 cycle PCR amplification using Phusion DNA polymerase (New England Biolabs). The amplicon was purified on a 2% agarose gel. Amplicons were prepared with standard Illumina library prep methods, using TruSeq DNA Sample Prep (Illumina). Adapter-ligated libraries were subjected to a single cycle of PCR and sequenced on the Illumina MiSeq, paired-end 200 bp or 300 bp as appropriate to cover the entire length of the amplicon. Sequencing data where analyzed using the statistical programming language R and the ShortRead package. Quality control was performed on identified CDR sequences, were each CDR sequence was checked for the correct length and was allowed to carry only up to one NNK mutation and no non-NNK mutations. Calculating the frequency of all mutations of every randomized position generated position weight matrices. Enrichment ratios for all single mutations were calculated by dividing the frequency of a given mutation at a given position in the sorted sample by the frequency of the very same mutation in the unsorted sample, as described previously by Fowler and colleagues. The enrichment ratios of double mutations were obtained by calculating the enrichment ratio of all clones that carry NNK mutations at two given positions, ignoring the third NNK mutation. In order to filter out sampling effects, mutation pairs that had less than 10 sequence counts either in the sorted or unsorted sample, were removed from the analysis. Epistasis was calculated by combining the enrichment ratios from single and double mutation in a multiplicative model: EnrichAB=EnrichA×EnrichB. The epistasis used is thus defined as: Epistasis=EnrichAB−EnrichA×EnrichB. The highest enriched mutation from the single mutation analysis and from the double mutation analysis were selected for synthesis.

FIGS. 12 and 13 show the heavy chain and light chain variable region sequences of affinity matured antibody 6266 variants 1 to 15.

Affinity Determination Using Surface Plasmon Resonance

The binding affinity of anti-BACE1 Fab antibodies by single-cycle kinetics was determined using surface plasmon resonance (SRP) measurement with a BIAcore™ T200 instrument. Briefly, series S sensor chip CM5 was activated with EDC and NHS reagents according to the supplier's instructions, and anti-His antibody was coupled to achieve approximately 1000 response units (RU), then following by blocking un-reacted groups with 1M ethanolamine. For kinetics measurements, His-tagged BACE1 protein was first injected at 10 µl/min flow rate to capture approximately 100 RU at 3 different flow cells (FC), except for FC1 (reference), and then 5-fold serial dilutions of Fab in HBS-P buffer (0.01M HEPES pH 7.4, 0.15M NaCl, 0.005% surfactant P20) from low (0.08 nM) to high (50 nM) were injected (flow rate: 30 µl/min) one after the other in the same cycle with no regeneration between injections. The sensorgram was recorded and subject to reference and buffer subtraction before evaluating by BIAcore™ T200 Evaluation Software (version 2.0). Association rates ($k_{on}$) and dissociation rates ($k_{off}$) were calculated using a simple one-to-one Langmuir binding model. The equilibrium dissociation constant (Kd) was calculated as the ratio $k_{off}/k_{on}$.

Thermal Melt Temperature (Tm) Determination by Differential Scanning Fluorimetry (DSF)

DSF monitors thermal unfolding of proteins in the presence of a fluorescent dye and is typically performed by using a real-time PCR instrument (e.g., Bio-Rad CFX). SYPRO orange dye (Invitrogen, cat. no. 56650) is diluted 1:20 in PBS. One μl of diluted dye is added to 24 μl Fab protein (~100 ug/ml) in a well. As the temperature increases from 20° C. to 100° C. in the real-time PCR instrument (Bio-Rad CFX), the fluorescence intensity is plotted and the inflection point of the transition curve (Tm) is calculated using, for example, the Boltzmann equation. See *Nature Protocols*, 2007, 2:2212-2221.

FIG. 14 shows the association rate, dissociation rate, dissociation constant, and melting temperature for the affinity matured antibody 6266 variants 1 to 15. All of the variants showed improved affinity ($K_D$) compared to antibody 6266.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Table of Sequences

| SEQ ID NO | Descripton | Sequence |
|---|---|---|
| 179 | Human BACE1, isoform B | MAQALPWLLL WMGAGVLPAH GTQHGIRLPL RSGLGGAPLG LRLPRETDEE PEEPGRRGSF VEMVDNLRGK SGQGYYVEMT VGSPPQTLNI LVDTGSSNFA VGAAPHPFLH RYYQRQLSST YRDLRKGVYV PYTQGKWEGE LGTDLVSIPH GPNVTVRANI AAITESDKFF INGSNWEGIL GLAYAEIARP DDSLEPFFDS LVKQTHVPNL FSLQLCGAGF PLNQSEVLAS VGGSMIIGGI DHSLYTGSLW YTPIRREWYY EVIIVRVEIN GQDLKMDCKE YNYDKSIVDS GTTNLRLPKK VFEAAVKSIK AASSTEKFPD GFWLGEQLVC WQAGTTPWNI FPVISLYLMG EVTNQSFRIT ILPQQYLRPV EDVATSQDDC YKFAISQSST GTVMGAVIME GFYVVFDRAR KRIGFAVSAC HVHDEFRTAA VEGPFVTLDM EDCGYNIPQT DESTLMTIAY VMAAICALFM LPLCLMVCQW CCLRCLRQQH DDFADDISLL K |
| 180 | Human BACE1, isoform A | MAQALPWLLL WMGAGVLPAH GTQHGIRLPL RSGLGGAPLG LRLPRETDEE PEEPGRRGSF VEMVDNLRGK SGQGYYVEMT VGSPPQTLNI LVDTGSSNFA VGAAPHPFLH RYYQRQLSST YRDLRKGVYV PYTQGKWEGE LGTDLVSIPH GPNVTVRANI AAITESDKFF INGSNWEGIL GLAYAEIARL CGAGFPLNQS EVLASVGGSM IIGGIDHSLY TGSLWYTPIR REWYYEVIIV RVEINGQDLK MDCKEYNYDK SIVDSGTTNL RLPKKVFEAA VKSIKAASST EKFPDGFWLG EQLVCWQAGT TPWNIFPVIS LYLMGEVTNQ SFRITILPQQ YLRPVEDVAT SQDDCYKFAI SQSSTGTVMG AVIMEGFYVV FDRARKRIGF AVSACHVHDE FRTAAVEGPF VTLDMEDCGY NIPQTDESTL MTIAYVMAAI CALFMLPLCL MVCQWCCLRC LRQQHDDFAD DISLLK |
| 181 | Human BACE1, isoform C | MAQALPWLLL WMGAGVLPAH GTQHGIRLPL RSGLGGAPLG LRLPRETDEE PEEPGRRGSF VEMVDNLRGK SGQGYYVEMT VGSPPQTLNI LVDTGSSNFA VGAAPHPFLH RYYQRQLSST YRDLRKGVYV PYTQGKWEGE LGTDLPDDSL EPFFDSLVKQ THVPNLFSLQ LCGAGFPLNQ SEVLASVGGS MIIGGIDHSL YTGSLWYTPI RREWYYEVII VRVEINGQDL KMDCKEYNYD KSIVDSGTTN LRLPKKVFEA AVKSIKAASS TEKFPDGFWL GEQLVCWQAG TTPWNIFPVI SLYLMGEVTN QSFRITILPQ QYLRPVEDVA TSQDDCYKFA ISQSSTGTVM GAVIMEGFYV VFDRARKRIG FAVSACHVHD EFRTAAVEGP FVTLDMEDCG YNIPQTDEST LMTIAYVMAA ICALFMLPLC LMVCQWCCLR CLRQQHDDFA DDISLLK |
| 182 | Human BACE1, isoform D | MAQALPWLLL WMGAGVLPAH GTQHGIRLPL RSGLGGAPLG LRLPRETDEE PEEPGRRGSF VEMVDNLRGK SGQGYYVEMT VGSPPQTLNI LVDTGSSNFA VGAAPHPFLH RYYQRQLSST YRDLRKGVYV PYTQGKWEGE LGTDLLCGAG FPLNQSEVLA SVGGSMIIGG IDHSLYTGSL WYTPIRREWY YEVIIVRVEI NGQDLKMDCK EYNYDKSIVD SGTTNLRLPK KVFEAAVKSI KAASSTEKFP DGFWLGEQLV CWQAGTTPWN IFPVISLYLM GEVTNQSFRI TILPQQYLRP VEDVATSQDD CYKFAISQSS TGTVMGAVIM EGFYVVFDRA RKRIGFAVSA CHVHDEFRTA AVEGPFVTLD MEDCGYNIPQ TDESTLMTIA YVMAAICALF MLPLCLMVCQ WCCLRCLRQQ HDDFADDISL LK |
| 228 | Murine BACE1, isoform 1 | MAPALHWLLL WVGSGMLPAQ GTHLGIRLPL RSGLAGPPLG LRLPRETDEE SEEPGRRGSF VEMVDNLRGK SGQGYYVEMT VGSPPQTLNI LVDTGSSNFA VGAAPHPFLH RYYQRQLSST YRDLRKGVYV PYTQGKWEGE LGTDLVSIPH GPNVTVRANI AAITESDKFF INGSNWEGIL GLAYAEIARP DDSLEPFFDS LVKQTHIPNI FSLQLCGAGF PLNQTEALAS VGGSMIIGGI |

Table of Sequences

| SEQ ID NO | Descripton | Sequence |
|---|---|---|
| | | DHSLYTGSLW YTPIRREWYY EVIIVRVEIN GQDLKMDCKE YNYDKSIVDS GTTNLRLPKK VFEAAVKSIK AASSTEKFPD GFWLGEQLVC WQAGTTPWNI FPVISLYLMG EVTNQSFRIT ILPQQYLRPV EDVATSQDDC YKFAVSQSST GTVMGAVIME GFYVVFDRAR KRIGFAVSAC HVHDEFRTAA VEGPFVTADM EDCGYNIPQT DESTLMTIAY VMAAICALFM LPLCLMVCQW RCLRCLRHQH DDFADDISLL K |
| 229 | Murine BACE1, isoform 2 | MAPALHWLLL WVGSGMLPAQ GTHLGIRLPL RSGLAGPPLG LRLPRETDEE SEEPGRRGSF VEMVDNLRGK SGQGYYVEMT VGSPPQTLNI LVDTGSSNFA VGAAPHPFLH RYYQRQLSST YRDLRKGVYV PYTQGKWEGE LGTDLVSIPH GPNVTVRANI AAITESDKFF INGSNWEGIL GLAYAEIARP DDSLEPFFDS LVKQTHIPNI FSLQLCGAGF PLNQTEALAS VGGSMIIGGI DHSLYTGSLW YTPIRREWYY EVIIVRVEIN GQDLKMDCKE TEKFPDGFWL GEQLVCWQAG TTPWNIFPVI SLYLMGEVTN QSFRITILPQ QYLRPVEDVA TSQDDCYKFA VSQSSTGTVM GAVIMEGFYV VFDRARKRIG FAVSACHVHD EFRTAAVEGP FVTADMEDCG YNIPQTDEST LMTIAYVMAA ICALFMLPLC LMVCQWRCLR CLRHQHDDFA DDISLLK |
| 230 | human BACE1 ECD | MAQALPWLLL WMGAGVLPAH GTQHGIRLPL RSGLGGAPLG LRLPRETDEE PEEPGRRGSF VEMVDNLRGK SGQGYYVEMT VGSPPQTLNI LVDTGSSNFA VGAAPHPFLH RYYQRQLSST YRDLRKGVYV PYTQGKWEGE LGTDLVSIPH GPNVTVRANI AAITESDKFF INGSNWEGIL GLAYAEIAR PDDSLEPFFD SLVKQTHVPN LFSLQLCGAG FPLNQSEVLA SVGGSMIIGG IDHSLYTGSL WYTPIRREWY YEVIIVRVEI NGQDLKMDCK EYNYDKSIVD SGTTNLRLPK KVFEAAVKSI KAASSTEKFP DGFWLGEQLV CWQAGTTPWN IFPVISLYLM GEVTNQSFRI TILPQQYLRP VEDVATSQDD CYKFAISQSS TGTVMGAVIM EGFYVVFDRA RKRIGFAVSA CHVHDEFRTA AVEGPFVTLD MEDCGYNIPQ TDESTLMTGR A |
| 231 | Murine BACE1 ECD | MAPALHWLLL WVGSGMLPAQ GTHLGIRLPL RSGLAGPPLG LRLPRETDEE SEEPGRRGSF VEMVDNLRGK SGQGYYVEMT VGSPPQTLNI LVDTGSSNFA VGAAPHPFLH RYYQRQLSST YRDLRKGVY VPYTQGKWEG ELGTDLVSIP HGPNVTVRAN IAAITESDKF FINGSNWEGI LGLAYAEIAR PDDSLEPFFD SLVKQTHIPN IFSLQLCGAG FPLNQTEALA SVGGSMIIGG IDHSLYTGRL WYTPIRREWY YEVIIVRVEI NGQDLKMDCK EYNYDKSIVD SGTTNLRLPK KVFEAAVKSI KAASSTEKFP DGFWLGEQLV CWQAGTTPWN IFPVISLYLM GEVTNQSFRI TILPQQYLRP VEDVATSQDD CYKFAVSQSS TGTVMGAVIM EGFYVVFDRA RKRIGFAVSA CHVHDEFRTA AVEGPFVTAD MEDCGYNIPQ TDESTLMTGR A |
| 183 | Bi27 peptide | Biotin-KTEEISEVNLDAEFRHDSGYEVHHQKL |
| 184 | FRET short substrate (R&D Systems) | Mca-SEVNLDAEFRK(Dnp)RR-NH$_2$ |
| 185 | FRET short substrate (Invitrogen) | Rh-EVNLDAEFK-quencher |
| 186 | amyloid precursor protein beta secretase active site peptide | FAM-KTEEISEVNLDAEFRWKK-CONH2 |
| 217 | VL HVR2 of 6266.3, 6266.6, 6266.7, 6266.8, 6266.11 | GASTRAY |
| 218 | VH HVR1 of 6266.1, 6266.2, 6266.3, 6266.4, 6266.5, 6266.6, 6266.7 | GTLSHYGVS |
| 219 | VH HVR2 of 6266.1, 6266.2, 6266.3, | NIIPGIGTANYAQKFQG |

-continued

| Table of Sequences | | |
|---|---|---|
| SEQ ID NO | Descripton | Sequence |
| | 6266.4, 6266.5, 6266.6, 6266.7 | |
| 220 | VH HVR3 for 6266.5, 6266.6 | ARSGGTQYGMLDV |
| 221 | VH HVR3 for 6266.7, 6266.15 | ARSGGTKYGELDV |
| 222 | VH HVR1 for 6266.8, 6266.9 | GTLKGYGVS |
| 223 | VH HVR1 for 6266.12 | GTLNGYGVS |
| 224 | VH HVR1 for 6266.13 | GTLSGYGMS |
| 225 | VH HVR2 for 6266.14 | NIIPGFGVANYAQKFQG |
| 226 | VH HVR3 for 6266.8, 6266.9 | ARGGGTKYGMLDV |
| 227 | VH HVR3 for 6266.14 | ARSGGTKWGMLDV |

---

What is claimed is:

1. An isolated nucleic acid encoding an antibody that binds to BACE1, wherein the antibody comprises: an HVR-H1 sequence selected from SEQ ID NOs: 15, 218, and 222 to 224; an HVR-H2 sequence selected from SEQ ID NOs: 29, 219, and 225; an HVR-H3 sequence selected from SEQ ID NOs: 52, 220, 221, 226, and 227; the HVR-L1 sequence of SEQ ID NO: 65; an HVR-L2 sequence selected from SEQ ID NOs: 71, 73, and 217; and the HVR-L3 sequence of SEQ ID NO: 80.

2. The nucleic acid of claim 1, wherein the antibody comprises:
   (a) the HVR-H1 sequence of SEQ ID NO: 15; the HVR-H2 sequence of SEQ ID NO: 29; the HVR-H3 sequence of SEQ ID NO: 52; the HVR-L1 sequence of SEQ ID NO: 65; the HVR-L2 sequence of SEQ ID NO: 71; and the HVR-L3 sequence of SEQ ID NO: 80; or
   (b) the HVR-H1 sequence of SEQ ID NO: 218; the HVR-H2 sequence of SEQ ID NO: 219; the HVR-H3 sequence of SEQ ID NO: 52; the HVR-L1 sequence of SEQ ID NO: 65; the HVR-L2 sequence of SEQ ID NO: 71; and the HVR-L3 sequence of SEQ ID NO: 80; or
   (c) the HVR-H1 sequence of SEQ ID NO: 218; the HVR-H2 sequence of SEQ ID NO: 219; the HVR-H3 sequence of SEQ ID NO: 52; the HVR-L1 sequence of SEQ ID NO: 65; the HVR-L2 sequence of SEQ ID NO: 73; and the HVR-L3 sequence of SEQ ID NO: 80; or
   (d) the HVR-H1 sequence of SEQ ID NO: 218; the HVR-H2 sequence of SEQ ID NO: 219; the HVR-H3 sequence of SEQ ID NO: 52; the HVR-L1 sequence of SEQ ID NO: 65; the HVR-L2 sequence of SEQ ID NO: 217; and the HVR-L3 sequence of SEQ ID NO: 80; or
   (e) the HVR-H1 sequence of SEQ ID NO: 218; the HVR-H2 sequence of SEQ ID NO: 219; the HVR-H3 sequence of SEQ ID NO: 52; the HVR-L1 sequence of SEQ ID NO: 65; the HVR-L2 sequence of SEQ ID NO: 73; and the HVR-L3 sequence of SEQ ID NO: 80; or
   (f) the HVR-H1 sequence of SEQ ID NO: 218; the HVR-H2 sequence of SEQ ID NO: 219; the HVR-H3 sequence of SEQ ID NO: 220; the HVR-L1 sequence of SEQ ID NO: 65; the HVR-L2 sequence of SEQ ID NO: 73; and the HVR-L3 sequence of SEQ ID NO: 80; or
   (g) the HVR-H1 sequence of SEQ ID NO: 218; the HVR-H2 sequence of SEQ ID NO: 219; the HVR-H3 sequence of SEQ ID NO: 220; the HVR-L1 sequence of SEQ ID NO: 65; the HVR-L2 sequence of SEQ ID NO: 217; and the HVR-L3 sequence of SEQ ID NO: 80; or
   (h) the HVR-H1 sequence of SEQ ID NO: 218; the HVR-H2 sequence of SEQ ID NO: 219; the HVR-H3 sequence of SEQ ID NO: 221; the HVR-L1 sequence of SEQ ID NO: 65; the HVR-L2 sequence of SEQ ID NO: 217; and the HVR-L3 sequence of SEQ ID NO: 80; or
   (i) the HVR-H1 sequence of SEQ ID NO: 222; the HVR-H2 sequence of SEQ ID NO: 29; the HVR-H3 sequence of SEQ ID NO: 226; the HVR-L1 sequence of SEQ ID NO: 65; the HVR-L2 sequence of SEQ ID NO: 217; and the HVR-L3 sequence of SEQ ID NO: 80; or
   (j) the HVR-H1 sequence of SEQ ID NO: 222; the HVR-H2 sequence of SEQ ID NO: 29; the HVR-H3 sequence of SEQ ID NO: 226; the HVR-L1 sequence of SEQ ID NO: 65; the HVR-L2 sequence of SEQ ID NO: 73; and the HVR-L3 sequence of SEQ ID NO: 80; or
   (k) the HVR-H1 sequence of SEQ ID NO: 15; the HVR-H2 sequence of SEQ ID NO: 29; the HVR-H3 sequence of SEQ ID NO: 52; the HVR-L1 sequence of SEQ ID NO: 65; the HVR-L2 sequence of SEQ ID NO: 73; and the HVR-L3 sequence of SEQ ID NO: 80; or
   (l) the HVR-H1 sequence of SEQ ID NO: 15; the HVR-H2 sequence of SEQ ID NO: 29; the HVR-H3 sequence of SEQ ID NO: 52; the HVR-L1 sequence of SEQ ID NO: 65; the HVR-L2 sequence of SEQ ID NO: 217; and the HVR-L3 sequence of SEQ ID NO: 80; or
   (m) the HVR-H1 sequence of SEQ ID NO: 223; the HVR-H2 sequence of SEQ ID NO: 29; the HVR-H3 sequence of SEQ ID NO: 52; the HVR-L1 sequence of SEQ ID NO: 65; the HVR-L2 sequence of SEQ ID NO: 71; and the HVR-L3 sequence of SEQ ID NO: 80; or
   (n) the HVR-H1 sequence of SEQ ID NO: 224; the HVR-H2 sequence of SEQ ID NO: 29; the HVR-H3 sequence of SEQ ID NO: 52; the HVR-L1 sequence of SEQ ID NO: 65; the HVR-L2 sequence of SEQ ID NO: 71; and the HVR-L3 sequence of SEQ ID NO: 80; or
   (o) the HVR-H1 sequence of SEQ ID NO: 15; the HVR-H2 sequence of SEQ ID NO: 225; the HVR-H3 sequence of SEQ ID NO: 227; the HVR-L1 sequence of SEQ ID NO: 65; the HVR-L2 sequence of SEQ ID NO: 71; and the HVR-L3 sequence of SEQ ID NO: 80; or
   (p) the HVR-H1 sequence of SEQ ID NO: 15; the HVR-H2 sequence of SEQ ID NO: 29; the HVR-H3 sequence of SEQ ID NO: 221; the HVR-L1 sequence of SEQ ID NO: 65; the HVR-L2 sequence of SEQ ID NO: 71; and the HVR-L3 sequence of SEQ ID NO: 80.

3. The nucleic acid of claim 1, wherein the antibody comprises:
   (a) a heavy chain variable domain sequence selected from SEQ ID NOs: 138, 194 to 200, and 209 to 216; or
   (b) a light chain variable domain sequence selected from SEQ ID NOs: 156, 187 to 193, and 201 to 208; or
   (c) a heavy chain variable domain sequence as in (a) and a light chain variable domain sequence as in (b).

4. The nucleic acid of claim 1, wherein the antibody comprises:
   (a) the heavy chain variable domain sequence of SEQ ID NO: 138; and the light chain variable domain sequence of SEQ ID NO: 156; or
   (b) the heavy chain variable domain sequence of SEQ ID NO: 194; and the light chain variable domain sequence of SEQ ID NO: 187; or (c) the heavy chain variable domain sequence of SEQ ID NO: 195; and the light chain variable domain sequence of SEQ ID NO: 188; or
(d) the heavy chain variable domain sequence of SEQ ID NO: 196; and the light chain variable domain sequence of SEQ ID NO: 189; or
(e) the heavy chain variable domain sequence of SEQ ID NO: 197; and the light chain variable domain sequence of SEQ ID NO: 190; or
(f) the heavy chain variable domain sequence of SEQ ID NO: 198; and the light chain variable domain sequence of SEQ ID NO: 191; or
(g) the heavy chain variable domain sequence of SEQ ID NO: 199; and the light chain variable domain sequence of SEQ ID NO: 192; or
(h) the heavy chain variable domain sequence of SEQ ID NO: 200; and the light chain variable domain sequence of SEQ ID NO: 193; or
(i) the heavy chain variable domain sequence of SEQ ID NO: 209; and the light chain variable domain sequence of SEQ ID NO: 201; or
(j) the heavy chain variable domain sequence of SEQ ID NO: 210; and the light chain variable domain sequence of SEQ ID NO: 202; or
(k) the heavy chain variable domain sequence of SEQ ID NO: 211; and the light chain variable domain sequence of SEQ ID NO: 203; or
(l) the heavy chain variable domain sequence of SEQ ID NO: 212; and the light chain variable domain sequence of SEQ ID NO: 204; or
(m) the heavy chain variable domain sequence of SEQ ID NO: 213; and the light chain variable domain sequence of SEQ ID NO: 205; or
(n) the heavy chain variable domain sequence of SEQ ID NO: 214; and the light chain variable domain sequence of SEQ ID NO: 206; or
(o) the heavy chain variable domain sequence of SEQ ID NO: 215; and the light chain variable domain sequence of SEQ ID NO: 207; or
(p) the heavy chain variable domain sequence of SEQ ID NO: 216; and the light chain variable domain sequence of SEQ ID NO: 208.

5. A host cell comprising the nucleic acid molecule of claim 1.

6. A method of producing an antibody comprising culturing the host cell of claim 5 so that the antibody is produced.

\* \* \* \* \*

SEQUENCE LISTING

<160> NUMBER OF SEQ ID NOS: 232

<210> SEQ ID NO 1
<211> LENGTH: 9
<212> TYPE: PRT
<213> ORGANISM: Artificial Sequence
<220> FEATURE:
<223> OTHER INFORMATION: Synthetic: VH HVR1

<400> SEQUENCE: 1

Phe Thr Phe Ser Ser Tyr Ala Met Ser
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic: VH HVR1

<400> SEQUENCE: 2

Phe Thr Phe Gly Ser Tyr Ala Met Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic: VH HVR1

<400> SEQUENCE: 3

Phe Thr Phe Ser Thr Tyr Ala Met Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic: VH HVR1

<400> SEQUENCE: 4

Phe Thr Phe Ser Ser Arg Ala Met Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic: VH HVR1

<400> SEQUENCE: 5

Phe Thr Phe Gly Ser Tyr Ala Met Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic: VH HVR1

<400> SEQUENCE: 6

Phe Thr Phe Ser Lys Tyr Ala Met Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic: VH HVR1

<400> SEQUENCE: 7

Gly Thr Phe Ser Ser Tyr Ala Ile Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic: VH HVR1

<400> SEQUENCE: 8

Gly Thr Phe Ser Gly Tyr Gly Ile Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic: VH HVR1

<400> SEQUENCE: 9

Gly Thr Phe Arg Gly Tyr Ala Ile Ser
1               5

```
<210> SEQ ID NO 10
<211> LENGTH: 9
<212> TYPE: PRT
<213> ORGANISM: Artificial Sequence
<220> FEATURE:
<223> OTHER INFORMATION: Synthetic: VH HVR1

<400> SEQUENCE: 10

Gly Thr Phe Trp Lys Tyr Ala Ile Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic: VH HVR1

<400> SEQUENCE: 11

Gly Thr Phe Ser Gly Tyr Ala Ile Ser
1               5

<210> SEQ ID NO 12
<211> LENGTH: 11
<212> TYPE: PRT
<213> ORGANISM: Artificial Sequence
<220> FEATURE:
<223> OTHER INFORMATION: Synthetic: VH HVR1

<400> SEQUENCE: 12

Gly Ser Ile Ser Ser Ser Ser Tyr Tyr Trp Gly
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic: VH HVR1

<400> SEQUENCE: 13

Gly Ser Ile Ser Trp Ser Ser Tyr Tyr Trp Ser
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic: VH HVR1

<400> SEQUENCE: 14

Gly Thr Leu Ser Gly Tyr Ala Ile Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic: VH HVR1

<400> SEQUENCE: 15

Gly Thr Leu Ser Gly Tyr Gly Val Ser
1               5

<210> SEQ ID NO 16
```

-continued

```
<211> LENGTH: 9
<212> TYPE: PRT
<213> ORGANISM: Artificial Sequence
<220> FEATURE:
<223> OTHER INFORMATION: Synthetic:  VH HVR1

<400> SEQUENCE: 16

Gly Thr Ile Ser Gly Tyr Gly Ile Ser
1               5

<210> SEQ ID NO 17
<211> LENGTH: 11
<212> TYPE: PRT
<213> ORGANISM: Artificial Sequence
<220> FEATURE:
<223> OTHER INFORMATION: Synthetic:  VH HVR1

<400> SEQUENCE: 17

Gly Pro Ile Ser Ser Ser Ser Tyr Tyr Trp Gly
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic:  VH HVR1

<400> SEQUENCE: 18

Gly Ser Ile Ser Ser Ser Ser His Tyr Trp Gly
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic:  VH HVR1

<400> SEQUENCE: 19

Gly Ser Ile Ser Arg Gly Ser Tyr Tyr Trp Gly
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic:  VH HVR1

<400> SEQUENCE: 20

Gly Ser Thr Ser Ser Ser Ser Tyr Tyr Trp Gly
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Synthetic:  VH HVR1

<400> SEQUENCE: 21

Tyr Thr Phe Thr Gly Tyr Tyr Met His
1               5

<210> SEQ ID NO 22
<211> LENGTH: 17
```

```
<212> TYPE: PRT
<213> ORGANISM: Artificial Sequence
<220> FEATURE:
<223> OTHER INFORMATION: Synthetic: VH HVR2

<400> SEQUENCE: 22

Ala Ile Ser Gly Ser Gly Gly Ser Thr Tyr Tyr Ala Asp Ser Val Lys
1               5                   10                  15

Gly

<210> SEQ ID NO 23
<211> LENGTH: 17
<212> TYPE: PRT
<213> ORGANISM: Artificial Sequence
<220> FEATURE:
<223> OTHER INFORMATION: Synthetic: VH HVR2

<400> SEQUENCE: 23

Ala Thr Ser Gly Ser Gly Gly Ser Thr Tyr Tyr Ala Asp Ser Val Lys
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: Synthetic: VH HVR2

<400> SEQUENCE: 24

Ala Thr Ser Gly Ser Gly Gly Ser Ile Tyr Tyr Ala Asp Ser Val Lys
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: Synthetic: VH HVR2

<400> SEQUENCE: 25

Ala Ile Ser Gly Ser Gly Ile Ser Thr Pro Tyr Ala Asp Ser Val Lys
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: Synthetic: VH HVR2

<400> SEQUENCE: 26

Ser Ile Ile Pro Ile Phe Gly Thr Ala Asn Tyr Ala Gln Lys Phe Gln
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: Synthetic: VH HVR2
```

```
<400> SEQUENCE: 27

Asn Ile Ile Pro Ile Phe Gly Thr Ala Asn Tyr Ala Gln Lys Phe Gln
1               5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: Synthetic: VH HVR2

<400> SEQUENCE: 28

Gly Ile Ile Pro Ile Gly Gly Ala Asn Tyr Ala Gln Lys Phe Gln
1               5                   10                  15

Gly

<210> SEQ ID NO 29
<211> LENGTH: 17
<212> TYPE: PRT
<213> ORGANISM: Artificial Sequence
<220> FEATURE:
<223> OTHER INFORMATION: Synthetic: VH HVR2

<400> SEQUENCE: 29

Asn Ile Ile Pro Gly Phe Gly Thr Ala Asn Tyr Ala Gln Lys Phe Gln
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Synthetic: VH HVR2

<400> SEQUENCE: 30

Asn Ile Ile Pro Gly Phe Gly Thr Ala Asn Tyr Ala Gln Lys Phe Arg
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Synthetic: VH HVR2

<400> SEQUENCE: 31

Asn Ile Ile Pro Ile Phe Gly Pro Ala Asn Tyr Ala Gln Lys Phe Gln
1               5                   10                  15

Gly

<210> SEQ ID NO 32
<211> LENGTH: 16
<212> TYPE: PRT
<213> ORGANISM: Artificial Sequence
<220> FEATURE:
<223> OTHER INFORMATION: Synthetic: VH HVR2
```

```
<400> SEQUENCE: 32

Ser Ile Tyr Tyr Ser Gly Ser Thr Tyr Tyr Asn Pro Ser Leu Lys Ser
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic:  VH HVR2

<400> SEQUENCE: 33

Ser Ile Tyr Arg Ser Gly Ser Thr Tyr Tyr Asn Pro Ser Leu Lys Ser
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Synthetic:  VH HVR2

<400> SEQUENCE: 34

Ser Ile Tyr Lys Ser Gly Arg Thr Tyr Tyr Asn Pro Ser Leu Lys Ser
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic:  VH HVR2

<400> SEQUENCE: 35

Ser Ile Tyr Arg Ser Gly Ser Thr Trp Tyr Asn Pro Ser Leu Lys Ser
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic:  VH HVR2

<400> SEQUENCE: 36

Met Ile Tyr Tyr Ser Gly Ser Thr Trp Tyr Asn Pro Ser Leu Lys Ser
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetic:  VH HVR2

<400> SEQUENCE: 37

Ser Ile Tyr Arg Ser Gly Arg Thr Tyr Tyr Asn Pro Ser Leu Lys Ser
1               5                   10                  15

<210> SEQ ID NO 38
<211> LENGTH: 17
<212> TYPE: PRT
<213> ORGANISM: Artificial Sequence
<220> FEATURE:
<223> OTHER INFORMATION: Synthetic:  VH HVR2
```

```
<400> SEQUENCE: 38

Asn Ile Ile Pro Gly Phe Gly Thr Ala Asn Tyr Ala Gln Lys Ser Gln
1               5                   10                  15

Gly

<210> SEQ ID NO 39
<211> LENGTH: 17
<212> TYPE: PRT
<213> ORGANISM: Artificial Sequence
<220> FEATURE:
<223> OTHER INFORMATION: Synthetic: VH HVR2

<400> SEQUENCE: 39

Asn Ile Ile Pro Gly Leu Ser Thr Ala Asn Tyr Ala Gln Lys Phe Gln
1               5                   10                  15

Gly

<210> SEQ ID NO 40
<211> LENGTH: 16
<212> TYPE: PRT
<213> ORGANISM: Artificial Sequence
<220> FEATURE:
<223> OTHER INFORMATION: Synthetic: VH HVR2

<400> SEQUENCE: 40

Ser Ile Tyr Arg Ser Gly Arg Thr Tyr Tyr Asn Pro Ser Leu Lys Gly
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Synthetic: VH HVR2

<400> SEQUENCE: 41

Met Ile Tyr Tyr Ser Gly Ser Thr Trp Tyr Asn Pro Ser Leu Arg Ser
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic: VH HVR2

<400> SEQUENCE: 42

Ser Ile Tyr Arg Ser Gly Ser Thr Tyr Tyr Asn Pro Ser Phe Lys Ser
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetic: VH HVR2

<400> SEQUENCE: 43

Ser Ile Tyr Arg Ser Gly Ser Thr Tyr Tyr Asn Pro Ser Leu Arg Ser
1               5                   10                  15

<210> SEQ ID NO 44
<211> LENGTH: 16
<212> TYPE: PRT
```

<213> ORGANISM: Artificial Sequence
<220> FEATURE:
<223> OTHER INFORMATION: Synthetic: VH HVR2

<400> SEQUENCE: 44

Asn Ile Tyr Tyr Ser Gly Ser Thr Tyr Tyr Asn Pro Ser Leu Lys Ser
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic: VH HVR2

<400> SEQUENCE: 45

Asn Ile Tyr Tyr Ser Gly Ser Thr Tyr Tyr Asn Pro Ser Leu Arg Ser
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Synthetic: VH HVR2

<400> SEQUENCE: 46

Asn Ile Tyr Tyr Ser Gly Ser Thr Tyr Tyr Asn Pro Ser Leu Lys Gly
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic: VH HVR2

<400> SEQUENCE: 47

Gln Ile Tyr Tyr Ser Gly Ser Thr Phe Tyr Asn Pro Ser Leu Lys Ser
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic: VH HVR2

<400> SEQUENCE: 48

Asn Ile Tyr Tyr Ser Gly Ser Thr Tyr Tyr Asn Pro Ser Leu Arg Gly
1               5                   10                  15

<210> SEQ ID NO 49
<211> LENGTH: 17
<212> TYPE: PRT
<213> ORGANISM: Artificial Sequence
<220> FEATURE:
<223> OTHER INFORMATION: Synthetic: VH HVR2

<400> SEQUENCE: 49

Ser Ile Asn Pro Asn Ser Gly Gly Thr Asn Tyr Ala Gln Lys Phe Gln
1               5                   10                  15

Gly

<210> SEQ ID NO 50
<211> LENGTH: 17

```
<212> TYPE: PRT
<213> ORGANISM: Artificial Sequence
<220> FEATURE:
<223> OTHER INFORMATION: Synthetic: VH HVR3

<400> SEQUENCE: 50

Ala Lys Gly Gly Ser Gln Trp Leu Tyr Ala Pro Gly Ser Trp Phe Asp
1               5                   10                  15

Pro

<210> SEQ ID NO 51
<211> LENGTH: 16
<212> TYPE: PRT
<213> ORGANISM: Artificial Sequence
<220> FEATURE:
<223> OTHER INFORMATION: Synthetic: VH HVR3

<400> SEQUENCE: 51

Ala Lys Gly Ala Gly His Gly Ser Tyr Val Lys Gly Trp Phe Asp Pro
1               5                   10                  15

<210> SEQ ID NO 52
<211> LENGTH: 13
<212> TYPE: PRT
<213> ORGANISM: Artificial Sequence
<220> FEATURE:
<223> OTHER INFORMATION: Synthetic: VH HVR3

<400> SEQUENCE: 52

Ala Arg Ser Gly Gly Thr Lys Tyr Gly Met Leu Asp Val
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic: VH HVR3

<400> SEQUENCE: 53

Ala Arg Val Gly His Gly Ile Ser Tyr Phe Asp Leu
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic: VH HVR3

<400> SEQUENCE: 54

Ala Arg Ser Gly Gly Thr Arg Tyr Gly Met Leu Asp Val
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic: VH HVR3

<400> SEQUENCE: 55

Ala Arg Val Gly His Gly Ile Asn Tyr Phe Asp Leu
1               5                   10

<210> SEQ ID NO 56
```

```
<211> LENGTH: 12
<212> TYPE: PRT
<213> ORGANISM: Artificial Sequence
<220> FEATURE:
<223> OTHER INFORMATION: Synthetic: VH HVR3

<400> SEQUENCE: 56

Ala Arg Val Gly Leu Gly Val Ser Tyr Phe Asp Leu
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic: VH HVR3

<400> SEQUENCE: 57

Ala Arg Val Gly His Gly Val Ser Tyr Phe Asp Leu
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic: VH HVR3

<400> SEQUENCE: 58

Val Arg Val Gly His Gly Ile Ser Tyr Phe Asp Leu
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic: VH HVR3

<400> SEQUENCE: 59

Ala Arg Leu Gly His Gly Tyr Ser Tyr Phe Asp Leu
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic: VH HVR3

<400> SEQUENCE: 60

Ala Arg Leu Gly His Gly Tyr Asn Tyr Phe Asp Leu
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic: VH HVR3

<400> SEQUENCE: 61

Ala Arg Val Arg Val Arg His Tyr Gly Met Asp Val
1               5                   10

<210> SEQ ID NO 62
<211> LENGTH: 11
```

```
<212> TYPE: PRT
<213> ORGANISM: Artificial Sequence
<220> FEATURE:
<223> OTHER INFORMATION: Synthetic: VL HVR1

<400> SEQUENCE: 62

Arg Ala Ser Gln Ser Ile Ser Ser Tyr Leu Asn
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic: VL HVR1

<400> SEQUENCE: 63

Arg Ala Ser Gln Ser Val Ser Ser Tyr Leu Ala
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic: VL HVR1

<400> SEQUENCE: 64

Arg Ala Ser Gln Ser Val Gly Ser Asn Leu Ala
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic: VL HVR1

<400> SEQUENCE: 65

Arg Ala Ser Gln Ser Val Ser Ser Asn Leu Ala
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Synthetic: VL HVR1

<400> SEQUENCE: 66

Arg Ala Ser Gln Ser Val Ser Ser Asn Ile Ala
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic: VL HVR1

<400> SEQUENCE: 67

Arg Ala Ser Gln Ser Val Ser Ser His Leu Ala
1               5                   10

<210> SEQ ID NO 68
<211> LENGTH: 11
<212> TYPE: PRT
```

```
<213> ORGANISM: Artificial Sequence
<220> FEATURE:
<223> OTHER INFORMATION: Synthetic: VL HVR1

<400> SEQUENCE: 68

Arg Ala Ser Arg Ser Val Asn Ser Tyr Leu Ala
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic: VL HVR2

<400> SEQUENCE: 69

Ala Ala Ser Ser Leu Gln Ser
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic: VL HVR2

<400> SEQUENCE: 70

Asp Ala Ser Asn Arg Ala Thr
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic: VL HVR2

<400> SEQUENCE: 71

Gly Ala Ser Thr Arg Ala Thr
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic: VL HVR2

<400> SEQUENCE: 72

Asp Ala Ser Lys Arg Ala Thr
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic: VL HVR2

<400> SEQUENCE: 73

Gly Ala Ser Lys Arg Ala Thr
1               5

<210> SEQ ID NO 74
<211> LENGTH: 7
<212> TYPE: PRT
<213> ORGANISM: Artificial Sequence
```

<220> FEATURE:
<223> OTHER INFORMATION: Synthetic: VL HVR2

<400> SEQUENCE: 74

Asp Ala Ser Ser Arg Ala Thr
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic: VL HVR3

<400> SEQUENCE: 75

Gln Gln Ser Tyr Ser Val Pro Leu Thr
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic: VL HVR3

<400> SEQUENCE: 76

Val Gln Arg Ser Asn Phe Pro Trp Thr
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic: VL HVR3

<400> SEQUENCE: 77

Gln Gln Ser Ser Asn Phe Pro Phe Thr
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic: VL HVR3

<400> SEQUENCE: 78

Gln Gln Ser Val Asn Phe Pro Phe Thr
1               5

<210> SEQ ID NO 79
<211> LENGTH: 10
<212> TYPE: PRT
<213> ORGANISM: Artificial Sequence
<220> FEATURE:
<223> OTHER INFORMATION: Synthetic: VL HVR3

<400> SEQUENCE: 79

Gln Gln Ala Val Val Trp Pro Pro Arg Thr
1               5                   10

<210> SEQ ID NO 80
<211> LENGTH: 10
<212> TYPE: PRT
<213> ORGANISM: Artificial Sequence
<220> FEATURE:

<223> OTHER INFORMATION: Synthetic: VL HVR3

<400> SEQUENCE: 80

Gln Gln Leu Ile Leu Trp Pro Pro Arg Thr
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthetic: VL HVR3

<400> SEQUENCE: 81

Gln Gln Leu Tyr Thr Trp Pro Pro Arg Thr
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic: VL HVR3

<400> SEQUENCE: 82

Gln Gln Ala Tyr Val Trp Pro Pro Arg Thr
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic: VL HVR3

<400> SEQUENCE: 83

Gln Gln Ser Leu Thr Trp Pro Pro Arg Thr
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic: VL HVR3

<400> SEQUENCE: 84

Gln Gln Val Tyr Thr Trp Pro Pro Arg Thr
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic: VL HVR3

<400> SEQUENCE: 85

Gln Gln Leu Phe Leu Trp Pro Pro Arg Thr
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic: VL HVR3

```
<400> SEQUENCE: 86

Gln Gln Ser Tyr Leu Trp Pro Pro Arg Thr
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Synthetic:  VL HVR3

<400> SEQUENCE: 87

Gln Gln Ser Phe Leu Trp Pro Pro Arg Thr
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic:  VL HVR3

<400> SEQUENCE: 88

Gln Gln Leu Leu Thr Trp Pro Pro Arg Thr
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Synthetic:  VL HVR3

<400> SEQUENCE: 89

Gln Gln Ser Phe Val Trp Pro Pro Arg Thr
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic:  VL HVR3

<400> SEQUENCE: 90

Gln Gln Leu Leu Leu Trp Pro Pro Arg Thr
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthetic:  VL HVR3

<400> SEQUENCE: 91

Gln Gln Ser Ile Val Trp Pro Pro Arg Thr
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic:  VL HVR3
```

```
<400> SEQUENCE: 92

Gln Gln Ser Leu Val Trp Pro Pro Arg Thr
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic:  VL HVR3

<400> SEQUENCE: 93

Gln Gln Ser Ile Thr Trp Pro Pro Arg Thr
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic:  VL HVR3

<400> SEQUENCE: 94

Gln Gln Ser Val Thr Trp Pro Pro Arg Thr
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Synthetic:  VL HVR3

<400> SEQUENCE: 95

Gln Gln Val Tyr Leu Trp Pro Pro Arg Thr
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Synthetic:  VL HVR3

<400> SEQUENCE: 96

Gln Gln Val Tyr Val Trp Pro Pro Arg Thr
1               5                   10

<210> SEQ ID NO 97
<211> LENGTH: 9
<212> TYPE: PRT
<213> ORGANISM: Artificial Sequence
<220> FEATURE:
<223> OTHER INFORMATION: Synthetic:  VL HVR3

<400> SEQUENCE: 97

Gln Gln Pro Leu Ser His Pro Arg Thr
1               5

<210> SEQ ID NO 98
<211> LENGTH: 10
<212> TYPE: PRT
<213> ORGANISM: Artificial Sequence
<220> FEATURE:
<223> OTHER INFORMATION: Synthetic:  VL HVR3
```

<400> SEQUENCE: 98

Asp Glu Ser Tyr Ser Thr Pro Pro Trp Thr
1               5                   10

<210> SEQ ID NO 99
<211> LENGTH: 124
<212> TYPE: PRT
<213> ORGANISM: Artificial Sequence
<220> FEATURE:
<223> OTHER INFORMATION: Synthetic:  VH sequence

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Ser Gln Trp Leu Tyr Ala Pro Gly Ser Trp Phe Asp
            100                 105                 110

Pro Trp Gly Gln Gly Thr Leu Val Thr Val Ser Ser
        115                 120

<210> SEQ ID NO 100
<211> LENGTH: 123
<212> TYPE: PRT
<213> ORGANISM: Artificial Sequence
<220> FEATURE:
<223> OTHER INFORMATION: Synthetic:  VH sequence

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Gly His Gly Ser Tyr Val Lys Gly Trp Phe Asp Pro
            100                 105                 110

Trp Gly Gln Gly Thr Leu Val Thr Val Ser Ser
        115                 120

<210> SEQ ID NO 101
<211> LENGTH: 123
<212> TYPE: PRT
<213> ORGANISM: Artificial Sequence

```
<220> FEATURE:
<223> OTHER INFORMATION: Synthetic: VH sequence

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ile Ser Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Gly His Gly Ser Tyr Val Lys Gly Trp Phe Asp Pro
            100                 105                 110

Trp Gly Gln Gly Thr Leu Val Thr Val Ser Ser
        115                 120

<210> SEQ ID NO 102
<211> LENGTH: 124
<212> TYPE: PRT
<213> ORGANISM: Artificial Sequence
<220> FEATURE:
<223> OTHER INFORMATION: Synthetic: VH sequence

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Ser Trp Val Arg Gln Ala Pro Gly Lys Gly Leu Glu Trp Val
        35                  40                  45

Ser Ala Thr Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Lys Gly Gly Ser Gln Trp Leu Tyr Ala Pro Gly Ser Trp Phe Asp
            100                 105                 110

Pro Trp Gly Gln Gly Thr Leu Val Thr Val Ser Ser
        115                 120

<210> SEQ ID NO 103
<211> LENGTH: 124
<212> TYPE: PRT
<213> ORGANISM: Artificial Sequence
<220> FEATURE:
<223> OTHER INFORMATION: Synthetic: VH sequence

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

Ala Met Gly Trp Val Arg Gln Ala Pro Gly Lys Gly Leu Glu Trp Val
            35                  40                  45

Ser Ala Thr Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Ser Gln Trp Leu Tyr Ala Pro Gly Ser Trp Phe Asp
            100                 105                 110

Pro Trp Gly Gln Gly Thr Leu Val Thr Val Ser Ser
            115                 120

<210> SEQ ID NO 104
<211> LENGTH: 124
<212> TYPE: PRT
<213> ORGANISM: Artificial Sequence
<220> FEATURE:
<223> OTHER INFORMATION: Synthetic: VH sequence

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Arg
            20                  25                  30

Ala Met Gly Trp Val Arg Gln Ala Pro Gly Lys Gly Leu Glu Trp Val
            35                  40                  45

Ser Ala Thr Ser Gly Ser Gly Gly Ser Ile Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Ser Gln Trp Leu Tyr Ala Pro Gly Ser Trp Phe Asp
            100                 105                 110

Pro Trp Gly Gln Gly Thr Leu Val Thr Val Ser Ser
            115                 120

<210> SEQ ID NO 105
<211> LENGTH: 123
<212> TYPE: PRT
<213> ORGANISM: Artificial Sequence
<220> FEATURE:
<223> OTHER INFORMATION: Synthetic: VH sequence

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
            35                  40                  45

Ser Ala Ile Ser Gly Ser Gly Ile Ser Thr Pro Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Gly His Gly Ser Tyr Val Lys Gly Trp Phe Asp Pro
            100                 105                 110

Trp Gly Gln Gly Thr Leu Val Thr Val Ser Ser
            115                 120

<210> SEQ ID NO 106
<211> LENGTH: 123
<212> TYPE: PRT
<213> ORGANISM: Artificial Sequence
<220> FEATURE:
<223> OTHER INFORMATION: Synthetic: VH sequence

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ile Ser Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Gly His Gly Ser Tyr Val Lys Gly Trp Phe Asp Pro
            100                 105                 110

Trp Gly Gln Gly Thr Leu Val Thr Val Ser Ser
            115                 120

<210> SEQ ID NO 107
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 107

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
            115                 120

<210> SEQ ID NO 108
<211> LENGTH: 120
<212> TYPE: PRT

<213> ORGANISM: Artificial Sequence
<220> FEATURE:
<223> OTHER INFORMATION: Synthetic: VH sequence

<400> SEQUENCE: 108

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Asn Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Val Val Thr Val Ser Ser
        115                 120

<210> SEQ ID NO 109
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 109

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Gly Gly Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
        115                 120

<210> SEQ ID NO 110
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 110

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Asn Ile Ile Pro Gly Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
                100                 105                 110

Gly Thr Met Val Thr Val Ser Ser
            115                 120

<210> SEQ ID NO 111
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 111

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Asn Ile Ile Pro Ile Phe Gly Pro Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
                100                 105                 110

Gly Thr Met Val Thr Val Ser Ser
            115                 120

<210> SEQ ID NO 112
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 112

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Asn Ile Ile Pro Ile Phe Gly Thr Ala Tyr Ala Gln Lys Phe
        50                  55                  60

Gln Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
        115                 120

<210> SEQ ID NO 113
<211> LENGTH: 120
<212> TYPE: PRT
<213> ORGANISM: Artificial Sequence
<220> FEATURE:
<223> OTHER INFORMATION: Synthetic:  VH sequence

<400> SEQUENCE: 113

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gly Tyr
            20                  25                  30

Gly Ile Ser Trp Val Arg Gln Ala Pro Gly Gln Gly Leu Glu Trp Met
        35                  40                  45

Gly Asn Ile Ile Pro Gly Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
        115                 120

<210> SEQ ID NO 114
<211> LENGTH: 120
<212> TYPE: PRT
<213> ORGANISM: Artificial Sequence
<220> FEATURE:
<223> OTHER INFORMATION: Synthetic:  VH sequence

<400> SEQUENCE: 114

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Gly Tyr
            20                  25                  30

Ala Ile Ser Trp Val Arg Gln Ala Pro Gly Gln Gly Leu Glu Trp Met
        35                  40                  45

Gly Asn Ile Ile Pro Gly Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
        115                 120
```

```
<210> SEQ ID NO 115
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 115

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Gly Tyr
            20                  25                  30

Ala Ile Ser Trp Val Arg Gln Ala Pro Gly Gln Gly Leu Glu Trp Met
        35                  40                  45

Gly Asn Ile Ile Pro Gly Leu Ser Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
        115                 120

<210> SEQ ID NO 116
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 116

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Trp Lys Tyr
            20                  25                  30

Ala Ile Ser Trp Val Arg Gln Ala Pro Gly Gln Gly Leu Glu Trp Met
        35                  40                  45

Gly Asn Ile Ile Pro Gly Phe Gly Thr Ala Asn Tyr Ala Gln Lys Phe
    50                  55                  60

Arg Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
        115                 120

<210> SEQ ID NO 117
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 117

Gln Val Gln Leu Val Gln Ser Gly Ala Glu Val Lys Lys Pro Gly Ser
1               5                   10                  15
```

Ser Val Lys Val Ser Cys Lys Ala Ser Gly Gly Thr Phe Ser Gly Tyr
            20                  25                  30

Ala Ile Ser Trp Val Arg Gln Ala Pro Gly Gln Gly Leu Glu Trp Met
            35                  40                  45

Gly Asn Ile Ile Pro Gly Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
            115                 120

<210> SEQ ID NO 118
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 118

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Gly His Gly Ile Ser Tyr Phe Asp Leu Trp Gly Arg
            100                 105                 110

Gly Thr Leu Val Thr Val Ser Ser
            115                 120

<210> SEQ ID NO 119
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 119

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Ser Ile Tyr Arg Ser Gly Ser Thr Tyr Tyr Asn Pro Ser
        50                  55                  60

```
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Val Gly His Gly Ile Ser Tyr Phe Asp Leu Trp Gly Arg
            100                 105                 110

Gly Thr Leu Val Thr Val Ser Ser
        115                 120

<210> SEQ ID NO 120
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 120

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Arg Ser Gly Ser Thr Trp Tyr Asn Pro Ser
    50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Val Gly His Gly Ile Ser Tyr Phe Asp Leu Trp Gly Arg
            100                 105                 110

Gly Thr Leu Val Thr Val Ser Ser
        115                 120

<210> SEQ ID NO 121
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 121

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Met Ile Tyr Tyr Ser Gly Ser Thr Trp Tyr Asn Pro Ser
    50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95
```

```
Cys Ala Arg Val Gly His Gly Ile Ser Tyr Phe Asp Leu Trp Gly Arg
            100                 105                 110

Gly Thr Leu Val Thr Val Ser Ser
        115                 120

<210> SEQ ID NO 122
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 122

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Met Ile Tyr Tyr Ser Gly Ser Thr Trp Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Gly Leu Gly Val Ser Tyr Phe Asp Leu Trp Gly Arg
            100                 105                 110

Gly Thr Leu Val Thr Val Ser Ser
        115                 120

<210> SEQ ID NO 123
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 123

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Met Ile Tyr Tyr Ser Gly Ser Thr Trp Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Gly His Gly Val Ser Tyr Phe Asp Leu Trp Gly Arg
            100                 105                 110

Gly Thr Leu Val Thr Val Ser Ser
        115                 120

<210> SEQ ID NO 124
<211> LENGTH: 120
<212> TYPE: PRT
```

<213> ORGANISM: Artificial Sequence
<220> FEATURE:
<223> OTHER INFORMATION: Synthetic: VH sequence

<400> SEQUENCE: 124

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Met Ile Tyr Tyr Ser Gly Ser Thr Trp Tyr Asn Pro Ser
50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Val Gly His Gly Val Ser Tyr Phe Asp Leu Trp Gly Arg
        100                 105                 110

Gly Thr Leu Val Thr Val Ser Ser
        115                 120
```

<210> SEQ ID NO 125
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 125

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Arg Ser Gly Ser Thr Tyr Tyr Asn Pro Ser
50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Val Arg Val Gly His Gly Ile Ser Tyr Phe Asp Leu Trp Gly Arg
        100                 105                 110

Gly Thr Leu Val Thr Val Ser Ser
        115                 120
```

<210> SEQ ID NO 126
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 126

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30
```

Ser Tyr Tyr Trp Gly Trp Ile Arg Gln Pro Pro Gly Lys Gly Leu Glu
            35                  40                  45

Trp Ile Gly Asn Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Gly His Gly Tyr Ser Tyr Phe Asp Leu Trp Gly Arg
            100                 105                 110

Gly Thr Leu Val Thr Val Ser Ser
            115                 120

<210> SEQ ID NO 127
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 127

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Asn Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Gly His Gly Tyr Asn Tyr Phe Asp Leu Trp Gly Arg
            100                 105                 110

Gly Thr Leu Val Thr Val Ser Ser
            115                 120

<210> SEQ ID NO 128
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 128

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Asn Ile Tyr Tyr Ser Gly Ser Thr Tyr Tyr Asn Pro Ser
 50                  55                  60

Leu Arg Ser Arg Val Thr Ile Ser Val Asp Thr Ser Lys Asn Gln Phe
65                  70                  75                  80

```
Phe Leu Lys Leu Ser Ser Val Thr Ala Ala Asp Thr Ala Val Tyr Tyr
                85                  90                  95

Cys Ala Arg Leu Gly His Gly Tyr Asn Tyr Phe Asp Leu Trp Gly Arg
            100                 105                 110

Gly Thr Leu Val Thr Val Ser Ser
        115                 120

<210> SEQ ID NO 129
<211> LENGTH: 120
<212> TYPE: PRT
<213> ORGANISM: Artificial Sequence
<220> FEATURE:
<223> OTHER INFORMATION: Synthetic:  VH sequence

<400> SEQUENCE: 129

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Gly His Gly Tyr Asn Tyr Phe Asp Leu Trp Gly Arg
            100                 105                 110

Gly Thr Leu Val Thr Val Ser Ser
        115                 120

<210> SEQ ID NO 130
<211> LENGTH: 120
<212> TYPE: PRT
<213> ORGANISM: Artificial Sequence
<220> FEATURE:
<223> OTHER INFORMATION: Synthetic:  VH sequence

<400> SEQUENCE: 130

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Gln Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Gly His Gly Tyr Ser Tyr Phe Asp Leu Trp Gly Arg
            100                 105                 110

Gly Thr Leu Val Thr Val Ser Ser
        115                 120
```

```
<210> SEQ ID NO 131
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 131
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Arg Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Gly His Gly Tyr Asn Tyr Phe Asp Leu Trp Gly Arg
            100                 105                 110

Gly Thr Leu Val Thr Val Ser Ser
        115                 120

```
<210> SEQ ID NO 132
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 132
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Trp Ser
            20                  25                  30

Ser Tyr Tyr Trp Ser Trp Ile Arg Gln Pro Pro Gly Lys Gly Leu Glu
        35                  40                  45

Trp Ile Gly Ser Ile Tyr Lys Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Gly His Gly Ile Ser Tyr Phe Asp Leu Trp Gly Arg
            100                 105                 110

Gly Thr Leu Val Thr Val Ser Ser
        115                 120

```
<210> SEQ ID NO 133
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 133
```

Gln Leu Gln Leu Gln Glu Ser Gly Pro Gly Leu Val Lys Pro Ser Glu
1               5                   10                  15

```
Thr Leu Ser Leu Thr Cys Thr Val Ser Gly Gly Ser Ile Ser Trp Ser
            20                  25                  30

Ser Tyr Tyr Trp Ser Trp Ile Arg Gln Pro Pro Gly Lys Gly Leu Glu
         35                  40                  45

Trp Ile Gly Ser Ile Tyr Arg Ser Gly Arg Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
            85                  90                  95

Cys Ala Arg Val Gly His Gly Ile Ser Tyr Phe Asp Leu Trp Gly Arg
            100                 105                 110

Gly Thr Leu Val Thr Val Ser Ser
        115                 120

<210> SEQ ID NO 134
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 134

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Trp Ser
            20                  25                  30

Ser Tyr Tyr Trp Ser Trp Ile Arg Gln Pro Pro Gly Lys Gly Leu Glu
         35                  40                  45

Trp Ile Gly Ser Ile Tyr Arg Ser Gly Arg Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
            85                  90                  95

Cys Ala Arg Val Gly His Gly Ile Asn Tyr Phe Asp Leu Trp Gly Arg
            100                 105                 110

Gly Thr Leu Val Thr Val Ser Ser
        115                 120

<210> SEQ ID NO 135
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 135

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Trp Ser
            20                  25                  30

Ser Tyr Tyr Trp Ser Trp Ile Arg Gln Pro Pro Gly Lys Gly Leu Glu
         35                  40                  45

Trp Ile Gly Ser Ile Tyr Arg Ser Gly Arg Thr Tyr Tyr Asn Pro Ser
 50                  55                  60
```

```
Leu Lys Gly Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Val Gly His Gly Ile Asn Tyr Phe Asp Leu Trp Gly Arg
            100                 105                 110

Gly Thr Leu Val Thr Val Ser Ser
        115                 120

<210> SEQ ID NO 136
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 136

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Trp Ser
            20                  25                  30

Ser Tyr Tyr Trp Ser Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Leu Gly His Gly Tyr Asn Tyr Phe Asp Leu Trp Gly Arg
            100                 105                 110

Gly Thr Leu Val Thr Val Ser Ser
        115                 120

<210> SEQ ID NO 137
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 137

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Gly Tyr
            20                  25                  30

Ala Ile Ser Trp Val Arg Gln Ala Pro Gly Gln Gly Leu Glu Trp Met
        35                  40                  45

Gly Asn Ile Ile Pro Gly Phe Gly Thr Ala Asn Tyr Ala Gln Lys Ser
    50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

```
Ala Arg Ser Gly Gly Thr Arg Tyr Gly Met Leu Asp Val Trp Gly Gln
            100                 105                 110

Gly Thr Met Val Thr Val Ser Ser
        115                 120

<210> SEQ ID NO 138
<211> LENGTH: 120
<212> TYPE: PRT
<213> ORGANISM: Artificial Sequence
<220> FEATURE:
<223> OTHER INFORMATION: Synthetic:  VH sequence

<400> SEQUENCE: 138

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Gly Tyr
            20                  25                  30

Gly Val Ser Trp Val Arg Gln Ala Pro Gly Gln Gly Leu Glu Trp Met
        35                  40                  45

Gly Asn Ile Ile Pro Gly Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
        115                 120

<210> SEQ ID NO 139
<211> LENGTH: 120
<212> TYPE: PRT
<213> ORGANISM: Artificial Sequence
<220> FEATURE:
<223> OTHER INFORMATION: Synthetic:  VH sequence

<400> SEQUENCE: 139

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ile Ser Gly Tyr
            20                  25                  30

Gly Ile Ser Trp Val Arg Gln Ala Pro Gly Gln Gly Leu Glu Trp Met
        35                  40                  45

Gly Asn Ile Ile Pro Gly Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
        115                 120

<210> SEQ ID NO 140
<211> LENGTH: 120
<212> TYPE: PRT
```

<213> ORGANISM: Artificial Sequence
<220> FEATURE:
<223> OTHER INFORMATION: Synthetic: VH sequence

<400> SEQUENCE: 140

| Gln | Leu | Gln | Leu | Gln | Glu | Ser | Gly | Pro | Gly | Leu | Val | Lys | Pro | Ser | Glu |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Thr | Val | Ser | Gly | Gly | Pro | Ile | Ser | Ser | Ser |
|---|---|---|---|---|---|---|---|---|---|---|---|---|---|---|---|
| | | | 20 | | | | | 25 | | | | | 30 | | |

| Ser | Tyr | Tyr | Trp | Gly | Trp | Ile | Arg | Gln | Pro | Pro | Gly | Lys | Gly | Leu | Glu |
|---|---|---|---|---|---|---|---|---|---|---|---|---|---|---|---|
| | | 35 | | | | | 40 | | | | | 45 | | | |

| Trp | Ile | Gly | Asn | Ile | Tyr | Tyr | Ser | Gly | Ser | Thr | Tyr | Tyr | Asn | Pro | Ser |
|---|---|---|---|---|---|---|---|---|---|---|---|---|---|---|---|
| 50 | | | | | 55 | | | | | 60 | | | | | |

| Leu | Arg | Gly | Arg | Val | Thr | Ile | Ser | Val | Asp | Thr | Ser | Lys | Asn | Gln | Phe |
|---|---|---|---|---|---|---|---|---|---|---|---|---|---|---|---|
| 65 | | | | | 70 | | | | | 75 | | | | | 80 |

| Ser | Leu | Lys | Leu | Ser | Ser | Val | Thr | Ala | Ala | Asp | Thr | Ala | Val | Tyr | Tyr |
|---|---|---|---|---|---|---|---|---|---|---|---|---|---|---|---|
| | | | | 85 | | | | | 90 | | | | | 95 | |

| Cys | Ala | Arg | Leu | Gly | His | Gly | Tyr | Asn | Tyr | Phe | Asp | Leu | Trp | Gly | Arg |
|---|---|---|---|---|---|---|---|---|---|---|---|---|---|---|---|
| | | | 100 | | | | | 105 | | | | | 110 | | |

| Gly | Thr | Leu | Val | Thr | Val | Ser | Ser |
|---|---|---|---|---|---|---|---|
| | | 115 | | | | | 120 |

<210> SEQ ID NO 141
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 141

| Gln | Leu | Gln | Leu | Gln | Glu | Ser | Gly | Pro | Gly | Leu | Val | Lys | Pro | Ser | Glu |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Thr | Val | Ser | Gly | Gly | Ser | Ile | Ser | Ser | Ser |
|---|---|---|---|---|---|---|---|---|---|---|---|---|---|---|---|
| | | | 20 | | | | | 25 | | | | | 30 | | |

| Ser | His | Tyr | Trp | Gly | Trp | Ile | Arg | Gln | Pro | Pro | Gly | Lys | Gly | Leu | Glu |
|---|---|---|---|---|---|---|---|---|---|---|---|---|---|---|---|
| | | 35 | | | | | 40 | | | | | 45 | | | |

| Trp | Ile | Gly | Met | Ile | Tyr | Tyr | Ser | Gly | Ser | Thr | Trp | Tyr | Asn | Pro | Ser |
|---|---|---|---|---|---|---|---|---|---|---|---|---|---|---|---|
| 50 | | | | | 55 | | | | | 60 | | | | | |

| Leu | Lys | Ser | Arg | Val | Thr | Ile | Ser | Val | Asp | Thr | Ser | Lys | Asn | Gln | Phe |
|---|---|---|---|---|---|---|---|---|---|---|---|---|---|---|---|
| 65 | | | | | 70 | | | | | 75 | | | | | 80 |

| Ser | Leu | Lys | Leu | Ser | Ser | Val | Thr | Ala | Ala | Asp | Thr | Ala | Val | Tyr | Tyr |
|---|---|---|---|---|---|---|---|---|---|---|---|---|---|---|---|
| | | | | 85 | | | | | 90 | | | | | 95 | |

| Cys | Ala | Arg | Val | Gly | His | Gly | Val | Ser | Tyr | Phe | Asp | Leu | Trp | Gly | Arg |
|---|---|---|---|---|---|---|---|---|---|---|---|---|---|---|---|
| | | | 100 | | | | | 105 | | | | | 110 | | |

| Gly | Thr | Leu | Val | Thr | Val | Ser | Ser |
|---|---|---|---|---|---|---|---|
| | | 115 | | | | | 120 |

<210> SEQ ID NO 142
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 142

| Gln | Leu | Gln | Leu | Gln | Glu | Ser | Gly | Pro | Gly | Leu | Val | Lys | Pro | Ser | Glu |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Thr | Val | Ser | Gly | Gly | Ser | Ile | Ser | Arg | Gly |
|---|---|---|---|---|---|---|---|---|---|---|---|---|---|---|---|
| | | | 20 | | | | | 25 | | | | | 30 | | |

```
Ser Tyr Tyr Trp Gly Trp Ile Arg Gln Pro Pro Gly Lys Gly Leu Glu
        35                  40                  45

Trp Ile Gly Met Ile Tyr Tyr Ser Gly Ser Thr Trp Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Val Gly His Gly Ile Ser Tyr Phe Asp Leu Trp Gly Arg
                100                 105                 110

Gly Thr Leu Val Thr Val Ser Ser
        115                 120

<210> SEQ ID NO 143
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 143

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Arg Gly
             20                  25                  30

Ser Tyr Tyr Trp Gly Trp Ile Arg Gln Pro Pro Gly Lys Gly Leu Glu
        35                  40                  45

Trp Ile Gly Met Ile Tyr Tyr Ser Gly Ser Thr Trp Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Val Gly His Gly Val Ser Tyr Phe Asp Leu Trp Gly Arg
                100                 105                 110

Gly Thr Leu Val Thr Val Ser Ser
        115                 120

<210> SEQ ID NO 144
<211> LENGTH: 120
<212> TYPE: PRT
<213> ORGANISM: Artificial Sequence
<220> FEATURE:
<223> OTHER INFORMATION: Synthetic: VH sequence

<400> SEQUENCE: 144

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Thr Ser Ser Ser
             20                  25                  30

Ser Tyr Tyr Trp Gly Trp Ile Arg Gln Pro Pro Gly Lys Gly Leu Glu
        35                  40                  45

Trp Ile Gly Ser Ile Tyr Arg Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80
```

```
Ser Leu Lys Leu Ser Ser Val Thr Ala Ala Asp Thr Ala Val Tyr Tyr
                85                  90                  95

Cys Ala Arg Val Gly His Gly Ile Ser Tyr Phe Asp Leu Trp Gly Arg
            100                 105                 110

Gly Thr Leu Val Thr Val Ser Ser
        115                 120

<210> SEQ ID NO 145
<211> LENGTH: 120
<212> TYPE: PRT
<213> ORGANISM: Artificial Sequence
<220> FEATURE:
<223> OTHER INFORMATION: Synthetic:  VH sequence

<400> SEQUENCE: 145

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Thr Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Arg Ser Gly Ser Thr Tyr Tyr Asn Pro Ser
    50                  55                  60

Phe Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Gly His Gly Ile Ser Tyr Phe Asp Leu Trp Gly Arg
            100                 105                 110

Gly Thr Leu Val Thr Val Ser Ser
        115                 120

<210> SEQ ID NO 146
<211> LENGTH: 120
<212> TYPE: PRT
<213> ORGANISM: Artificial Sequence
<220> FEATURE:
<223> OTHER INFORMATION: Synthetic:  VH sequence

<400> SEQUENCE: 146

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Thr Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Arg Ser Gly Ser Thr Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Gly His Gly Ile Ser Tyr Phe Asp Leu Trp Gly Arg
            100                 105                 110

Gly Thr Leu Val Thr Val Ser Ser
        115                 120
```

```
<210> SEQ ID NO 147
<211> LENGTH: 119
<212> TYPE: PRT
<213> ORGANISM: Artificial Sequence
<220> FEATURE:
<223> OTHER INFORMATION: Synthetic: VH sequence

<400> SEQUENCE: 147

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Ser Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Val Arg Val Arg His Tyr Gly Met Asp Val Trp Gly Gln Gly
            100                 105                 110

Thr Thr Val Thr Val Ser Ser
        115

<210> SEQ ID NO 148
<211> LENGTH: 107
<212> TYPE: PRT
<213> ORGANISM: Artificial Sequence
<220> FEATURE:
<223> OTHER INFORMATION: Synthetic: VL sequence

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Val Pro Leu
                85                  90                  95

Thr Phe Gly Gly Gly Thr Lys Val Glu Ile Lys
            100                 105

<210> SEQ ID NO 149
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

```
Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Asp Glu Ser Tyr Ser Thr Pro Pro
                85                  90                  95

Trp Thr Phe Gly Gly Gly Thr Lys Val Glu Ile Lys
                100                 105

<210> SEQ ID NO 150
<211> LENGTH: 107
<212> TYPE: PRT
<213> ORGANISM: Artificial Sequence
<220> FEATURE:
<223> OTHER INFORMATION: Synthetic: VL sequence

<400> SEQUENCE: 150

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Val Gln Arg Ser Asn Phe Pro Trp
                85                  90                  95

Thr Phe Gly Gly Gly Thr Lys Val Glu Ile Lys
                100                 105

<210> SEQ ID NO 151
<211> LENGTH: 107
<212> TYPE: PRT
<213> ORGANISM: Artificial Sequence
<220> FEATURE:
<223> OTHER INFORMATION: Synthetic: VL sequence

<400> SEQUENCE: 151

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Phe Pro Phe
                85                  90                  95

Thr Phe Gly Gly Gly Thr Lys Val Glu Ile Lys
                100                 105
```

```
<210> SEQ ID NO 152
<211> LENGTH: 107
<212> TYPE: PRT
<213> ORGANISM: Artificial Sequence
<220> FEATURE:
<223> OTHER INFORMATION: Synthetic: VL sequence

<400> SEQUENCE: 152

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Val Asn Phe Pro Phe
                85                  90                  95

Thr Phe Gly Gly Gly Thr Lys Val Glu Ile Lys
            100                 105

<210> SEQ ID NO 153
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 153

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ala Val Val Trp Pro Pro
                85                  90                  95

Arg Thr Phe Gly Gly Gly Thr Lys Val Glu Ile Lys
            100                 105

<210> SEQ ID NO 154
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 154

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45
```

```
Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Tyr Thr Trp Pro Pro
                85                  90                  95

Arg Thr Phe Gly Gly Gly Thr Lys Val Glu Ile Lys
            100                 105
```

```
<210> SEQ ID NO 155
<211> LENGTH: 108
<212> TYPE: PRT
<213> ORGANISM: Artificial Sequence
<220> FEATURE:
<223> OTHER INFORMATION: Synthetic:  VL sequence

<400> SEQUENCE: 155

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Tyr Leu Trp Pro Pro
                85                  90                  95

Arg Thr Phe Gly Gly Gly Thr Lys Val Glu Ile Lys
            100                 105
```

```
<210> SEQ ID NO 156
<211> LENGTH: 108
<212> TYPE: PRT
<213> ORGANISM: Artificial Sequence
<220> FEATURE:
<223> OTHER INFORMATION: Synthetic:  VL sequence

<400> SEQUENCE: 156

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105
```

```
<210> SEQ ID NO 157
<211> LENGTH: 108
<212> TYPE: PRT
```

<213> ORGANISM: Artificial Sequence
<220> FEATURE:
<223> OTHER INFORMATION: Synthetic: VL sequence

<400> SEQUENCE: 157

```
Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Leu Phe Leu Trp Pro Pro
                85                  90                  95
Arg Thr Phe Gly Gly Gly Thr Lys Val Glu Ile Lys
            100                 105
```

<210> SEQ ID NO 158
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 158

```
Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Leu Leu Leu Trp Pro Pro
                85                  90                  95
Arg Thr Phe Gly Gly Gly Thr Lys Val Glu Ile Lys
            100                 105
```

<210> SEQ ID NO 159
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 159

```
Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Ile Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
```

```
Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Leu Leu Trp Pro Pro
                85                  90                  95

Arg Thr Phe Gly Gly Gly Thr Lys Val Glu Ile Lys
                100                 105
```

<210> SEQ ID NO 160
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 160

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser His
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Ile Leu Trp Pro Pro
                85                  90                  95

Arg Thr Phe Gly Gly Gly Thr Lys Val Glu Ile Lys
                100                 105
```

<210> SEQ ID NO 161
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 161

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ala Tyr Val Trp Pro Pro
                85                  90                  95

Arg Thr Phe Gly Gly Gly Thr Lys Val Glu Ile Lys
                100                 105
```

<210> SEQ ID NO 162
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 162

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Leu Thr Trp Pro Pro
                85                  90                  95

Arg Thr Phe Gly Gly Gly Thr Lys Val Glu Ile Lys
            100                 105

<210> SEQ ID NO 163
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 163

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Val Tyr Thr Trp Pro Pro
                85                  90                  95

Arg Thr Phe Gly Gly Gly Thr Lys Val Glu Ile Lys
            100                 105

<210> SEQ ID NO 164
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 164

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Val Tyr Thr Trp Pro Pro
                85                  90                  95

Arg Thr Phe Gly Gly Gly Thr Lys Val Glu Ile Lys
            100                 105

<210> SEQ ID NO 165
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 165

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Val Tyr Leu Trp Pro Pro
                85                  90                  95

Arg Thr Phe Gly Gly Gly Thr Lys Val Glu Ile Lys
            100                 105

<210> SEQ ID NO 166
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 166

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Phe Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Val Tyr Val Trp Pro Pro
                85                  90                  95

Arg Thr Phe Gly Gly Gly Thr Lys Val Glu Ile Lys
            100                 105

<210> SEQ ID NO 167
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 167

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ile Thr Trp Pro Pro
                85                  90                  95

Arg Thr Phe Gly Gly Gly Thr Lys Val Glu Ile Lys
            100                 105

<210> SEQ ID NO 168
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 168

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Val Thr Trp Pro Pro
                85                  90                  95

Arg Thr Phe Gly Gly Gly Thr Lys Val Glu Ile Lys
            100                 105

<210> SEQ ID NO 169
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 169

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Leu Val Trp Pro Pro
                85                  90                  95

Arg Thr Phe Gly Gly Gly Thr Lys Val Glu Ile Lys
            100                 105

<210> SEQ ID NO 170
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 170

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Arg Ser Val Asn Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Val Tyr Thr Trp Pro Pro
                85                  90                  95

Arg Thr Phe Gly Gly Gly Thr Lys Val Glu Ile Lys
            100                 105

<210> SEQ ID NO 171
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 171

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ile Val Trp Pro Pro
                85                  90                  95

Arg Thr Phe Gly Gly Gly Thr Lys Val Glu Ile Lys
            100                 105

<210> SEQ ID NO 172
<211> LENGTH: 108
<212> TYPE: PRT
<213> ORGANISM: Artificial Sequence
<220> FEATURE:
<223> OTHER INFORMATION: Synthetic: VL sequence

<400> SEQUENCE: 172

Gly Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Tyr Thr Trp Pro Pro
                85                  90                  95

Arg Thr Phe Gly Gly Gly Thr Lys Val Glu Ile Lys
            100                 105

<210> SEQ ID NO 173
<211> LENGTH: 108
<212> TYPE: PRT
<213> ORGANISM: Artificial Sequence
<220> FEATURE:
<223> OTHER INFORMATION: Synthetic:  VL sequence

<400> SEQUENCE: 173

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Phe Leu Trp Pro Pro
                85                  90                  95

Arg Thr Phe Gly Gly Gly Thr Lys Val Glu Ile Lys
            100                 105

<210> SEQ ID NO 174
<211> LENGTH: 108
<212> TYPE: PRT
<213> ORGANISM: Artificial Sequence
<220> FEATURE:
<223> OTHER INFORMATION: Synthetic:  VL sequence

<400> SEQUENCE: 174

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Phe Val Trp Pro Pro
                85                  90                  95

Arg Thr Phe Gly Gly Gly Thr Lys Val Glu Ile Lys
                100                 105

<210> SEQ ID NO 175
<211> LENGTH: 108
<212> TYPE: PRT
<213> ORGANISM: Artificial Sequence
<220> FEATURE:
<223> OTHER INFORMATION: Synthetic:  VL sequence

<400> SEQUENCE: 175

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Phe Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Leu Thr Trp Pro Pro
                85                  90                  95

Arg Thr Phe Gly Gly Gly Thr Lys Val Glu Ile Lys
                100                 105

<210> SEQ ID NO 176
<211> LENGTH: 108
<212> TYPE: PRT
<213> ORGANISM: Artificial Sequence
<220> FEATURE:
<223> OTHER INFORMATION: Synthetic:  VL sequence

<400> SEQUENCE: 176

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Leu Val Trp Pro Pro
                85                  90                  95

Arg Thr Phe Gly Gly Gly Ala Lys Val Glu Ile Lys
                100                 105

<210> SEQ ID NO 177
<211> LENGTH: 108
<212> TYPE: PRT
<213> ORGANISM: Artificial Sequence
<220> FEATURE:
<223> OTHER INFORMATION: Synthetic:  VL sequence

<400> SEQUENCE: 177

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Ser Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Leu Thr Trp Pro Pro
                85                  90                  95

Arg Thr Phe Gly Gly Gly Thr Lys Val Glu Ile Lys
            100                 105

<210> SEQ ID NO 178
<211> LENGTH: 107
<212> TYPE: PRT
<213> ORGANISM: Artificial Sequence
<220> FEATURE:
<223> OTHER INFORMATION: Synthetic:  VL sequence

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Leu Ser His Pro Arg
                85                  90                  95

Thr Phe Gly Gly Gly Thr Lys Val Glu Ile Lys
            100                 105

<210> SEQ ID NO 179
<211> LENGTH: 501
<212> TYPE: PRT
<213> ORGANISM: Homo sapiens
<220> FEATURE:
<221> NAME/KEY: misc_feature
<223> OTHER INFORMATION: Human BACE1, isoform B

<400> SEQUENCE: 179

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
50                  55                  60

```
Asp Asn Leu Arg Gly Lys Ser Gly Gln Gly Tyr Tyr Val Glu Met Thr
 65                  70                  75                  80

Val Gly Ser Pro Pro Gln Thr Leu Asn Ile Leu Val Asp Thr Gly Ser
                 85                  90                  95

Ser Asn Phe Ala Val Gly Ala Ala Pro His Pro Phe Leu His Arg Tyr
                100                 105                 110

Tyr Gln Arg Gln Leu Ser Ser Thr Tyr Arg Asp Leu Arg Lys Gly Val
            115                 120                 125

Tyr Val Pro Tyr Thr Gln Gly Lys Trp Glu Gly Glu Leu Gly Thr Asp
        130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
                180                 185                 190

Ser Leu Glu Pro Phe Phe Asp Ser Leu Val Lys Gln Thr His Val Pro
            195                 200                 205

Asn Leu Phe Ser Leu Gln Leu Cys Gly Ala Gly Phe Pro Leu Asn Gln
        210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
                260                 265                 270

Asp Leu Lys Met Asp Cys Lys Glu Tyr Asn Tyr Asp Lys Ser Ile Val
            275                 280                 285

Asp Ser Gly Thr Thr Asn Leu Arg Leu Pro Lys Lys Val Phe Glu Ala
        290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
                340                 345                 350

Thr Asn Gln Ser Phe Arg Ile Thr Ile Leu Pro Gln Gln Tyr Leu Arg
            355                 360                 365

Pro Val Glu Asp Val Ala Thr Ser Gln Asp Asp Cys Tyr Lys Phe Ala
        370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
                420                 425                 430

Gly Pro Phe Val Thr Leu Asp Met Glu Asp Cys Gly Tyr Asn Ile Pro
            435                 440                 445

Gln Thr Asp Glu Ser Thr Leu Met Thr Ile Ala Tyr Val Met Ala Ala
        450                 455                 460

Ile Cys Ala Leu Phe Met Leu Pro Leu Cys Leu Met Val Cys Gln Trp
465                 470                 475                 480
```

```
Cys Cys Leu Arg Cys Leu Arg Gln Gln His Asp Asp Phe Ala Asp Asp
            485                 490                 495

Ile Ser Leu Leu Lys
            500

<210> SEQ ID NO 180
<211> LENGTH: 476
<212> TYPE: PRT
<213> ORGANISM: Homo sapiens
<220> FEATURE:
<221> NAME/KEY: misc_feature
<223> OTHER INFORMATION: Human BACE1, isoform A

<400> SEQUENCE: 180

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Leu Cys Gly
            180                 185                 190

Ala Gly Phe Pro Leu Asn Gln Ser Glu Val Leu Ala Ser Val Gly Gly
        195                 200                 205

Ser Met Ile Ile Gly Gly Ile Asp His Ser Leu Tyr Thr Gly Ser Leu
    210                 215                 220

Trp Tyr Thr Pro Ile Arg Arg Glu Trp Tyr Tyr Glu Val Ile Ile Val
225                 230                 235                 240

Arg Val Glu Ile Asn Gly Gln Asp Leu Lys Met Asp Cys Lys Glu Tyr
                245                 250                 255

Asn Tyr Asp Lys Ser Ile Val Asp Ser Gly Thr Thr Asn Leu Arg Leu
            260                 265                 270

Pro Lys Lys Val Phe Glu Ala Ala Val Lys Ser Ile Lys Ala Ala Ser
        275                 280                 285

Ser Thr Glu Lys Phe Pro Asp Gly Phe Trp Leu Gly Glu Gln Leu Val
    290                 295                 300

Cys Trp Gln Ala Gly Thr Thr Pro Trp Asn Ile Phe Pro Val Ile Ser
305                 310                 315                 320

Leu Tyr Leu Met Gly Glu Val Thr Asn Gln Ser Phe Arg Ile Thr Ile
                325                 330                 335
```

-continued

```
Leu Pro Gln Gln Tyr Leu Arg Pro Val Glu Asp Val Ala Thr Ser Gln
            340                 345                 350

Asp Asp Cys Tyr Lys Phe Ala Ile Ser Gln Ser Ser Thr Gly Thr Val
            355                 360                 365

Met Gly Ala Val Ile Met Glu Gly Phe Tyr Val Val Phe Asp Arg Ala
            370                 375                 380

Arg Lys Arg Ile Gly Phe Ala Val Ser Ala Cys His Val His Asp Glu
385                 390                 395                 400

Phe Arg Thr Ala Ala Val Glu Gly Pro Phe Val Thr Leu Asp Met Glu
                405                 410                 415

Asp Cys Gly Tyr Asn Ile Pro Gln Thr Asp Glu Ser Thr Leu Met Thr
            420                 425                 430

Ile Ala Tyr Val Met Ala Ala Ile Cys Ala Leu Phe Met Leu Pro Leu
            435                 440                 445

Cys Leu Met Val Cys Gln Trp Cys Cys Leu Arg Cys Leu Arg Gln Gln
            450                 455                 460

His Asp Asp Phe Ala Asp Asp Ile Ser Leu Leu Lys
465                 470                 475
```

<210> SEQ ID NO 181
<211> LENGTH: 457
<212> TYPE: PRT
<213> ORGANISM: Homo sapiens
<220> FEATURE:
<221> NAME/KEY: misc_feature
<223> OTHER INFORMATION: Human BACE1, isoform C

<400> SEQUENCE: 181

```
Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
            35                  40                  45

Glu Glu Pro Glu Glu Pro Gly Arg Arg Gly Ser Phe Val Glu Met Val
            50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
            85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
            115                 120                 125

Tyr Val Pro Tyr Thr Gln Gly Lys Trp Glu Gly Glu Leu Gly Thr Asp
            130                 135                 140

Leu Pro Asp Asp Ser Leu Glu Pro Phe Phe Asp Ser Leu Val Lys Gln
145                 150                 155                 160

Thr His Val Pro Asn Leu Phe Ser Leu Gln Leu Cys Gly Ala Gly Phe
            165                 170                 175

Pro Leu Asn Gln Ser Glu Val Leu Ala Ser Val Gly Gly Ser Met Ile
            180                 185                 190

Ile Gly Gly Ile Asp His Ser Leu Tyr Thr Gly Ser Leu Trp Tyr Thr
            195                 200                 205
```

```
Pro Ile Arg Arg Glu Trp Tyr Tyr Glu Val Ile Ile Val Arg Val Glu
    210                 215                 220
Ile Asn Gly Gln Asp Leu Lys Met Asp Cys Lys Glu Tyr Asn Tyr Asp
225                 230                 235                 240
Lys Ser Ile Val Asp Ser Gly Thr Thr Asn Leu Arg Leu Pro Lys Lys
                245                 250                 255
Val Phe Glu Ala Ala Val Lys Ser Ile Lys Ala Ala Ser Ser Thr Glu
            260                 265                 270
Lys Phe Pro Asp Gly Phe Trp Leu Gly Glu Gln Leu Val Cys Trp Gln
        275                 280                 285
Ala Gly Thr Thr Pro Trp Asn Ile Phe Pro Val Ile Ser Leu Tyr Leu
    290                 295                 300
Met Gly Glu Val Thr Asn Gln Ser Phe Arg Ile Thr Ile Leu Pro Gln
305                 310                 315                 320
Gln Tyr Leu Arg Pro Val Glu Asp Val Ala Thr Ser Gln Asp Asp Cys
                325                 330                 335
Tyr Lys Phe Ala Ile Ser Gln Ser Ser Thr Gly Thr Val Met Gly Ala
            340                 345                 350
Val Ile Met Glu Gly Phe Tyr Val Val Phe Asp Arg Ala Arg Lys Arg
        355                 360                 365
Ile Gly Phe Ala Val Ser Ala Cys His Val His Asp Glu Phe Arg Thr
    370                 375                 380
Ala Ala Val Glu Gly Pro Phe Val Thr Leu Asp Met Glu Asp Cys Gly
385                 390                 395                 400
Tyr Asn Ile Pro Gln Thr Asp Glu Ser Thr Leu Met Thr Ile Ala Tyr
                405                 410                 415
Val Met Ala Ala Ile Cys Ala Leu Phe Met Leu Pro Leu Cys Leu Met
            420                 425                 430
Val Cys Gln Trp Cys Cys Leu Arg Cys Leu Arg Gln Gln His Asp Asp
        435                 440                 445
Phe Ala Asp Asp Ile Ser Leu Leu Lys
    450                 455

<210> SEQ ID NO 182
<211> LENGTH: 432
<212> TYPE: PRT
<213> ORGANISM: Homo sapiens
<220> FEATURE:
<221> NAME/KEY: misc_feature
<223> OTHER INFORMATION: Human BACE1, isoform D

<400> SEQUENCE: 182

Met Ala Gln Ala Leu Pro Trp Leu Leu Leu Trp Met Gly Ala Gly Val
1               5                   10                  15
Leu Pro Ala His Gly Thr Gln His Gly Ile Arg Leu Pro Leu Arg Ser
            20                  25                  30
Gly Leu Gly Gly Ala Pro Leu Gly Leu Arg Leu Pro Arg Glu Thr Asp
        35                  40                  45
Glu Glu Pro Glu Glu Pro Gly Arg Arg Gly Ser Phe Val Glu Met Val
    50                  55                  60
Asp Asn Leu Arg Gly Lys Ser Gly Gln Gly Tyr Tyr Val Glu Met Thr
65                  70                  75                  80
Val Gly Ser Pro Pro Gln Thr Leu Asn Ile Leu Val Asp Thr Gly Ser
                85                  90                  95
```

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Leu Cys Gly Ala Gly Phe Pro Leu Asn Gln Ser Glu Val Leu Ala
145                 150                 155                 160

Ser Val Gly Gly Ser Met Ile Ile Gly Gly Ile Asp His Ser Leu Tyr
                165                 170                 175

Thr Gly Ser Leu Trp Tyr Thr Pro Ile Arg Arg Glu Trp Tyr Tyr Glu
            180                 185                 190

Val Ile Ile Val Arg Val Glu Ile Asn Gly Gln Asp Leu Lys Met Asp
        195                 200                 205

Cys Lys Glu Tyr Asn Tyr Asp Lys Ser Ile Val Asp Ser Gly Thr Thr
    210                 215                 220

Asn Leu Arg Leu Pro Lys Lys Val Phe Glu Ala Ala Val Lys Ser Ile
225                 230                 235                 240

Lys Ala Ala Ser Ser Thr Glu Lys Phe Pro Asp Gly Phe Trp Leu Gly
                245                 250                 255

Glu Gln Leu Val Cys Trp Gln Ala Gly Thr Thr Pro Trp Asn Ile Phe
            260                 265                 270

Pro Val Ile Ser Leu Tyr Leu Met Gly Glu Val Thr Asn Gln Ser Phe
        275                 280                 285

Arg Ile Thr Ile Leu Pro Gln Gln Tyr Leu Arg Pro Val Glu Asp Val
    290                 295                 300

Ala Thr Ser Gln Asp Asp Cys Tyr Lys Phe Ala Ile Ser Gln Ser Ser
305                 310                 315                 320

Thr Gly Thr Val Met Gly Ala Val Ile Met Glu Gly Phe Tyr Val Val
                325                 330                 335

Phe Asp Arg Ala Arg Lys Arg Ile Gly Phe Ala Val Ser Ala Cys His
            340                 345                 350

Val His Asp Glu Phe Arg Thr Ala Ala Val Glu Gly Pro Phe Val Thr
        355                 360                 365

Leu Asp Met Glu Asp Cys Gly Tyr Asn Ile Pro Gln Thr Asp Glu Ser
    370                 375                 380

Thr Leu Met Thr Ile Ala Tyr Val Met Ala Ala Ile Cys Ala Leu Phe
385                 390                 395                 400

Met Leu Pro Leu Cys Leu Met Val Cys Gln Trp Cys Cys Leu Arg Cys
                405                 410                 415

Leu Arg Gln Gln His Asp Asp Phe Ala Asp Asp Ile Ser Leu Leu Lys
            420                 425                 430

<210> SEQ ID NO 183
<211> LENGTH: 27
<212> TYPE: PRT
<213> ORGANISM: Artificial Sequence
<220> FEATURE:
<223> OTHER INFORMATION: Synthetic: Bi27 peptide
<220> FEATURE:
<221> NAME/KEY: MOD_RES
<222> LOCATION: (1)..(1)
<223> OTHER INFORMATION: Biotin on 5' end

```
<400> SEQUENCE: 183

Lys Thr Glu Glu Ile Ser Glu Val Asn Leu Asp Ala Glu Phe Arg His
1               5                   10                  15

Asp Ser Gly Tyr Glu Val His His Gln Lys Leu
            20                  25

<210> SEQ ID NO 184
<211> LENGTH: 13
<212> TYPE: PRT
<213> ORGANISM: Artificial Sequence
<220> FEATURE:
<223> OTHER INFORMATION: Synthetic:  FRET short substrate (R&D Systems)
<220> FEATURE:
<221> NAME/KEY: MOD_RES
<222> LOCATION: (1)..(1)
<223> OTHER INFORMATION: Mca ((7-Methoxycoumarin-4-yl)acetyl) on 5' end
<220> FEATURE:
<221> NAME/KEY: MOD_RES
<222> LOCATION: (11)..(11)
<223> OTHER INFORMATION: Dnp: 2, 4-Dinitrophenyl
<220> FEATURE:
<221> NAME/KEY: MOD_RES
<222> LOCATION: (13)..(13)
<223> OTHER INFORMATION: NH2 at 3' end

<400> SEQUENCE: 184

Ser Glu Val Asn Leu Asp Ala Glu Phe Arg Lys Arg Arg
1               5                   10

<210> SEQ ID NO 185
<211> LENGTH: 9
<212> TYPE: PRT
<213> ORGANISM: Artificial Sequence
<220> FEATURE:
<223> OTHER INFORMATION: Synthetic:  FRET short substrate (Invitrogen)
<220> FEATURE:
<221> NAME/KEY: MOD_RES
<222> LOCATION: (1)..(1)
<223> OTHER INFORMATION: Rh on 5' end
<220> FEATURE:
<221> NAME/KEY: MOD_RES
<222> LOCATION: (9)..(9)
<223> OTHER INFORMATION: Quencher on 3' end

<400> SEQUENCE: 185

Glu Val Asn Leu Asp Ala Glu Phe Lys
1               5

<210> SEQ ID NO 186
<211> LENGTH: 18
<212> TYPE: PRT
<213> ORGANISM: Artificial Sequence
<220> FEATURE:
<223> OTHER INFORMATION: Synthetic:  amyloid precursor protein beta
      secretase active site peptide
<220> FEATURE:
<221> NAME/KEY: MOD_RES
<222> LOCATION: (1)..(1)
<223> OTHER INFORMATION: FAM on 5' end
<220> FEATURE:
<221> NAME/KEY: MOD_RES
<222> LOCATION: (18)..(18)
<223> OTHER INFORMATION: CONH2 on 3' end

<400> SEQUENCE: 186

Lys Thr Glu Glu Ile Ser Glu Val Asn Leu Asp Ala Glu Phe Arg Trp
1               5                   10                  15

Lys Lys
```

Figure 12A:
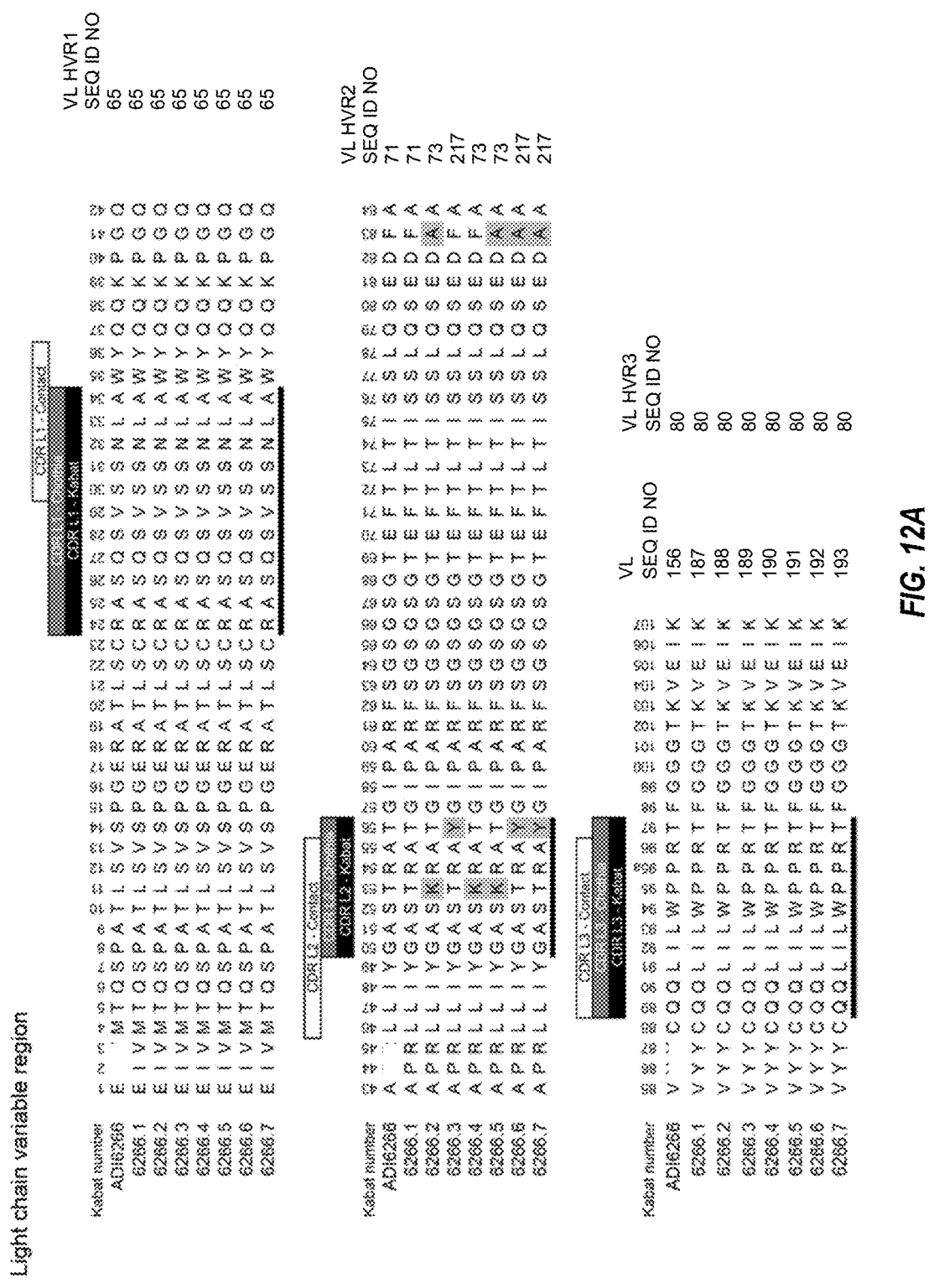

<210> SEQ ID NO 187
<211> LENGTH: 108
<212> TYPE: PRT
<213> ORGANISM: Artificial Sequence
<220> FEATURE:
<223> OTHER INFORMATION: Synthetic: Fig. 12A Light Chain Variable
      Region: 6266.1

<400> SEQUENCE: 187

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 188
<211> LENGTH: 108
<212> TYPE: PRT
<213> ORGANISM: Artificial Sequence
<220> FEATURE:
<223> OTHER INFORMATION: Synthetic: Fig. 12A Light Chain Variable
      Region: 6266.2

<400> SEQUENCE: 188

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Lys Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Ala Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 189
<211> LENGTH: 108
<212> TYPE: PRT
<213> ORGANISM: Artificial Sequence
<220> FEATURE:
<223> OTHER INFORMATION: Synthetic: Fig. 12A Light Chain Variable
      Region: 6266.3

<400> SEQUENCE: 189

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Tyr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 190
<211> LENGTH: 108
<212> TYPE: PRT
<213> ORGANISM: Artificial Sequence
<220> FEATURE:
<223> OTHER INFORMATION: Synthetic: Fig. 12A Light Chain Variable
      Region: 6266.4

<400> SEQUENCE: 190

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Lys Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 191
<211> LENGTH: 108
<212> TYPE: PRT
<213> ORGANISM: Artificial Sequence
<220> FEATURE:
<223> OTHER INFORMATION: Synthetic: Fig. 12A Light Chain Variable
      Region: 6266.5

<400> SEQUENCE: 191

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Lys Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Ala Ala Val Tyr Tyr Cys Gln Gln Leu Ile Leu Trp Pro Pro
                85                  90                  95

```
Arg Thr Phe Gly Gly Gly Thr Lys Val Glu Ile Lys
            100                 105

<210> SEQ ID NO 192
<211> LENGTH: 108
<212> TYPE: PRT
<213> ORGANISM: Artificial Sequence
<220> FEATURE:
<223> OTHER INFORMATION: Synthetic:  Fig. 12A Light Chain Variable
      Region: 6266.6

<400> SEQUENCE: 192

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Tyr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Ala Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 193
<211> LENGTH: 108
<212> TYPE: PRT
<213> ORGANISM: Artificial Sequence
<220> FEATURE:
<223> OTHER INFORMATION: Synthetic:  Fig. 12A Light Chain Variable
      Region: 6266.7

<400> SEQUENCE: 193

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Tyr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Ala Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 194
<211> LENGTH: 120
<212> TYPE: PRT
<213> ORGANISM: Artificial Sequence
<220> FEATURE:
<223> OTHER INFORMATION: Synthetic:  Fig. 12B Heavy Chain Variable
      Region: 6266.1
```

<400> SEQUENCE: 194

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser His Tyr
            20                  25                  30

Gly Val Ser Trp Val Arg Gln Ala Pro Gly Gln Gly Leu Glu Trp Met
        35                  40                  45

Gly Asn Ile Ile Pro Gly Ile Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
        115                 120

<210> SEQ ID NO 195
<211> LENGTH: 120
<212> TYPE: PRT
<213> ORGANISM: Artificial Sequence
<220> FEATURE:
<223> OTHER INFORMATION: Synthetic: Fig. 12B Heavy Chain Variable
      Region: 6266.2

<400> SEQUENCE: 195

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser His Tyr
            20                  25                  30

Gly Val Ser Trp Val Arg Gln Ala Pro Gly Gln Gly Leu Glu Trp Met
        35                  40                  45

Gly Asn Ile Ile Pro Gly Ile Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
        115                 120

<210> SEQ ID NO 196
<211> LENGTH: 120
<212> TYPE: PRT
<213> ORGANISM: Artificial Sequence
<220> FEATURE:
<223> OTHER INFORMATION: Synthetic: Fig. 12B Heavy Chain Variable
      Region: 6266.3

<400> SEQUENCE: 196

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser His Tyr
            20                  25                  30

Gly Val Ser Trp Val Arg Gln Ala Pro Gly Gln Gly Leu Glu Trp Met
            35                  40                  45

Gly Asn Ile Ile Pro Gly Ile Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
            115                 120

<210> SEQ ID NO 197
<211> LENGTH: 120
<212> TYPE: PRT
<213> ORGANISM: Artificial Sequence
<220> FEATURE:
<223> OTHER INFORMATION: Synthetic: Fig. 12B Heavy Chain Variable
      Region: 6266.4

<400> SEQUENCE: 197

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser His Tyr
            20                  25                  30

Gly Val Ser Trp Val Arg Gln Ala Pro Gly Gln Gly Leu Glu Trp Met
            35                  40                  45

Gly Asn Ile Ile Pro Gly Ile Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
            115                 120

<210> SEQ ID NO 198
<211> LENGTH: 120
<212> TYPE: PRT
<213> ORGANISM: Artificial Sequence
<220> FEATURE:
<223> OTHER INFORMATION: Synthetic: Fig. 12B Heavy Chain Variable
      Region: 6266.5

<400> SEQUENCE: 198

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser His Tyr
            20                  25                  30

Gly Val Ser Trp Val Arg Gln Ala Pro Gly Gln Gly Leu Glu Trp Met
            35                  40                  45

Gly Asn Ile Ile Pro Gly Ile Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                 85                  90                  95

Ala Arg Ser Gly Gly Thr Gln Tyr Gly Met Leu Asp Val Trp Gly Gln
            100                 105                 110

Gly Thr Met Val Thr Val Ser Ser
        115                 120

<210> SEQ ID NO 199
<211> LENGTH: 120
<212> TYPE: PRT
<213> ORGANISM: Artificial Sequence
<220> FEATURE:
<223> OTHER INFORMATION: Synthetic:  Fig. 12B Heavy Chain Variable
      Region: 6266.6

<400> SEQUENCE: 199

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser His Tyr
            20                  25                  30

Gly Val Ser Trp Val Arg Gln Ala Pro Gly Gln Gly Leu Glu Trp Met
        35                  40                  45

Gly Asn Ile Ile Pro Gly Ile Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Ala Arg Ser Gly Gly Thr Gln Tyr Gly Met Leu Asp Val Trp Gly Gln
            100                 105                 110

Gly Thr Met Val Thr Val Ser Ser
        115                 120

<210> SEQ ID NO 200
<211> LENGTH: 120
<212> TYPE: PRT
<213> ORGANISM: Artificial Sequence
<220> FEATURE:
<223> OTHER INFORMATION: Synthetic:  Fig. 12B Heavy Chain Variable
      Region: 6266.7

<400> SEQUENCE: 200

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser His Tyr
            20                  25                  30

Gly Val Ser Trp Val Arg Gln Ala Pro Gly Gln Gly Leu Glu Trp Met
        35                  40                  45

Gly Asn Ile Ile Pro Gly Ile Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Ala Arg Ser Gly Gly Thr Lys Tyr Gly Glu Leu Asp Val Trp Gly Gln
            100                 105                 110

Gly Thr Met Val Thr Val Ser Ser
        115                 120
```

Figure 13A:
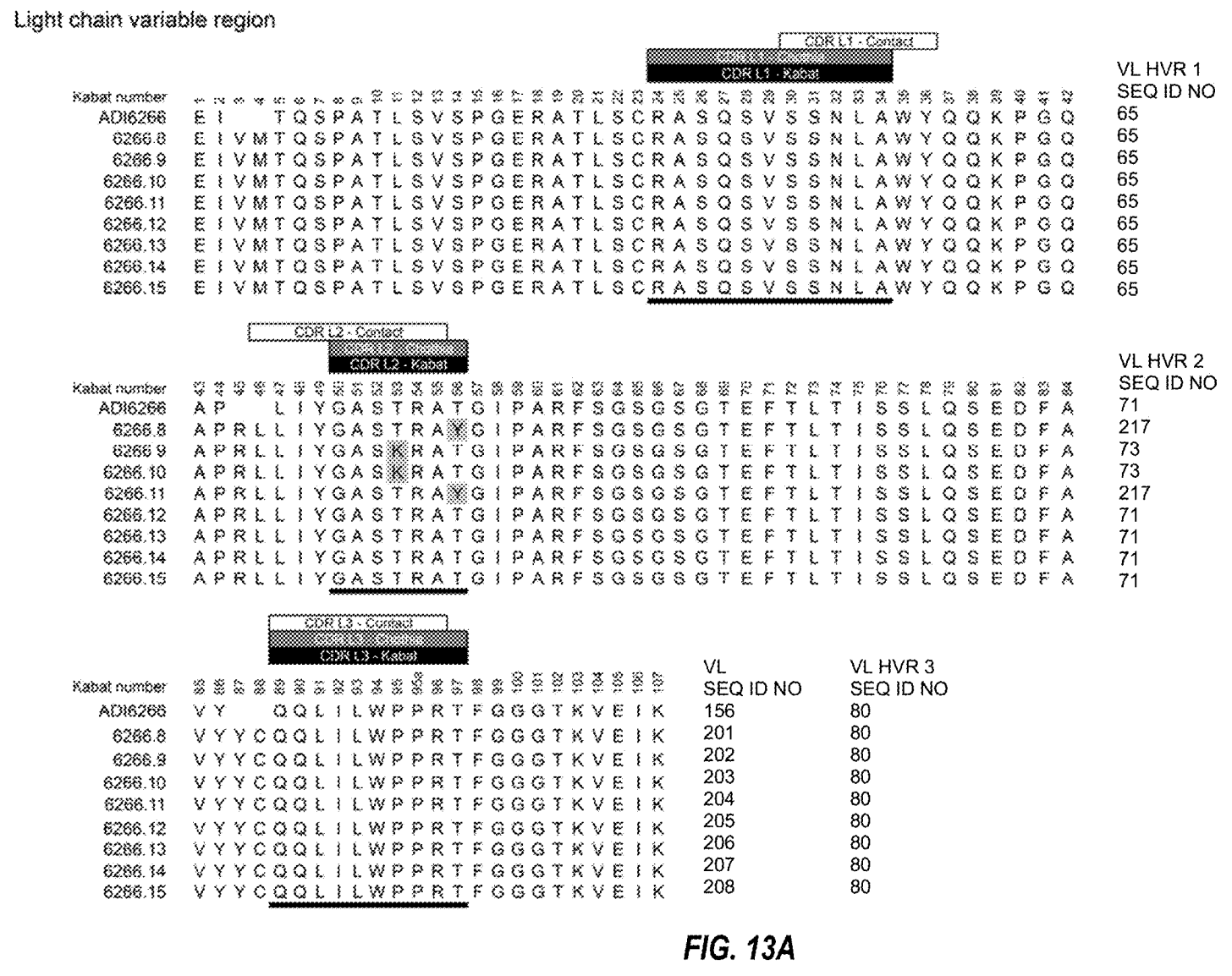

<210> SEQ ID NO 201
<211> LENGTH: 108
<212> TYPE: PRT
<213> ORGANISM: Artificial Sequence
<220> FEATURE:
<223> OTHER INFORMATION: Synthetic: Fig. 13A Light Chain Variable
      Region: 6266.8

<400> SEQUENCE: 201

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Tyr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 202
<211> LENGTH: 108
<212> TYPE: PRT
<213> ORGANISM: Artificial Sequence
<220> FEATURE:
<223> OTHER INFORMATION: Synthetic: Fig. 13A Light Chain Variable
      Region: 6266.9

<400> SEQUENCE: 202

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Lys Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 203
<211> LENGTH: 108
<212> TYPE: PRT
<213> ORGANISM: Artificial Sequence
<220> FEATURE:
<223> OTHER INFORMATION: Synthetic: Fig. 13A Light Chain Variable
      Region: 6266.1

<400> SEQUENCE: 203

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Lys Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 204
<211> LENGTH: 108
<212> TYPE: PRT
<213> ORGANISM: Artificial Sequence
<220> FEATURE:
<223> OTHER INFORMATION: Synthetic:  Fig. 13A Light Chain Variable
      Region: 6266.11

<400> SEQUENCE: 204

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Tyr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 205
<211> LENGTH: 108
<212> TYPE: PRT
<213> ORGANISM: Artificial Sequence
<220> FEATURE:
<223> OTHER INFORMATION: Synthetic:  Fig. 13A Light Chain Variable
      Region: 6266.12

<400> SEQUENCE: 205

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 206
<211> LENGTH: 108
<212> TYPE: PRT
<213> ORGANISM: Artificial Sequence
<220> FEATURE:
<223> OTHER INFORMATION: Synthetic: Fig. 13A Light Chain Variable
      Region: 6266.13

<400> SEQUENCE: 206

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 207
<211> LENGTH: 108
<212> TYPE: PRT
<213> ORGANISM: Artificial Sequence
<220> FEATURE:
<223> OTHER INFORMATION: Synthetic: Fig. 13A Light Chain Variable
      Region: 6266.14

<400> SEQUENCE: 207

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 208
<211> LENGTH: 108
<212> TYPE: PRT
<213> ORGANISM: Artificial Sequence
<220> FEATURE:
<223> OTHER INFORMATION: Synthetic: Fig. 13A Light Chain Variable
      Region: 6266.15

-continued

```
<400> SEQUENCE: 208

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Ile Leu Trp Pro Pro
                85                  90                  95

Arg Thr Phe Gly Gly Gly Thr Lys Val Glu Ile Lys
            100                 105

<210> SEQ ID NO 209
<211> LENGTH: 120
<212> TYPE: PRT
<213> ORGANISM: Artificial Sequence
<220> FEATURE:
<223> OTHER INFORMATION: Synthetic:  Fig. 13B Heavy chain variable
      region: 6266.8

<400> SEQUENCE: 209

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Lys Gly Tyr
            20                  25                  30

Gly Val Ser Trp Val Arg Gln Ala Pro Gly Gln Gly Leu Glu Trp Met
        35                  40                  45

Gly Asn Ile Ile Pro Gly Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Thr Lys Tyr Gly Met Leu Asp Val Trp Gly Gln
            100                 105                 110

Gly Thr Met Val Thr Val Ser Ser
        115                 120

<210> SEQ ID NO 210
<211> LENGTH: 120
<212> TYPE: PRT
<213> ORGANISM: Artificial Sequence
<220> FEATURE:
<223> OTHER INFORMATION: Synthetic:  Fig. 13B Heavy chain variable
      region: 6266.9

<400> SEQUENCE: 210

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Lys Gly Tyr
            20                  25                  30

Gly Val Ser Trp Val Arg Gln Ala Pro Gly Gln Gly Leu Glu Trp Met
        35                  40                  45
```

Gly Asn Ile Ile Pro Gly Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Gly Gly Thr Lys Tyr Gly Met Leu Asp Val Trp Gly Gln
            100                 105                 110

Gly Thr Met Val Thr Val Ser Ser
            115                 120

<210> SEQ ID NO 211
<211> LENGTH: 120
<212> TYPE: PRT
<213> ORGANISM: Artificial Sequence
<220> FEATURE:
<223> OTHER INFORMATION: Synthetic: Fig. 13B Heavy chain variable
      region: 6266.1

<400> SEQUENCE: 211

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Leu Ser Gly Tyr
            20                  25                  30

Gly Val Ser Trp Val Arg Gln Ala Pro Gly Gln Gly Leu Glu Trp Met
            35                  40                  45

Gly Asn Ile Ile Pro Gly Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
            115                 120

<210> SEQ ID NO 212
<211> LENGTH: 120
<212> TYPE: PRT
<213> ORGANISM: Artificial Sequence
<220> FEATURE:
<223> OTHER INFORMATION: Synthetic: Fig. 13B Heavy chain variable
      region: 6266.11

<400> SEQUENCE: 212

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Leu Ser Gly Tyr
            20                  25                  30

Gly Val Ser Trp Val Arg Gln Ala Pro Gly Gln Gly Leu Glu Trp Met
            35                  40                  45

Gly Asn Ile Ile Pro Gly Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
        115                 120

<210> SEQ ID NO 213
<211> LENGTH: 120
<212> TYPE: PRT
<213> ORGANISM: Artificial Sequence
<220> FEATURE:
<223> OTHER INFORMATION: Synthetic: Fig. 13B Heavy chain variable
      region: 6266.12

<400> SEQUENCE: 213

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Asn Gly Tyr
            20                  25                  30

Gly Val Ser Trp Val Arg Gln Ala Pro Gly Gln Gly Leu Glu Trp Met
        35                  40                  45

Gly Asn Ile Ile Pro Gly Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
        115                 120

<210> SEQ ID NO 214
<211> LENGTH: 120
<212> TYPE: PRT
<213> ORGANISM: Artificial Sequence
<220> FEATURE:
<223> OTHER INFORMATION: Synthetic: Fig. 13B Heavy chain variable
      region: 6266.13

<400> SEQUENCE: 214

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Gly Tyr
            20                  25                  30

Gly Met Ser Trp Val Arg Gln Ala Pro Gly Gln Gly Leu Glu Trp Met
        35                  40                  45

Gly Asn Ile Ile Pro Gly Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Met Leu Asp Val Trp Gly Gln
            100                 105                 110

Gly Thr Met Val Thr Val Ser Ser
        115                 120

<210> SEQ ID NO 215
<211> LENGTH: 120

```
<212> TYPE: PRT
<213> ORGANISM: Artificial Sequence
<220> FEATURE:
<223> OTHER INFORMATION: Synthetic:  Fig. 13B Heavy chain variable
      region: 6266.14

<400> SEQUENCE: 215

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Leu Ser Gly Tyr
            20                  25                  30

Gly Val Ser Trp Val Arg Gln Ala Pro Gly Gln Gly Leu Glu Trp Met
        35                  40                  45

Gly Asn Ile Ile Pro Gly Phe Gly Val Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Trp Gly Met Leu Asp Val Trp Gly Gln
            100                 105                 110

Gly Thr Met Val Thr Val Ser Ser
        115                 120

<210> SEQ ID NO 216
<211> LENGTH: 120
<212> TYPE: PRT
<213> ORGANISM: Artificial Sequence
<220> FEATURE:
<223> OTHER INFORMATION: Synthetic:  Fig. 13B Heavy chain variable
      region: 6266.15

<400> SEQUENCE: 216

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Leu Ser Gly Tyr
            20                  25                  30

Gly Val Ser Trp Val Arg Gln Ala Pro Gly Gln Gly Leu Glu Trp Met
        35                  40                  45

Gly Asn Ile Ile Pro Gly Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Thr Lys Tyr Gly Glu Leu Asp Val Trp Gly Gln
            100                 105                 110

Gly Thr Met Val Thr Val Ser Ser
        115                 120

<210> SEQ ID NO 217
<211> LENGTH: 7
<212> TYPE: PRT
<213> ORGANISM: Artificial Sequence
<220> FEATURE:
<223> OTHER INFORMATION: Synthetic:  VL HVR2 of 6266.3, 6266.6, 6266.7,
      6266.8, 6266.11
```

<400> SEQUENCE: 217

Gly Ala Ser Thr Arg Ala Tyr
1               5

<210> SEQ ID NO 218
<211> LENGTH: 9
<212> TYPE: PRT
<213> ORGANISM: Artificial Sequence
<220> FEATURE:
<223> OTHER INFORMATION: Synthetic:  VH HVR1 of 6266.1, 6266.2, 6266.3,
      6266.4, 6266.5, 6266.6,6266.7

<400> SEQUENCE: 218

Gly Thr Leu Ser His Tyr Gly Val Ser
1               5

<210> SEQ ID NO 219
<211> LENGTH: 17
<212> TYPE: PRT
<213> ORGANISM: Artificial Sequence
<220> FEATURE:
<223> OTHER INFORMATION: Synthetic:  VH HVR2 of 6266.1, 6266.2, 6266.3,
      6266.4, 6266.5, 6266.6,6266.7

<400> SEQUENCE: 219

Asn Ile Ile Pro Gly Ile Gly Thr Ala Asn Tyr Ala Gln Lys Phe Gln
1               5                   10                  15

Gly

<210> SEQ ID NO 220
<211> LENGTH: 13
<212> TYPE: PRT
<213> ORGANISM: Artificial Sequence
<220> FEATURE:
<223> OTHER INFORMATION: Synthetic:  VH HVR3 for 6266.5, 6266.6

<400> SEQUENCE: 220

Ala Arg Ser Gly Gly Thr Gln Tyr Gly Met Leu Asp Val
1               5                   10

<210> SEQ ID NO 221
<211> LENGTH: 13
<212> TYPE: PRT
<213> ORGANISM: Artificial Sequence
<220> FEATURE:
<223> OTHER INFORMATION: Synthetic:  VH HVR3 for 6266.7, 6266.15

<400> SEQUENCE: 221

Ala Arg Ser Gly Gly Thr Lys Tyr Gly Glu Leu Asp Val
1               5                   10

<210> SEQ ID NO 222
<211> LENGTH: 9
<212> TYPE: PRT
<213> ORGANISM: Artificial Sequence
<220> FEATURE:
<223> OTHER INFORMATION: Synthetic:  VH HVR1 for 6266.8, 6266.9

<400> SEQUENCE: 222

Gly Thr Leu Lys Gly Tyr Gly Val Ser
1               5

<210> SEQ ID NO 223
<211> LENGTH: 9
<212> TYPE: PRT

```
<213> ORGANISM: Artificial Sequence
<220> FEATURE:
<223> OTHER INFORMATION: Synthetic: VH HVR1 for 6266.12

<400> SEQUENCE: 223

Gly Thr Leu Asn Gly Tyr Gly Val Ser
1               5

<210> SEQ ID NO 224
<211> LENGTH: 9
<212> TYPE: PRT
<213> ORGANISM: Artificial Sequence
<220> FEATURE:
<223> OTHER INFORMATION: Synthetic: VH HVR1 for 6266.13

<400> SEQUENCE: 224

Gly Thr Leu Ser Gly Tyr Gly Met Ser
1               5

<210> SEQ ID NO 225
<211> LENGTH: 17
<212> TYPE: PRT
<213> ORGANISM: Artificial Sequence
<220> FEATURE:
<223> OTHER INFORMATION: Synthetic: VH HVR2 for 6266.14

<400> SEQUENCE: 225

Asn Ile Ile Pro Gly Phe Gly Val Ala Asn Tyr Ala Gln Lys Phe Gln
1               5                   10                  15

Gly

<210> SEQ ID NO 226
<211> LENGTH: 13
<212> TYPE: PRT
<213> ORGANISM: Artificial Sequence
<220> FEATURE:
<223> OTHER INFORMATION: Synthetic: VH HVR3 for 6266.8, 6266.9

<400> SEQUENCE: 226

Ala Arg Gly Gly Gly Thr Lys Tyr Gly Met Leu Asp Val
1               5                   10

<210> SEQ ID NO 227
<211> LENGTH: 13
<212> TYPE: PRT
<213> ORGANISM: Artificial Sequence
<220> FEATURE:
<223> OTHER INFORMATION: Synthetic: VH HVR3 for 6266.14

<400> SEQUENCE: 227

Ala Arg Ser Gly Gly Thr Lys Trp Gly Met Leu Asp Val
1               5                   10

<210> SEQ ID NO 228
<211> LENGTH: 501
<212> TYPE: PRT
<213> ORGANISM: Mouse sp.
<220> FEATURE:
<221> NAME/KEY: misc_feature
<223> OTHER INFORMATION: Murine BACE1, isoform 1

<400> SEQUENCE: 228

Met Ala Pro Ala Leu His Trp Leu Leu Leu Trp Val Gly Ser Gly Met
1               5                   10                  15

Leu Pro Ala Gln Gly Thr His Leu Gly Ile Arg Leu Pro Leu Arg Ser
                20                  25                  30
```

```
Gly Leu Ala Gly Pro Pro Leu Gly Leu Arg Leu Pro Arg Glu Thr Asp
        35                  40                  45

Glu Glu Ser Glu Glu Pro Gly Arg Arg Gly Ser Phe Val Glu Met Val
50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
                100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
        130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
        180                 185                 190

Ser Leu Glu Pro Phe Phe Asp Ser Leu Val Lys Gln Thr His Ile Pro
        195                 200                 205

Asn Ile Phe Ser Leu Gln Leu Cys Gly Ala Gly Phe Pro Leu Asn Gln
210                 215                 220

Thr Glu Ala Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
        260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
        290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
        340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
370                 375                 380

Val Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
        420                 425                 430

Gly Pro Phe Val Thr Ala Asp Met Glu Asp Cys Gly Tyr Asn Ile Pro
        435                 440                 445
```

-continued

```
Gln Thr Asp Glu Ser Thr Leu Met Thr Ile Ala Tyr Val Met Ala Ala
    450                 455                 460

Ile Cys Ala Leu Phe Met Leu Pro Leu Cys Leu Met Val Cys Gln Trp
465                 470                 475                 480

Arg Cys Leu Arg Cys Leu Arg His Gln His Asp Asp Phe Ala Asp Asp
                485                 490                 495

Ile Ser Leu Leu Lys
            500

<210> SEQ ID NO 229
<211> LENGTH: 467
<212> TYPE: PRT
<213> ORGANISM: Mouse sp.
<220> FEATURE:
<221> NAME/KEY: misc_feature
<223> OTHER INFORMATION: Murine BACE1, isoform 2

<400> SEQUENCE: 229

Met Ala Pro Ala Leu His Trp Leu Leu Leu Trp Val Gly Ser Gly Met
1               5                   10                  15

Leu Pro Ala Gln Gly Thr His Leu Gly Ile Arg Leu Pro Leu Arg Ser
            20                  25                  30

Gly Leu Ala Gly Pro Pro Leu Gly Leu Arg Leu Pro Arg Glu Thr Asp
        35                  40                  45

Glu Glu Ser Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Ile Pro
        195                 200                 205

Asn Ile Phe Ser Leu Gln Leu Cys Gly Ala Gly Phe Pro Leu Asn Gln
    210                 215                 220

Thr Glu Ala Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Thr Glu Lys Phe Pro Asp Gly Phe
        275                 280                 285

Trp Leu Gly Glu Gln Leu Val Cys Trp Gln Ala Gly Thr Thr Pro Trp
    290                 295                 300
```

```
Asn Ile Phe Pro Val Ile Ser Leu Tyr Leu Met Gly Glu Val Thr Asn
305                 310                 315                 320

Gln Ser Phe Arg Ile Thr Ile Leu Pro Gln Gln Tyr Leu Arg Pro Val
            325                 330                 335

Glu Asp Val Ala Thr Ser Gln Asp Asp Cys Tyr Lys Phe Ala Val Ser
        340                 345                 350

Gln Ser Ser Thr Gly Thr Val Met Gly Ala Val Ile Met Glu Gly Phe
    355                 360                 365

Tyr Val Val Phe Asp Arg Ala Arg Lys Arg Ile Gly Phe Ala Val Ser
370                 375                 380

Ala Cys His Val His Asp Glu Phe Arg Thr Ala Ala Val Glu Gly Pro
385                 390                 395                 400

Phe Val Thr Ala Asp Met Glu Asp Cys Gly Tyr Asn Ile Pro Gln Thr
            405                 410                 415

Asp Glu Ser Thr Leu Met Thr Ile Ala Tyr Val Met Ala Ala Ile Cys
        420                 425                 430

Ala Leu Phe Met Leu Pro Leu Cys Leu Met Val Cys Gln Trp Arg Cys
    435                 440                 445

Leu Arg Cys Leu Arg His Gln His Asp Phe Ala Asp Asp Ile Ser
450                 455                 460

Leu Leu Lys
465

<210> SEQ ID NO 230
<211> LENGTH: 460
<212> TYPE: PRT
<213> ORGANISM: Artificial Sequence
<220> FEATURE:
<223> OTHER INFORMATION: Synthetic:  human BACE1 ECD

<400> SEQUENCE: 230

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
            85                  90                  95

Ser Asn Phe Ala Val Gly Ala Ala Pro His Pro Phe Leu His Arg Tyr
        100                 105                 110

Tyr Gln Arg Gln Leu Ser Ser Thr Tyr Arg Asp Leu Arg Lys Gly Val
    115                 120                 125

Tyr Val Pro Tyr Thr Gln Gly Lys Trp Glu Gly Glu Leu Gly Thr Asp
130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
            165                 170                 175

Glu Gly Ile Leu Gly Leu Ala Tyr Ala Glu Ile Ala Arg Pro Asp Asp
        180                 185                 190
```

Ser Leu Glu Pro Phe Phe Asp Ser Leu Val Lys Gln Thr His Val Pro
            195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
                260                 265                 270

Asp Leu Lys Met Asp Cys Lys Glu Tyr Asn Tyr Asp Lys Ser Ile Val
            275                 280                 285

Asp Ser Gly Thr Thr Asn Leu Arg Leu Pro Lys Lys Val Phe Glu Ala
        290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
        435                 440                 445

Gln Thr Asp Glu Ser Thr Leu Met Thr Gly Arg Ala
    450                 455                 460

<210> SEQ ID NO 231
<211> LENGTH: 460
<212> TYPE: PRT
<213> ORGANISM: Artificial Sequence
<220> FEATURE:
<223> OTHER INFORMATION: Synthetic: Murine BACE1 ECD

<400> SEQUENCE: 231

Met Ala Pro Ala Leu His Trp Leu Leu Leu Trp Val Gly Ser Gly Met
1               5                   10                  15

Leu Pro Ala Gln Gly Thr His Leu Gly Ile Arg Leu Pro Leu Arg Ser
            20                  25                  30

Gly Leu Ala Gly Pro Pro Leu Gly Leu Arg Leu Pro Arg Glu Thr Asp
        35                  40                  45

Glu Glu Ser Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

```
Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
            115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Ile Pro
        195                 200                 205

Asn Ile Phe Ser Leu Gln Leu Cys Gly Ala Gly Phe Pro Leu Asn Gln
    210                 215                 220

Thr Glu Ala Leu Ala Ser Val Gly Gly Ser Met Ile Ile Gly Gly Ile
225                 230                 235                 240

Asp His Ser Leu Tyr Thr Gly Arg Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
        340                 345                 350

Thr Asn Gln Ser Phe Arg Ile Thr Ile Leu Pro Gln Gln Tyr Leu Arg
    355                 360                 365

Pro Val Glu Asp Val Ala Thr Ser Gln Asp Asp Cys Tyr Lys Phe Ala
    370                 375                 380

Val Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
                420                 425                 430

Gly Pro Phe Val Thr Ala Asp Met Glu Asp Cys Gly Tyr Asn Ile Pro
        435                 440                 445

Gln Thr Asp Glu Ser Thr Leu Met Thr Gly Arg Ala
    450                 455                 460

<210> SEQ ID NO 232
<211> LENGTH: 17
<212> TYPE: PRT
<213> ORGANISM: Artificial Sequence
<220> FEATURE:
<223> OTHER INFORMATION: Synthetic: VH HVR2
```

<400> SEQUENCE: 232

Asn Ile Ile Pro Ile Phe Gly Thr Ala Thr Tyr Ala Gln Lys Phe Gln
1               5                   10                  15

Gly